United States Patent [19]
Lucas et al.

[11] Patent Number: 5,891,679
[45] Date of Patent: Apr. 6, 1999

[54] TNF-ALPHA MUTEINS AND A PROCESS FOR PREPARING THEM

[75] Inventors: Rudolph Lucas, Brussels; Patrick De Baetselier, Berchem; Lucia Fransen, Eke; Erwin Sablon, Opwijk, all of Belgium

[73] Assignee: N.V. Innogenetics S.A., Ghent, Belgium

[21] Appl. No.: 500,860

[22] PCT Filed: Feb. 2, 1994

[86] PCT No.: PCT/EP94/00286

§ 371 Date: Sep. 15, 1995

§ 102(e) Date: Sep. 15, 1995

[87] PCT Pub. No.: WO94/18325

PCT Pub. Date: Aug. 18, 1994

[30] Foreign Application Priority Data

Feb. 3, 1993 [EP] European Pat. Off. ............. 93400262

[51] Int. Cl.$^6$ ............................. C12N 15/19; C07K 14/52
[52] U.S. Cl. ................. 435/69.5; 435/252.5; 435/320.1; 536/23.5; 530/351; 424/85.1
[58] Field of Search .......................... 530/351; 435/69.5, 435/252.3, 320.1; 424/85.1; 536/23.5

[56] References Cited

FOREIGN PATENT DOCUMENTS

| 0 168 214 A2 | 1/1986 | European Pat. Off. . |
|---|---|---|
| 0 414 607 A2 | 8/1989 | European Pat. Off. . |
| 0 479 071 A2 | 4/1992 | European Pat. Off. . |
| 0477791 | 4/1992 | European Pat. Off. . |
| 2263199 | 11/1987 | Japan . |
| 3270697 | 11/1988 | Japan . |
| 3-197498 | 8/1991 | Japan . |
| 3197498 | 8/1991 | Japan . |
| 4182497 | 6/1992 | Japan . |
| 5271290 | 10/1993 | Japan . |

OTHER PUBLICATIONS

Goh et al., *Protein Engineering* 4(2) 1991, pp. 785–791.
Kircheis et al, Inmunology 1992, 76, pp. 433–438.
Protein Engineering, vol. 3, 1990, pp. 713–719, J. Yamagishi et al Mutational analysis of structure–activity relationships in human tumor necrosis factor–alpha *abstract; Table II(a) amd (b).
Protein Engineering, vol. 3, 1990, pp. 721–724, T. Arakawa et al; 'Alteration in folding efficiency and conformation of recombinant human tumor necrosis factor–alpha by replacing cysteines 69 and 101 with aspartic acid 69 and arginine 101' *abstract.
Science, vol. 263, 11 Feb. 1994, pp. 814–817, R. Lucas et al; 'Mapping the lectin–like activity of tumor necrosis factor' *whole document.
Biochimica et Biophysica Acta, 1096 (1991) pp. 245–252, Ito et al; 'Novel muteins of human tumor necrosis factor β'.
Tibtech, vol. 8, Jun. 1990, Undercurrents, Complementarity of peptides specified by 'sense' and 'antisense' strands of DNA.

*Primary Examiner*—Garnette D. Draper
*Attorney, Agent, or Firm*—Nixon & Vanderhye, P.C.

[57] ABSTRACT

The invention relates to tumor necrosis factor muteins characterized in that the TNF-α amino acid sequence is mutated, or deleted totally or partially, in the region containing position 101 to 116 in such a way that:

either the lectin-like activity is reduced with respect to TNF-α, or the toxic activity is reduced with respect to TNF-α; and providing that said muteins have largely retained the tumoricidal activity of TNF-α; and with said muteins possibly containing in their peptidic chain additional modifications consisting of substitutions and/or deletions and/or additions of one or several amino acid residues, and with said muteins being characterized in that they have retained the aforementioned activities; or a pharmaceutically acceptable salt thereof.

22 Claims, 17 Drawing Sheets

| | | | | | |
|---|---|---|---|---|---|
| TTCCGGGGAT | CTCTCACCTA | CCAAACAATG | CCCCCCTGCA | AAAATAAAT | TCATATAAAA | 60
| AACATACAGA | TAACCATCTG | CGGTGATAAA | TTATCTCTGG | CGGTGTTGAC | ATAAATACCA | 120
| CTGGCGGTGA | TACTGAGCAC | ATCAGCAGGA | CGCACTGACC | ACCATGAAGG | TGACGCTCTT | 180
| AAAAATTAAG | CCCTGAAGAA | GGGCAGGGGT | ACCAGGAGGT | TTAAATATTC | CATGGGGGGG | 240
| ATCCTCTAGA | GTCGACCTGC | AGCCCAAGCT | TGGCTGTTTT | GGCGGATGAG | AGAAGATTTT | 300
| CAGCCTGATA | CAGATTAAAT | CAGAACGCAG | AAGCGGTCTG | ATAAAACAGA | ATTTGCCTGG | 360
| CGGCAGTAGC | GCGGTGGTCC | CACCTGACCC | CATGCCGAAC | TCAGAAGTGA | AACGCCGTAG | 420
| CGCCGATGGT | AGTGTGGGGT | CTCCCCATGC | GAGAGTAGGG | AACTGCCAGG | CATCAAATAA | 480
| AACGAAAGGC | TCAGTCGAAA | GACTGGGCCT | TTCGTTTTAT | CTGTTGTTTG | TCGGTGAACG | 540
| CTCTCCTGAG | TAGGACAAAT | CCGCCGGGAG | CGGATTTGAA | CGTTGCGAAG | CAACGGCCCG | 600
| GAGGGTGGCG | GGCAGGACGC | CGCCATAAA | CTGCCAGGCA | TCAAATTAAG | CAGAAGGCCA | 660
| TCCTGACGGA | TGGCCTTTTT | GCGTTTCTAC | AAACTCTTTT | GTTTATTTT | CTAAATACAT | 720
| TCAAATATGT | ATCCGCTCAT | GAGACAATAA | CCCTGATAAA | TGCTTCAATA | ATAAAAGGAT | 780
| CTAGGTGAAG | ATCCTTTTTG | ATAATCTCAT | GACCAAAATC | CCTTAACGTG | AGTTTTCGTT | 840
| CCACTGAGCG | TCAGACCCCG | TAGAAAAGAT | CAAAGGATCT | TCTTGAGATC | CTTTTTTCT | 900
| GCGCGTAATC | TGCTGCTTGC | AAACAAAAAA | ACCACCGCTA | CCAGCGGTGG | TTTGTTTGCC | 960

*Fig. 2A*

```
GGATCAAGAG CTACCAACTC TTTTTCCGAA GGTAACTGGC TTCAGCAGAG CGCAGATACC  1020

AAATACTGTC CTTCTAGTGT AGCCGTAGTT AGCCCACCAC TTCAAGAACT CTGTAGCACC  1080

GCCTACATAC CTCGCTCTGC TAATCCTGTT ACCAGTGGCT GCTGCCAGTG GCGATAAGTC  1140

GTGTCTTACC GGGTTGGACT CAAGACGATA GTTACCGGAT AAGGGCCAGC GGTCGGGCTG  1200

AACGGGGGT TCGTGCACAC AGCCCAGCTT GGAGCGAACG ACCTACACCG AACTGAGATA  1260

CCTACAGCGT GAGCATTGAG AAAGCGCCAC GCTTCCCGAA GGGAGAAAGG CGGACAGGTA  1320

TCCGGTAAGC GGCAGGGTCG GAACAGGAGA GCGCACGAGG GAGCTTCCAG GGGGAAACGC  1380

CTGGTATCTT TATAGTCCTG TCGGGTTTCG CCACCTCTGA CTTGAGCGTC GATTTTTGTG  1440

ATGCTCGTCA GGGGGGCGGA GCCTATGGAA AAACGCCAGC AACGCGGCCT TTTTACGGTT  1500

CCTGGCCTTT TGCTGGCCTT TTGCTCACAT GTTCTTTCCT GCGTTATCCC CTGATTCTGT  1560

GGATAACCGT ATTACCGCCT TTGAGTGAGC TGATACCGCT CGCCGCAGCC GAACGACCGA  1620

GCGCAGCGAG TCAGTGAGCG AGGAAGCGGA AGAGCGCTGA CTTCCGCGTT TCCAGACTTT  1680

ACGAAACACG GAAACCGAAG ACCATTCATG TTGTTGCTCA GGTCGCAGAC GTTTTGCAGC  1740

AGCAGTCGCT TCACGTTCGC TCGCGTATCG GTGATTCATT CTGCTAACCA GTAAGGCAAC  1800

CCCGCCAGCC TAGCCGGGTC CTCAACGACA GGAGCACGAT CATGCGCACC CGTGGCCAGG  1860

ACCCAACGCT GCCCGAGATG CGCCGCGTGC GGCTGCTGGA GATGGCGGAC GCGATGGATA  1920
```

Fig. 2B

```
TGTTCTGCCA AGGGTTGGTT TGGGCATTCA CAGTTCTCCG CAAGAATTGA TTGGCTCCAA    1980
TTCTTGGAGT GGTGAATCCG TTAGCGAGGT GCCGCCGGCT TCCATTCAGG TCGAGGTGGC    2040
CCGGCTCCAT GCACCGCGAC GCAACGCGGG GAGGCAGACA AGGTATAGGG CGGCGCCTAC    2100
AATCCATGCC AACCCGTTCC ATGTGCTCGC CGAGGCGGCA TAAATCGCCG TGACGATCAG    2160
CGGTCCAGTG ATCGAAGTTA GGCTGGTAAG AGCCGCGAGC GATCCTTGAA GCTGTCCCTG    2220
ATGGTCGTCA TCTACCTGCC TGGACAGCAT GGCCTGCAAC GCGGGCATCC CGATGCCGCC    2280
GGAAGCGAGA AGAATCATAA TGGGGAAGGC CATCCAGCCT CGCGTCGCGA ACGCCAGCAA    2340
GACGTAGCCC AGCGCGTCGG CCGCCATGCC GGCGATAATG GCCTGCTTCT CGCCGAAACG    2400
TTTGGTGGCG GGACCAGTGA CGAAGGCTTG AGCGAGGGCG TGCAAGATTC CGAATACCGC    2460
AAGCGACAGG CCGATCATCG TCGCGCTCCA GCGAAAGCGG TCCTCGCCGA AAATGACCCA    2520
GAGCGCTGCC GGCACCTGTC CTACGAGTTG CATGATAAAG AAGACAGTCA TAAGTGCGGC    2580
GACGATAGTC ATGCCCCGCG CCCACCGGAA GGAGCTGACT GGGTTGAAGG CTCTCAAGGG    2640
CATCGGTCGA CGCTCTCCCT TATGCGACTC CTGCATTAGG AAGCAGCCCA GTAGTAGGTT    2700
GAGGCCGTTG AGCACCGCCG CCGCAAGGAA TGGTGCATGC AAGGAGATGG CGCCAACAG    2760
TCCCCCGGCC ACGGGGCCTG CCACCATACC CACGCCGAAA CAAGCGCTCA TGAGCCCGAA    2820
GTGGCGAGCC CGATCTTCCC CATCGGTGAT GTCGGCGATA TAGGCGCCAG CAACCGCACC    2880
```

*Fig. 2C*

```
TGTGGGCGCCG GTGATGCCGG CCACGATGCG TCCGGCGTAG AGGATCCACA GGACGGGTGT    2940
GGTCGCCATG ATCGCGTAGT CGATAGTGGC TCCAAGTAGC GAAGCGAGCA GGACTGGGCG    3000
GCGGCCAAAG CGGTCGGACA GTGCTCCGAG AACGGGTGCG CATAGAAATT GCATCAACGC    3060
ATATAGCGCT AGCAGCACGC CATAGTGACT GGCGATGCTG TCGGAATGGA CGATATCCCG    3120
CAAGAGGCCC GGCAGTACCG GCATAACCAA GCCTATGCCT ACAGCATCCA GGGTGACGGT    3180
GCCGAGGATG ACGATGAGCG CATTGTTAGA TTTCATACAC GGTGCCTGAC TGCGTTAGCA    3240
ATTTAACTGT GATAAACTAC CGCATTAAAG CTTATCGATG ATAAGCTGTC AAACATGAGA    3300
           GCCCCGCGCC CACCGGAAGG AGCTGACTGG GTTGAAGGCT CTCAAGGGCA TCGGTCGACG    3360
           CTCTCCCTTA TGCGACTCCT GCATTAGGAA GCAGCCCAGT AGTAGGTTGA GGCCGTTGAG    3420
           CACCGCCGCC GCAAGGAATG GTGCATGCAA GGAGATGGCG CCCAACAGTC CCCCGGCCAC    3480
           GGGGCCTGCC ACCATACCCA CGCCGAAACA AGCGCTCATG AGCCCGAAGT GGCGAGCCCG    3540
           ATCTTCCCCA TCGGTGATGT CGGCGATATA GGCGCCAGCA ACCGCACCTG TGGCGCCGGT    3600
           GATGCCGGCC ACGATGCGTC CGGCGTAGAG GATCCACAGG ACGGGTGTGG TCGCCATGAT    3660
           CGCGTAGTCG ATAGTGGCTC CAAGTAGCGA AGCGAGCAGG ACTGGGCGGC GGCCAAAGCG    3720
           GTCGGACAGT GCTCCGAGAA CGGGTGCGCA TAGAAATTGC ATCAACGCAT ATAGCGCTAG    3780
           CAGCACGCCA TAGTGACTGG CGATGCTGTC GGAATGGACG ATATCCCGCA AGAGGCCCGG    3840
           CAGTACCGGC ATAACCAAGC CTATGCCTAC AGCATCCAGG GTGACGGTGC CGAGGATGAC    3900
           GATGAGCGCA TTGTTAGATT TCATACACGG TGCCTGACTG CGTTAGCAAT TTAACTGTGA    3960
           TAAACTACCG CATTAAAGCT TATCGATGAT AAGCTGTCAA ACATGAGAA              4009
```

*Fig. 2D*

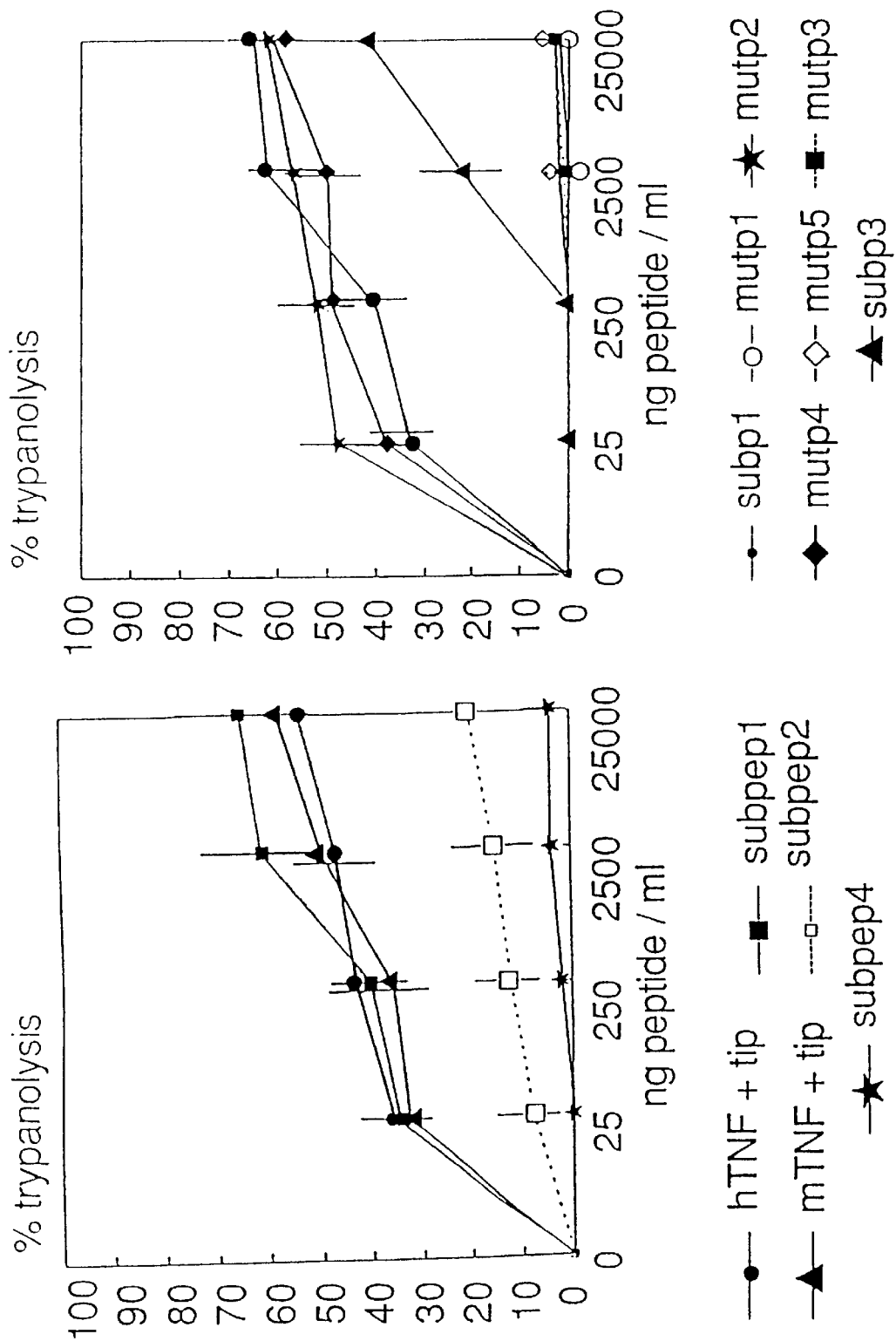

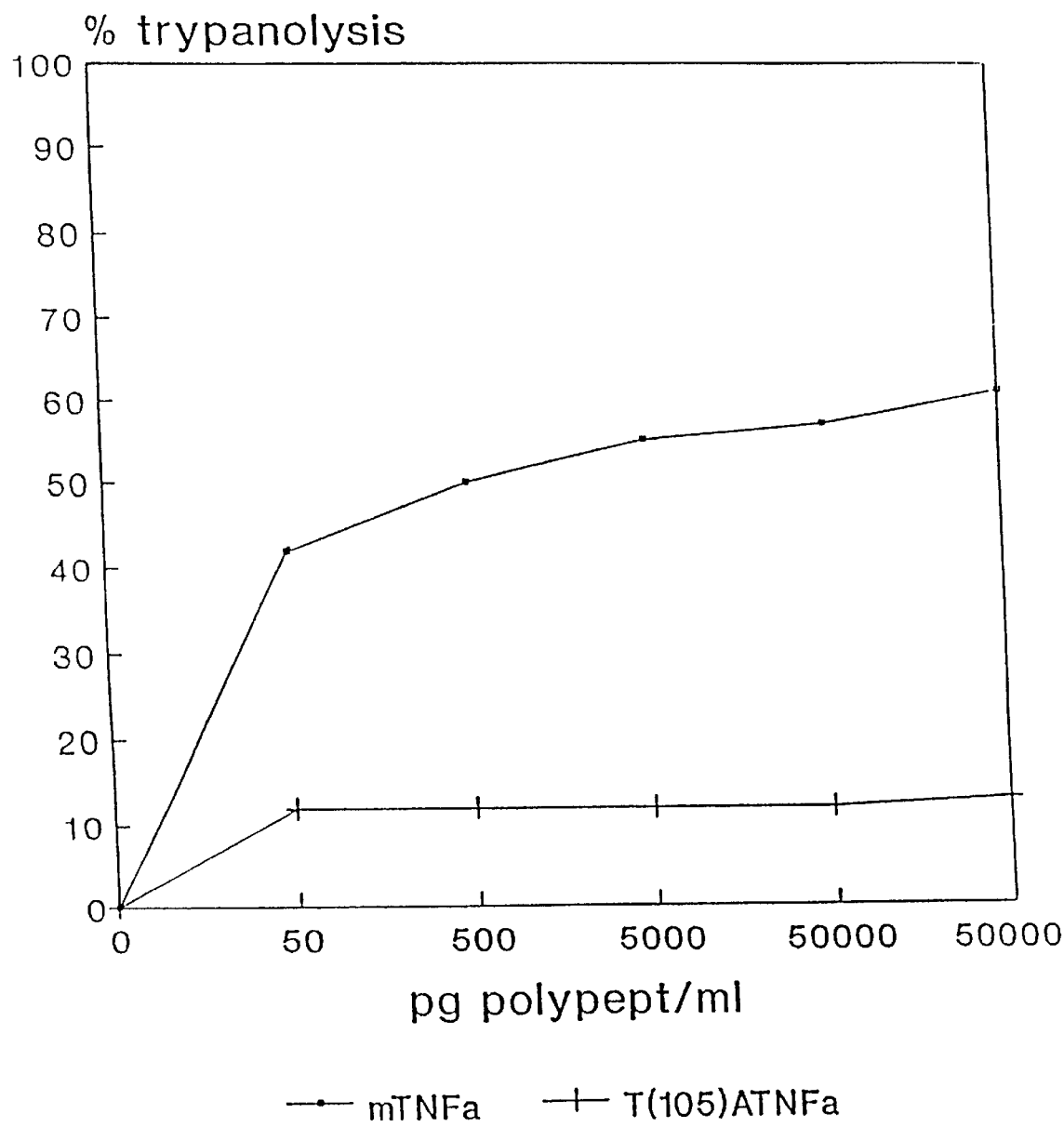

Fig. 13A
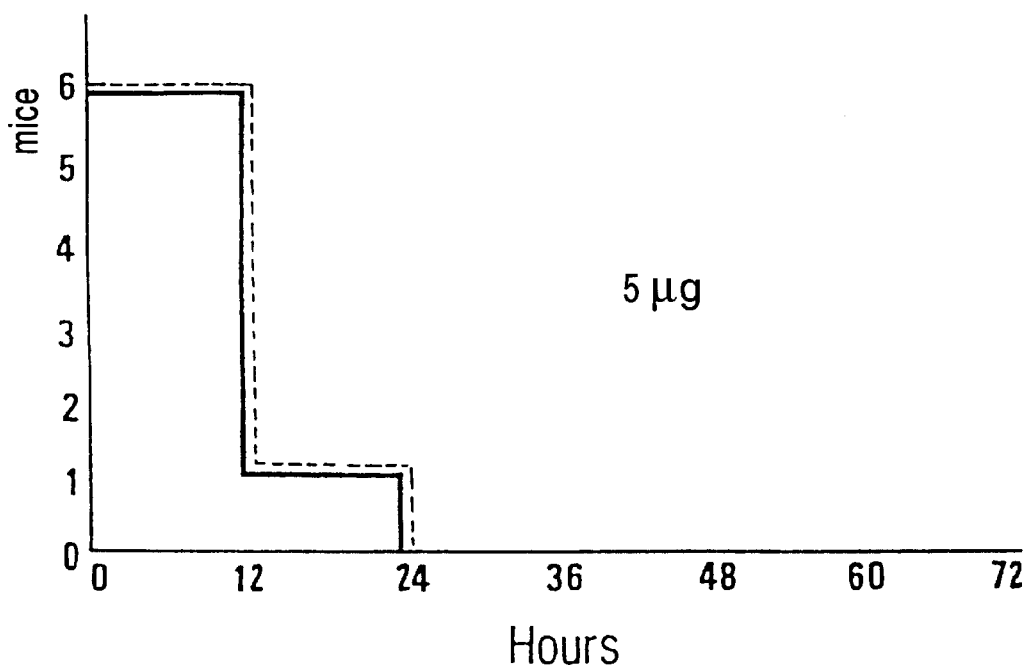
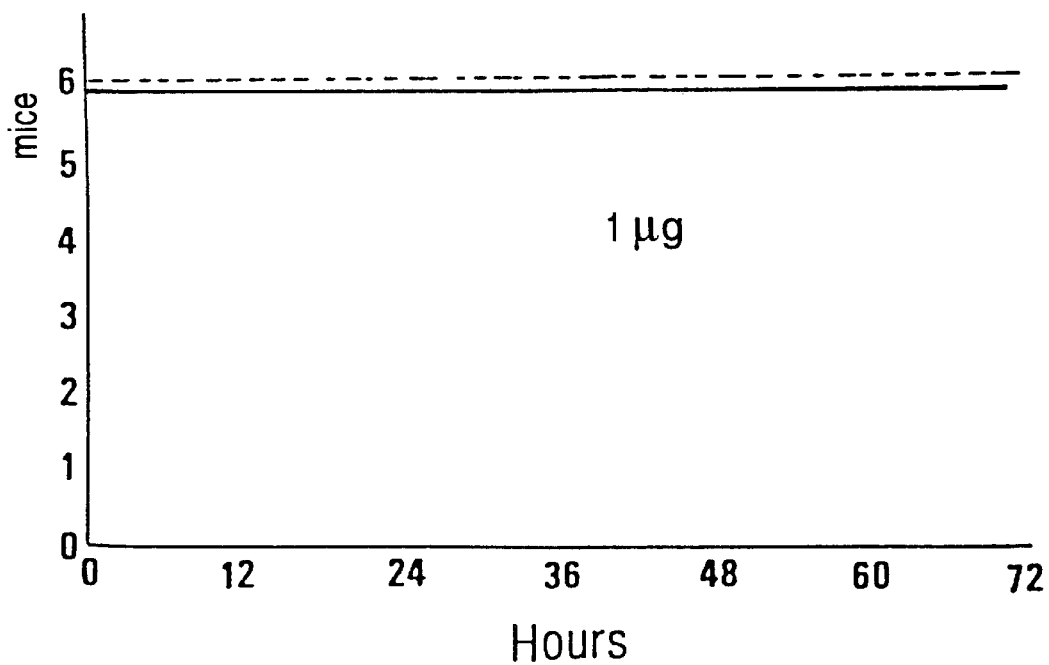
Fig. 13B

Fig. 13C
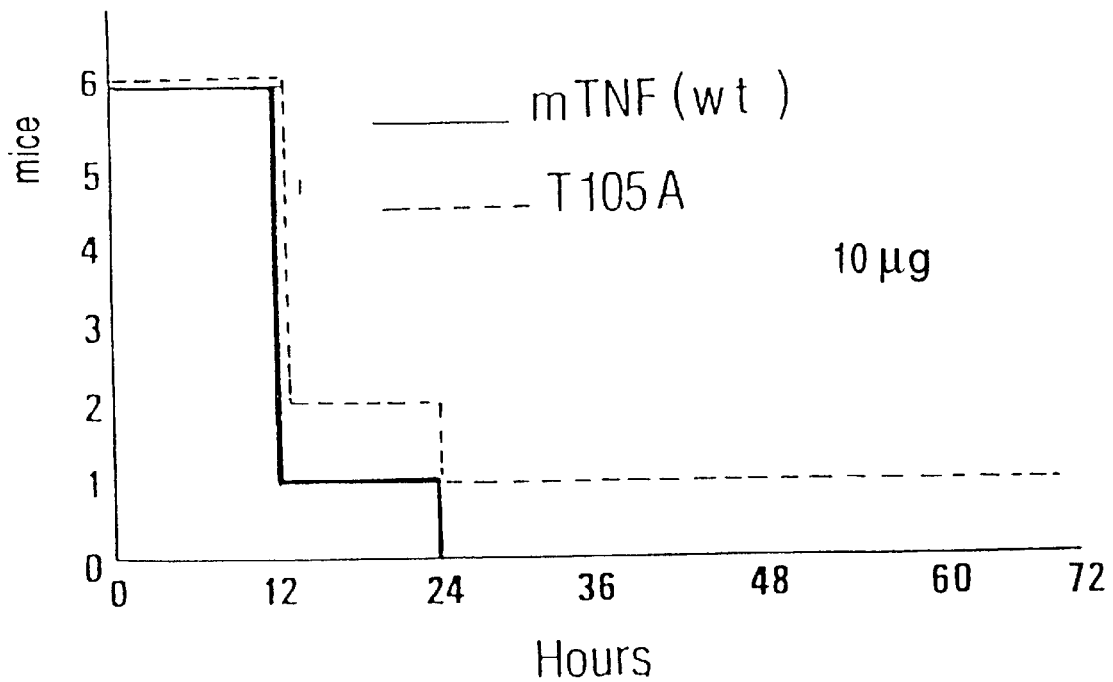
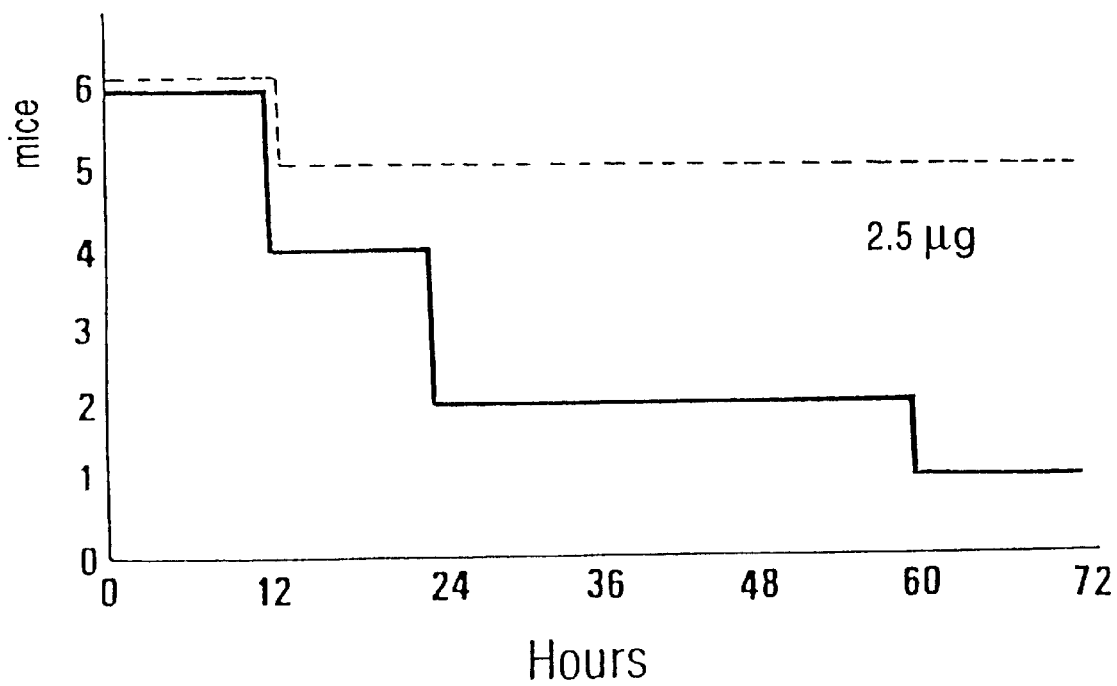
Fig. 13D

TNF-ALPHA MUTEINS AND A PROCESS FOR PREPARING THEM

The present invention relates to TNF-α-muteins, a process for preparing them and their use as active substances in pharmaceutical compositions.

BACKGROUND OF THE INVENTION

Tumor necrosis factor-α (TNF-α), also known as cachectin, is a multifunctional cytokine produced mainly by activated macrophages. In vitro, it has diverse biological effects (reviewed by Manogue et Cerami, 1988) including killing of transformed cells (Carswell et al., 1975), stimulation of granulocytes and fibroblasts (Old, 1985; Vilchek et al., 1986; Beutler and Cerami, 1987), damage to endothelial cells (Sato et al, 1986), and anti-parasitic effects (Taverne et al., 1984). In vivo, it plays a key role as an endogenous mediator of inflammatory, immune and host defence functions and it is involved in a number of pathological conditions in man and mouse such as septic shock, cachexia, capillary leak syndrome, hemorhagic necrosis of multiple organs, etc. It is capable of acting independently and in conjunction with other factors affecting a whole plethora of different body functions. These effects can either be beneficial or life-threatening to the host. Some of these effects are direct, others may be mediated via the induction of other secreted factors. The biological effects of TNF-α are mediated via binding to specific cell surface receptors.

The primary structure of human and mouse TNF-α (Pennica et al., 1984; Fransen et al., 1985) and of two different TNF-receptors (p55-TNF-R and p75-TNF-R) has been deduced from the nucleotide sequence of the cloned cDNA (Dembic et al., 1990; Loetscher et al., 1990). Both receptors bind not only TNF-α but also TNF-β or lymphotoxin with high affinity (Schoenfeld et al., 1991). TNF-β is a related lymphocyte product (TNF-α and TNF-β share 32% homology on the amino acid sequence level) that exhibits pleiotropic activities very similar to those of TNF-α. X-ray crystallographic analysis revealed that the tertiary structure of both molecules is virtually identical except that the TNF-β trimer creates a molecule that is less elongated than the TNF-α trimer and the latter has a top-region that flares open (Eck et al, 1992).

Besides the cell receptor interaction, TNF-α has been shown to have a lectin-like property for the oligosaccharide ligands chitobiose and Man(α1,3)-(Man(α1,6)-Man (Hession et al., 1987; Sherblom et al., 1988). They further demonstrated that the TNF-α protein has at least two different binding sites, one lectin-like and the other directed at cell surface receptors. Several TNF-α mutants were described for which the binding to the cellular TNF-receptor p55 and/or p75 was hampered. All these mutations are located in the lower half of the pyramidal structure of the biologically active TNF-α trimer (Van Ostade et al., 1991; Van Ostade et al., 1992; EP-A-0 486 908).

The availability of recombinant TNF has enhanced its use in tumor therapy. However, the in vivo tumoricidal effects of TNF-α have always been accompanied by toxic side effects. Different approaches were followed to overcome these noxious effects, including the use of monoclonal antibodies as well as fragments thereof, which neutralize the in vitro and in vivo toxic properties of TNF-α (e.g. EP-A-0 350 690).

In addition to its immunomodulating activity, TNF-α has also been shown to be involved in the control of growth and differentiation of various parasites. Upon infection of the host, parasites are capable of inducing the secretion of different cytokines such as TNF which may affect the course of the disease. For instance, in the case of malaria, TNF-α can be protective in certain circumstances, such as inhibiting parasite survival in rodent malaria (Clark et al., 1987; Taverne et al., 1987). By contrast, its overproduction can be detrimental to the host and can contribute to the pathology of the disease (Clark, 1987; Grau et al., 1989).

In schistosomiasis, the parasite uses the host-derived immunoregulatory protein TNF-α as a signal for replication and transmission (Amiri et al., 1992). Moreover, the authors found that the parasite worms required TNF-α for egg laying and for excretion of eggs from the host. In cutaneous leishmaniasis, TNF-α a plays a protective role (Titus et al., 1989; Liew et al., 1990).

African trypanosome species are the etiological agents for African trypanosomiasis, or sleeping sickness, and are a major cause of both human disease (*Trypanosoma brucei rhodesiense* and *T. brucei gambiense*) and cattle disease (*T. brucei brucei, T. evansi, T. vivax, T. congolense*) in Africa. Injected into their mammalian hosts by tsetse flies, trypanosomes remain extracellular bloodstream trypomastigotes throughout their mammalian phase. In trypanosomiasis, it has been shown that rabbits infected with *Trypanosoma brucei brucei* developed cachexia and suppression of lipoprotein lipase levels (Rouzer and Cerami, 1980). These parameters are indicators of TNF-α bioactivity (Beutler et al., 1985), thus suggesting that the parasite infection induced TNF in vivo. Kongshavn et al. (1988) reported that TNF-α inhibited the growth of in vitro cultures of *Trypanosoma musculi*, but administration of TNF-α in vivo during the course of infection led to a net increase in parasite development. The in vitro data indicate that a direct interaction between TNF-α and *T. musculi* can take place. All these experiments point to a direct interaction between host-derived TNF-α and parasites influencing the course and the outcome of parasitemia.

Considerable evidence implicates TNF-α is the principle mediator of endotoxic or septic shock (Cerami and Beutler, 1988). The intravenous injection of LPS (or endotoxin) in animals produces several parameters of the septic shock syndrome, namely, hypotension, decreased systemic vascular resistance, leukopenia, thrombocytopenia, and tissue dammage. In experimental animals, TNF-α produces hypotension, leukopenia, and local tissue necrosis (Okusawa et al., 1988). Administration of anti-TNF-α antibodies to baboons (Tracey et al., 1987) or rabbits prevents the shock induced by endotoxin (Mathison et al., 1988).

The term "TNF-induced septic shock" refers to the shock that develops in the presence of severe infection, especially following bacteremia with Gram-negative bacteria and release of endotoxin. It may also be caused by any class of microorganism, including Gram-positive bacteria, viruses, fungi, protozoa, spirochetes and rickettsiae. The pathophysiology of septic shock is very complex (see Harrison's Principles of Internal Medicine, 12th ed, McGraw-Hill, New York, pp. 502–507). Death is caused by progression to multiple organ failure and circulatory collapse.

Sherblom et al., (1988) have shown that the TNF-α has a lectin-like affinity for the glycoprotein uromodulin. Interestingly, this glycoprotein is able to potently inhibit the TNF-induced shock in vivo, whereas it does not block the tumoricidal activity of TNF-α on L929 cells in vitro. The authors suggested therefore that the lectin-like region of TNF-α is implicated in the toxic effects of TNF-α in septic shock, but not in its tumoricidal activity.

SUMMARY OF THE INVENTION

The aim of the present invention is to provide TNF-α muteins which have altered lectin-like properties in comparison with those of TNF-α, and/or TNF-α muteins which have a reduced toxic activity in comparison to TNF-α, and/or TNF-α muteins which have altered inflammatory cytokines inducing capacities with respect to TNF-α, and/or TNF-α muteins with reduced metastasis promoting activities with respect to TNF-α, and/or TNF-α muteins which have an extended half-life time with respect to TNF-α.

The aim of the present invention is to provide TNF-α muteins which have reduced lectin-like properties in comparison with those of TNF-α, and/or result in reduced cachexia or septic shock upon treatment with toxic concentrations of TNF-α in cytokine therapy, without having lost,their tumoricidal activity.

Another aim of the present invention is to provide pharmaceutical compositions comprising said TNF-α muteins.

The aim of the present invention is also to provide antisense peptides or antibodies which recognize the TNF-α lectin-like epitope for use in the preparation of a medicament for treating endogenous toxic concentrations of TNF-α due to sepsis, septic shock, Gram negative sepsis, endotoxic shock, toxic shock syndrome, cachexia, microbial infections, rheumatoid arthritis, inflammatory conditions, respiratory distress syndrome, pulmonary fibrosis, infections, graft-versus-host-disease, reperfusion damage such as myocardial ischaemia, AIDS, cancer, cerebral malaria, immunosuppression, etc.

Another aim of the present invention is to use said antibodies or said antisense peptides, in addition to complete TNF-α, for the preparation of a medicament for treating tumors, with said medicament having reduced toxic side effects and/or altered (i.e. reduced or increased) lectin-like effects and/or altered inflammatory cytokines inducing capacities, and/or altered adhesion molecules inducing capacities, and/or an increased half-life with respect to TNF-α in the absence of said antibodies or antisense peptides.

The present invention relates more particularly to a tumor necrosis factor mutein characterized in that the TNF-α amino acid sequence is mutated, or deleted totally or partially, in the region extending from amino acid position at 101 to 116 in such a way that:

either the lectin-like activities are modulated with respect to TNF-α, and/or the toxic activity is reduced with respect to TNF-α, and/or the inflammatory cytokines inducing capacities are modulated with respect to TNF-α, and/or the adhesion molecules inducing capacities are modulated with respect to TNF-α, and/or the metastasis promoting activity is reduced with respect to TNF-α, and/or the half life time is increased with respect to TNF-α, and providing that these TNF-α muteins have preferentially retained the tumoricidal activity of TNF-α, and providing that said TNF muteins are different from human TNF-α wherein amino acids 1 to 8 are replaced by a sequence within the region spanning amino acids 5 to 30 of laminin, and providing that said TNF muteins are different from human TNF-α wherein amino acid position 101 is Ser, hTNF-α wherein amino acid position 102 is Arg or deleted, hTNF-α wherein amino acid position 103 is Trp, hTNF-α wherein amino acid position 105 is Pro, hTNF-α wherein amino acid position 105 is Ile, hTNF-α wherein amino acid position 105 is Ile and position 44 is Cys, hTNF-α wherein amino acid position 106 is Ser, hTNF-α wherein amino acid position 106 is Ser and position 131 is Cys, hTNF-α wherein amino acid position 108 is Phe, hTNF-α wherein amino acid position 110 is Lys, hTNF-α wherein amino acid positions 111 to 112 are deleted, hTNF-α wherein amino acid position 112 is deleted or Met, hTNF-α wherein amino acid position 111 is deleted and amino acid positions 109 and 120 are respectively Gln and His, hTNF-α wherein amino acid position 115 is Ile or Cys, hTNF-α wherein amino acid position 116 is Lys, His or Val, hTNF-α wherein amino acid positions 115–116 are Ile-Lys;

and with said TNF muteins possibly containing in their peptidic chain outside the region spanning amino acids 101 to 116 of TNF-α, additional modifications consisting of substitutions and/or deletions and/or additions of one or several amino acid residues, and with said muteins being characterized in that they have retained the aforementioned activities; or a pharmaceutically acceptable salt thereof.

It is to be understood that the TNF-α muteins according to the present invention are characterized in that they have at least one of the following effects:

lectin-like activities which are modulated (i.e. reduced or increased), preferably reduced, from 5 to 100%, preferably at least 25%, more preferably at least 50%, most preferably at least 75%, as compared with lectin-like activities observed for TNF-α; or, a toxic effect which is reduced from 5 to 50%, preferably at least 10%, more preferably at least 25%, most preferably at least 35% as compared with the toxic effect of TNF-α; or, inflammatory cytokines inducing capacities which are modulated (i.e. either reduced or increased), preferably reduced, from 5 to 100%, preferably at least 25%, more preferably at least 50%, most preferably at least 75% with respect to TNF-α; or, adhesion molecules inducing capacities which are modulated (i.e. either reduced or increased), preferably reduced, from 5 to 100%, preferably at least 25%, more preferably at least 50%, most preferably at least 75% with respect to TNF-α; or, a metastasis promoting activity which is reduced from 5 to 100%, preferably at least 25%, more preferably at least 50%, most preferably at least 75% with respect to TNF-α; or, a half life time that is increased from 5 to 100%, preferably at least 25%, more preferably at least 50%, most preferably at least 75% with respect to TNF-α; or, the tumoricidal activity of TNF-α being preferentially retained by said muteins.

The tumoricidal activity is considered to be retained within the meaning of the present invention when said TNF-α muteins have a tumoricidal activity of at least 75%, preferably at least 85%, more preferably at least 95% and even more preferably at least 100% of the tumoricidal activity of TNF-α which has not been mutated in the region spanning amino acids 101 to 116. It is, however, also possible that TNF-muteins according to the present invention have largely lost the tumoricidal activities of TNF-α, whilst in addition having at least one, or preferably a combination, of any of the aforementioned activities of the TNF muteins according to the invention which are modulated (i.e. increased or reduced). For instance, TNF-muteins which have increased lectin-like activities and/or a reduced toxicity, and/or a reduced metastasis promoting activity, and/or an extended half life, and which can no longer be classified as having a tumoricidal activity are also contemplated within the present invention.

It is also to be understood that the TNF-muteins according to the present invention will mostly show a combination of at least two of the aforementioned effects. Illustrations of preferred TNF-muteins according to the present invention are given below and in the Examples section.

The term "toxic activity" refers to the in vivo TNF- or LPS-induced septic shock effect of TNF-α as explained above, and may be measured in vivo on the basis of the increased survival time of C57BL/6 mice, upon injection with fixed dosages of the TNF-α mutein, as compared with that in C57BL/6 mice injected with the same dosages of unmodified TNF-α; or by any other technique known in the art.

The term "tumoricidal activity" refers to the in vivo tumor cell killing activity of TNF-α, which may be measured by means of any assay comprised in the art. The term "cytotoxic or cytolytical activity" refers to the in vitro tumor cell killing activity of TNF-α. In the Examples section of this application an in vitro assay is reported to measure the cytotoxic activity of TNF-α on L929 TNF-sensitive fibrosarcoma cells. An in vivo assay to evaluate the tumoricidal activity of TNF-α on HT-29 tumors in nude mice, and by means of the B16B16 melanoma test system, are also reported in the Examples section.

The term "lectin-like activities" of the present invention refers to the lectin-like properties of TNF-α. The lectin-like properties of TNF-α are for instance those described by Hession et al. (1988) and Sherblom et al. (1988) and include any biological effect mediated by any lectin-carbohydrate interaction located in the region extending from amino acids 101 to 116 of TNF-α. The "lectin-like activities" of the TNF-α muteins of the invention may be measured as the percentage of inhibition of trypanocidal activity of the TNF mutein, upon prior incubation of said TNF mutein with the oligosaccharide sugar N,N'-diacetylchitobiose as described in the Examples section; or by means of any other assay comprised in the art.

The term "trypanocidal activity" refers to the trypanocidal activity of TNF-α located in the region extending from amino acid positions 101 to 116 of TNF-α may be measured by means of an in vitro or an in vivo trypanocidal activity assay as extensively explained in the Examples section.

The term "inflammatory cytokines inducing capacities" of TNFA within the meaning of the present invention refers to the stimulation capacity of TNF-α of cytokines such as IL1α, IL1β, IL8, TNF, IL6 and other molecules known to have a role in inflammatory processes by endothelial cells, said capacities being located in the region extending from amino acids 101 to 116 of TNF-α.

The term "adhesion molecules inducing capacities" of TNFα within the meaning of the present invention refers to the stimulation of adhesion molecules capacity of TNFα, such as the stimulation of ICAM-1, ICAM-2, ECAM-1 (E-selectin), P-selectin, Endoglin, VCAM-1, VLA Integrin (β1-integrin family), CD36, CD9, CD31, GlyCAM-1, which mediate adhesion events necessary to mount inflammatory reactions, said capacities being located within the region extending from amino acid positions 101 to 116 of TNFα.

The term "metastasis promoting activity" within the meaning of the present invention refers to negative in vivo side effects of TNF-α exerted against tumor cells and resulting in a net increase/growth of the number of metastase such as reviewed by Orosz et al., 1993, located within the region extending from amino acid positions 101 to 116 of TNFα.

The term "half-life" refers to the in vivo measured time during which the TNF-α muteins of the invention remain in circulation and are detectable in body fluids.

The inhibition/stimulation of these TNF-α muteins on the inflammatory cytokines inducing capacities of TNFα may be measured in vivo by any technique known in the art, more particularly any of the techniques disclosed in the examples section of the present invention.

The inhibition/stimulation of these TNF-α muteins on the adhesion molecules inducing capacities of TNF-α may be measured in vivo by any technique known in the art.

The inhibition of metastasis promoting activity by these TNF-α muteins may be measured in vivo by any technique known in the art, or as disclosed in the examples section.

The increase of the half life time by these TNF-α muteins may be measured in vivo by any technique known in the art, or as disclosed in the examples section.

The term "TNF-α" refers to polypeptides of human origin containing 157 amino acid residues, as disclosed by Pennica et al. (1984), namely (SEQ ID NO: 35):

```
                5                  10                 15
  1  Val Arg Ser Ser Ser Arg Thr Pro Ser Asp Lys Pro Val Ala His
 16  Val Val Ala Asn Pro Gln Ala Glu Gly Gln Leu Gln Trp Leu Asn
 31  Arg Arg Ala Asn Ala Leu Leu Ala Asn Gly Val Glu Leu Arg Asp
 46  Asn Gln Leu Val Val Pro Ser Glu Gly Leu Tyr Leu Ile Tyr Ser
 61  Gln Val Leu Phe Lys Gly Gln Gly Cys Pro Ser Thr His Val Leu
 76  Leu Thr His Thr Ile Ser Arg Ile Ala Val Ser Tyr Gln Thr Lys
 91  Val Asn Leu Leu Ser Ala Ile Lys Ser Pro Cys Gln Arg Glu Thr
106  Pro Glu Gly Ala Glu Ala Lys Pro Trp Tyr Glu Pro Ile Tyr Leu
121  Gly Gly Val Phe Gln Leu Glu Lys Gly Asp Arg Leu Ser Ala Glu
136  Ile Asn Arg Pro Asp Tyr Leu Asp Phe Ala Glu Ser Gly Gln Val
151  Tyr Phe Gly Ile Ile Ala Leu
``` or as disclosed by Marmenout et al. (1985), or by Wang et al. (1985), or Shirai et al. (1985).

The term "TNF-α" of the present invention also refers to polypeptides of mouse origin containing 156 amino acid residues, disclosed by Fransen et al. (1985) namely (SEQ ID NO: 36):

```
                5                  10                 15
  1  Leu Arg Ser Ser Ser Gln Asn Ser Ser Asp Lys Pro Val Ala His
 16  Val Val Ala Asn His Gln Val Glu Glu Gln Leu Glu Trp Leu Ser
 31  Gln Arg Ala Asn Ala Leu Leu Ala Asn Gly Met Asp Leu Lys Asp
 46  Asn Gln Leu Val Val Pro Ala Asp Gly Leu Tyr Leu Val Tyr Ser
 61  Gln Val Leu Phe Lys Gly Gln Gly Cys Pro Asp Tyr — Val Leu
 76  Leu Thr His Thr Val Ser Arg Phe Ala Ile Ser Tyr Gln Glu Lys
 91  Val Asn Leu Leu Ser Ala Val Lys Ser Pro Cys Pro Lys Asp Thr
106  Pro Glu Gly Ala Glu Leu Lys Pro Trp Tyr Glu Pro Ile Tyr Leu
121  Gly Gly Val Phe Gln Leu Glu Lys Gly Asp Gln Leu Ser Ala Glu
136  Val Asn Leu Pro Lys Tyr Leu Asp Phe Ala Glu Ser Gly Gln Val
151  Tyr Phe Gly Val Ile Ala Leu
``` or as disclosed by Pennica et al. (1985), which at least contain the peptide sequence Thr Pro Glu Gly Ala Glu (SEQ ID NO 23) in peptidic chain.

The expression "TNF-α amino acid sequence which is mutated in the region extending from amino acid position 101 to 116" refers to either deletions, insertions and/or substitutions in the region of amino acid positions 101 to 116 of TNF-α (including both positions 101 and 116). It is to be understood that the result of all of these deletions is such that at least one of the effects mentioned-above, and preferably combinations of at least two such effects of TNF-α, ascribed to the region covering amino acid positions 101 to 116 of TNF-α, are modulated and by preference are strongly reduced or abolished in the case of life-threatening lectin-like effects (toxic effect, inflammatory cytokines inducing activities, adhesion molecules inducing activities), metastasis promoting effects of TNF-α, or are by preference increased in the case of half-life times and beneficial lectin-like activities (such as induction of cytokines or adhesion molecules which are beneficial to the envisaged treatment).

For TNF-β, the above described septic shock or cachexia effects are not found. The term "TNF-β" refers to tumor necrosis factor β or lymphotoxin (Gray, 1987). TNF-β and TNF-α are members of a duplicated gene family which show 30 to 32% homology at the amino acid level and share many biological activities, including the tumoricidal activity against L929 cells. Despite the fact that both cytokines share the same cell-surface receptor (Aggarwal et al., 1985), important differences exist between TNF-α and TNF-β, both with regard to protein sequence and gene regulation. There are also distinct differences in the mode of secretion in that TNF-α is a membrane protein (Kriegler et al., 1988), whereas TNF-β is a secreted protein.

Table I gives an overview of the amino acid substitutions which could be the basis of some of the additional modifications in the TNF-α muteins in the region outside the region extending from amino acid positions 101 to 116 as defined above.

TABLE I

| Amino acids | Synonymous groups |
| --- | --- |
| Ser | Ser, Thr, Gly, Asn |
| Arg | Arg, His, Lys, Glu, Gln |
| Leu | Leu, Ile, Met, Phe, Val, Tyr |
| Pro | Pro, Ala, Thr, Gly |
| Thr | Thr, Pro, Ser, Ala, Gly, His, Gln |
| Ala | Ala, Pro, Gly, Thr |
| Val | Val, Met, Ile, Tyr, Phe, Leu, Val |
| Gly | Gly, Ala, Thr, Pro, Ser |
| Ile | Ile, Met, Leu, Phe, Val, Ile, Tyr |
| Phe | Phe, Met, Tyr, Ile, Leu, Trp, Val |
| Tyr | Tyr, Phe, Trp, Met, Ile, Val, Leu |
| Cys | Cys, Ser, Thr |
| His | His, Gln, Arg, Lys, Glu, Thr |
| Gln | Gln, Glu, His, Lys, Asn, Thr, Arg |
| Asn | Asn, Asp, Ser, Gln |
| Lys | Lys, Arg, Glu, Gln, His |
| Asp | Asp, Asn, Glu |
| Glu | Glu, Gln, Asp, Lys, Asn, His, Arg |
| Met | Met, Ile, Leu, Phe, Val |

It is reported in the example section of the present invention that TNF-α-derived synthetic peptides located in the region extending from amino acid positions 101 to 116 of TNF-α as indicated in the sequences above, and which will be further referred to as the "TNF-α tip peptides", and which can be represented by the following general formula:

(Y1-Y2-Y3)$_n$-Thr-X1-Glu-X2-X3-Glu-(Y4-Lys-Pro-Trp-Tyr)$_n$(SEQ ID NO: 1), wherein, n represents 0 or 1, X1 can represent Pro, Ala, Thr, or Gly;

X2 can represent Gly, Ala, Thr, Pro, or Ser;

X3 can represent Ala, Pro, Gly, or Thr;

Y1 can represent Pro or Gln;

Y2 can represent Lys or Arg;

Y3 can represent Asp or Glu;

and, Y4 can represent Leu or Ala have a direct trypanocidal activity against the pleomorphic bloodstream forms of the African trypanosomes *Trypanosoma brucei brucei* and *Trypanosoma brucei rhodesiense*.

It is to be understood that the TNF-α amino acid position numbering in the present application refers to the numbering as given in the sequences above. In this respect, it is to be noted that the region covering amino acids 101 to 116 of human TNF-α corresponds to amino acids 100 to 115 of mouse TNF-α, since in the sequences given above, a space has been introduced in the mouse TNF-α amino acid sequence position 73 in order to align it with the human TNF-α amino acid sequence.

Moreover, it is shown in the examples section that the trypanocidal activity of the TNF-α "tip-region" can be inhibited by preincubation with N,N'-diacetylchitobiose, for which TNF-α has a lectin-like activity (Hession et al., 1987; Sherblom et al., 1988). Therefore, the tip region of TNF-α is shown to be implicated in the lectin-like activities of the cytokine. Since the glycoprotein uromodulin, which binds TNF-α via its lectin-like domain, can inhibit lipopolysaccharide (LPS)-induced septic shock, caused by TNF-α, but can not inhibit the TNF-α tumoricidal effect on L929 cells, the lectin-like region of TNF-α, and consequently the tip-region of TNF-α, are shown by the present inventors to be implicated in the toxic side effects of the cytokine in vivo.

Consequently, as illustrated in the examples section of the present invention, TNF-α muteins (extending from positions 101 to 116 of TNF-α) were constructed in the tip-region which are characterized in that either the lectin-like activities are reduced with respect to TNF-α, or the toxic activity is reduced with respect to TNF-α; or the half life is increased with respect to TNF-α; or the metastasis promoting activities are reduced with respect to TNF-α, or the inflammatory cytokines inducing capacities are reduced with respect to TNF-α, or a combination of these effects are reduced/increased with respect to TNF-α and with said muteins being further characterized in that they have not lost the tumoricidal activity of TNF-α; as detailed above.

Consequently the present invention relates more particularly to a TNF mutein as defined above, further characterized in that the lectin-like activities are modulated with respect to TNF-α.

According to a preferred embodiment, the present invention relates to a TNF mutein as defined above, further characterized in that the lectin-like activities are reduced with respect to TNF-α.

It is extensively illustrated in the examples section of the present invention that the region spanning amino acids 101 to 116, and more particularly 105 to 110, is involved not only in the trypanocidal but also in the lectin-like activities of TNF-α. The lectin-like activities were measured indirectly via the inhibition of the trypanocidal activity of TNF-α.

According to a possible embodiment, the present invention also relates to a TNF mutein as defined above, further characterized in that the lectin-like activities are increased with respect to TNF-α. TNF muteins having increased lectin-like activities may be beneficial to certain envisaged treatments.

According to another preferred embodiment, the present invention relates to a TNF mutein as defined above, further characterized in that the toxic activity is reduced with respect to TNF-α. It is illustrated in the examples section of the present invention that mutations to an Ala at positions T(105), E(107) and/or E(110) and a deletion of the region extending from amino acids 105 to 110 of mTNFα leads to mTNF-α muteins with a lower LD50 value as measured in vivo.

According to yet another embodiment, the present invention relates to a TNF mutein as defined above, further characterized in that the inflammatory cytokine inducing capacities are modulated with respect to TNF-α.

According to a preferred embodiment, the present invention relates to a TNF mutein as defined above, further characterized in that the inflammatory cytokine inducing capacities are increased with respect to TNF-α. As shown in the examples section of the present invention, mTNF-α muteins bearing a deletion of the region spanning amino acids 105–110 of mTNF-α show a higher induction of human interleukin-6 on human microvascular endothelial cells of the brain in vivo than wild-type mTNFα.

According to another possible embodiment, the present invention relates to a TNF mutein as defined above, further characterized in that the inflammatory cytokine inducing capacities are reduced with respect to TNF-α. It is shown in the examples section that T(105)A and P(106)A mTNF-α muteins as well a deletion mutant of mTNFα in the region extending from amino acids 105 to 110 induce consistently less human interleukin 8 (IL8) than wild-type TNF-α on human endothelial cells as measured in vivo.

According to yet another embodiment, the present invention relates to a TNF mutein as defined above, further characterized in that the adhesion molecule inducing capacities are modulated with respect to TNF-α.

According to another preferred embodiment, the present invention relates to a TNF mutein as defined above, further characterized in that the adhesion molecule inducing capacities are reduced with respect to TNF-α.

According to another possible embodiment, the present invention refers to a TNF mutein as defined above, further characterized in that the adhesion molecule inducing capacities are increased with respect to TNF-α.

According to yet another preferred embodiment, the present invention relates to a TNF mutein as defined above, further characterized in that the metastasis promoting activity is reduced with respect to TNF-α. As illustrated in the examples section, a mTNFα mutein carrying a deletion of the region extending from amino acids 105 to 110 shows a considerably lower in vivo metastasis enhancing potential compared to wild-type mTNFα in a murine lung carcinoma cell line model.

According to a preferred embodiment, the present invention relates to a TNF mutein having at least one of the aforementioned effects, further characterized in that the tumoricidal activity is retained with respect to TNF-α. As shown in the examples section, all up till now constructed mTNFα muteins have retained their tumoricidal activity in comparison to wild-type mouse TNFα.

According to yet another possible embodiment of the present invention, any of the TNF muteins having at least one of the effects as defined above are further characterized in that their tumoricidal activity is reduced with respect to TNF-α.

In view of possible treatments with the TNF-α muteins on the basis of their altered lectin-like, or inflammatory cytokines inducing, or adhesion molecules inducing properties, the loss of the tumoricidal effect by certain TNF muteins of the invention may be desirable.

According to yet another preferred embodiment, the present invention relates to a TNF mutein as defined above, further characterized in it shows an increased half life time with respect to TNF-α. As shown in the examples section, the tip deleted (amino acids 105–110) mTNFα muteins shows an increased half life as measured by means of the L929 cytotoxic assay and the indirect ELISA compared to wild-type mTNFα.

According to a preferred embodiment, the present invention relates to any TNF mutein as defined above, characterized in that at least part of the region extending from amino acid positions 101 to 116 of TNF-α, or the complete region corresponding to amino acid positions 101 to 116 of TNF-α has been deleted, and preferably at least the region covering amino acid positions 105 to 110 has been deleted.

According to the latter preferred embodiment said TNF muteins should be different from human TNF-α wherein amino acids 1 to 8 are replaced by a sequence within the region spanning amino acids 5 to 30 of laminin, and providing that said TNF muteins are different from human TNF-α wherein amino acid position 105 is Pro, hTNF-α wherein amino acid position 105 is Ile, hTNF-α wherein amino acid position 105 is Ile and position 44 is Cys, hTNF-α wherein amino acid position 106 is Ser, hTNF-α wherein amino acid position 106 is Ser and position 131 is Cys, hTNF-α wherein amino acid position 108 is Phe, hTNF-α wherein amino acid position 110 is Lys, and hTNF-α wherein amino acid positions 109 and 120 are respectively Gln and His and amino acid 111 is deleted, and may contain substitutions as set out in Table 1, in the region of TNF-α outside the region spanning from amino acid position 105 to amino acid position 110.

According to a preferred embodiment, the present invention relates to a TNF mutein according to as defined above, characterized in that at least one of the amino acids in the region extending from amino acids 101 to 116 of TNF-α has been mutated or deleted more particulary at least one of the amino acids in the region extending from amino acids 105 to 110.

According to a particular embodiment, the present invention relates to TNF muteins wherein the region between amino acid positions 101 and 116 has been mutated in such a way that the amino acids Thr(105), Glu(107) and/or Glu(110) have been mutated to an Alanine residue, as demonstrated in the examples section. Although the examples given relate to mouse TNF-α muteins, also human TNF-α muteins are contemplated within the present invention.

According to yet another embodiment, the present invention relates to a nucleic acid sequence encoding any of the TNF mutein polypeptides as defined above.

According to yet another embodiment, the present invention relates to a process for the preparation of the TNF mutein polypeptides as defined above, comprising the steps of:

transformation of an appropriate cellular host with a vector, particularly a plasmid, a cosmid, a phage or a virus, in which a nucleic acid sequence as defined above coding for at least one of the TNF mutein polypeptides as defined above has been inserted (insert) under the control of the appropriate regulatory elements, particularly a promoter recognized by the polymerases of the cellular host and, in the case of a procaryotic host, an appropriate ribosome binding site (RBS), enabling the expression in said cellular host of said nucleic acid sequence, culture of said transformed cellular host under conditions enabling the expression of said insert.

The polypeptides according to the present invention can be prepared via recombinant DNA technology. In order to carry out the expression of the polypeptides of the invention in bacteria such as *E. coli* or in an eukaryotic cell such as *Saccharomyces cerevisiae*, or in cultured vertebrate or invertebrate hosts such as insect cells, Chinese Hamster Ovary (CHO), COS1, BHK, and MDCK.

The polypeptides prepared according to this process of the invention will normally contain only naturally occuring L-amino acids. If required, D-amino acids can be incorporated into the polypeptides of the invention according to any technique known in the art, provided their incorporation into said peptides does not interfere with the lectin-like, or toxic, or tumoricidal properties of the TNF muteins according to the invention.

The present invention relates also to TNF muteins characterized in that the TNF-α amino acid sequence is mutated, or deleted totally or partially, in the region extending from amino acid position at 101 to 116 in such a way that:

either the lectin-like activities are modulated with respect to TNF-α, and/or the toxic activity is reduced with respect to TNF-α, and/or the inflammatory cytokines inducing capacities are modulated with respect to TNf-α, and/or the adhesion molecules inducing capacities are modulated with respect to TNF-α, and/or the metastasis promoting activity is reduced with respect to TNF-α, and/or show an increased half life time with respect to TNF-α, and providing that these TNF-α muteins have preferentially retained the tumoricidal activity of TNF-α, and with said TNF muteins possibly containing in their peptidic chain outside amino acid region 101 to 116 of TNF-α, additional modifications consisting of substitutions and/or deletions and/or additions of one or several amino acid residues, and with said muteins being characterized in that they have retained the aforementioned activities; or a pharmaceutically acceptable salt thereof, for treating illnesses and pathological conditions, such as sepsis, septic shock, Gram negative sepsis, endotoxic shock, toxic shock syndrome, cachexia, microbial infections, rheumatoid arthritis, inflammatory conditions, respiratory distress syndrome, pulmonary fibrosis, infections, graft-versus-host-disease, reperfusion damage such as myocardial ischaemia, AIDS, cancer, immunosuppression, cerebral malaria, etc.

It is to be understood that the TNF-α muteins according to the present invention may advantageously be used for the fact that they have a tumoricidal activity, while they lack either the life-threatening toxic, or the lectin-like properties of TNF-α, or the metastasis promoting effects of TNF-α, or the inflammation cytokines inducing capacities of TNF-α or mixture of these effects, and/or because they have an increased half life compared to TNF-α, and/or because they have increased beneficial lectin-like activities and/or inflammatory cytokines inducing activities, and/or ashesion molecules inducing activities compared to TNF-α.

According to an advantageous embodiment, said muteins for treating the above-specified illnesses are preferentially different from from human TNF-α wherein amino acids 1 to 8 are replaced by a sequence within the region spanning amino acids 5 to 30 of laminin, and providing that said TNF muteins are preferentially different from human TNF-α wherein: amino acid position 101 is Ser, hTNF-α wherein amino acid position 102 is Arg or deleted, hTNF-α wherein amino acid position 103 is Trp, hTNF-α wherein amino acid position 105 is Pro, hTNF-α wherein amino acid position 105 is Ile, hTNF-α wherein hTNF-α amino acid position 105 is Ile and position 44 is Cys, hTNF-α wherein amino acid position 106 is Ser, hTNF-α wherein amino acid position 106 is Ser and position 131 is Cys, hTNF-α wherein amino acid position 108 is Phe, hTNF-α wherein amino acid position 110 is Lys, hTNF-α wherein amino acid positions 111 to 112 are deleted, hTNF-α wherein amino acid position 112 is deleted or Met, hTNF-α wherein amino acid position 111 is deleted and amino acid positions 109 and 120 are respectively Gln and His, hTNF-α wherein amino acid position 115 is Ile or Cys, hTNF-α wherein amino acid position 116 is Lys, His or Val, hTNF-α wherein amino acid positions 115–116 are Ile-Lys.

According to yet another advantageous embodiment of the present invention, the TNF muteins used for treating the above-specified illnesses contain either a mutation of one or more amino acids or a deletion of at least part of the region spanning amino acids 105 to 110 of TNF-α. Particularly preferred examples as well as their biological effects are discussed in the examples section.

According to a preferred embodiment, the present invention relates to a pharmaceutical composition, containing, as active substance, at least anyone of the TNF muteins as defined above, in association with a pharmaceutical acceptable vehicle.

The mode of administration of these pharmaceutical compositions is enteral or preferably parenteral, i.e., intravenous, intraperitoneal, intramuscular, or subcutaneous, with the intravenous route being preferred.

The active substances of these pharmaceutical compositions may be administered alone, without a carrier vehicle; however, they may also be administered with pharmaceutically acceptable non-toxic carriers or diluents, the proportions of which are determined by the suitability and chemical nature of the particular carrier.

According to an advantageous embodiment, the above-mentioned pharmaceutical compositions contain muteins which are preferably different from human TNF-α wherein: amino acids 1 to 8 are replaced by a sequence within the region spanning amino acids 5 to 30 of laminin, and providing that said TNF muteins are different from human TNF-α wherein amino acid position 101 is Ser, hTNF-α wherein amino acid position 102 is Arg or deleted, hTNF-α wherein amino acid position 103 is Trp, hTNF-α wherein amino acid position 105 is Pro, hTNF-α wherein amino acid position 105 is Ile, hTNF-α wherein amino acid position 105 is Ile and position 44 is Cys, hTNF-α wherein amino acid position 106 is Ser, hTNF-α wherein amino acid position 106 is Ser and position 131 is Cys, hTNF-α wherein amino acid position 108 is Phe, hTNF-α wherein amino acid position 110 is Lys, hTNF-α wherein amino acid positions 111 to 112 are deleted, hTNF-α wherein amino acid position 112 is deleted or Met, hTNF-α wherein amino acid position 111 is deleted and amino acid positions 109 and 120 are respectively Gln and His, hTNF-α wherein amino acid position 115 is Ile or Cys, hTNF-α wherein amino acid position 116 is Lys, His or Val, hTNF-α wherein amino acid positions 115–116 are Ile-Lys.

According to an advantageous embodiment, the above-mentioned pharmaceutical compositions contain muteins which can be human TNF-α wherein: amino acids 1 to 8 are replaced by a sequence within the region spanning amino acids 5 to 30 of laminin, and providing that said TNF muteins are different from human TNF-α wherein amino acid position 101 is Ser, hTNF-α wherein amino acid position 102 is Arg or deleted, hTNF-α wherein amino acid position 103 is Trp, hTNF-α wherein amino acid position 105 is Pro, hTNF-α wherein amino acid position 105 is Ile, hTNF-α wherein amino acid position 105 is Ile and position 44 is Cys, hTNF-α wherein amino acid position 106 is Ser, hTNF-α wherein amino acid position 106 is Ser and position 131 is Cys, hTNF-α wherein amino acid position 108 is Phe, hTNF-α wherein amino acid position 110 is Lys, hTNF-α wherein amino acid positions 111 to 112 are deleted, hTNF-α wherein amino acid position 112 is deleted or Met, hTNF-α wherein amino acid position 111 is deleted and amino acid positions 109 and 120 are respectively Gln and His, hTNF-α wherein amino acid position 115 is Ile or Cys, hTNF-α wherein amino acid position 116 is Lys, His or Val, hTNF-α wherein amino acid positions 115–116 are Ile-Lys.

According to yet another advantageous embodiment of the present invention, the TNF muteins used for treating the above-specified illnesses contain either a mutation of one or more amino acids or a deletion of at least part of the region spanning amino acids 105 to 110 of TNF-α. Particularly preferred examples as well as their biological effects are discussed in the examples section.

The present invention relates also to the use of a TNF mutein characterized in that the TNF-α amino acid sequence is mutated, or deleted totally or partially, in the region extending from amino acid position at 101 to 116, more particularly in the region extending from amino acid positions 105 to 110, in such a way that:

either the lectin-like activities are modulated with respect to TNF-α, and/or the toxic activity is reduced with respect to TNF-α, and/or the inflammatory cytokines inducing capacities are modulated with respect to TNf-α, and/or the adhesion molecules inducing capacities are modulated with respect to TNF-α, and/or the metastasis promoting activity is reduced with respect to TNF-α, and/or show an increased half life time with respect to TNF-α, and providing that these TNF-α muteins have preferentially retained the tumoricidal activity of TNF-α, and with said TNF muteins possibly containing in their peptidic chain outside amino acid region 101 to 116 (or respectively 105 to 110) of TNF-α, additional modifications consisting of substitutions and/or deletions and/or additions of one or several amino acid residues, and with said muteins being characterized in that they have retained the aforementioned activities; or a pharmaceutically acceptable salt thereof, for the preparation of a medicament for treating illnesses and pathological conditions, such as, sepsis, septic shock, Gram negative sepsis, endotoxic shock, toxic shock syndrome, cachexia, microbial infections, rheumatoid arthritis, inflammatory conditions, respiratory distress syndrome, pulmonary fibrosis, infections, graft-versus-host-disease, reperfusion damage such as myocardial ischaemia, AIDS, cancer, immunosuppression, cerebral malaria, etc.

It is to be understood that the TNF-α muteins according to the present invention may especially be used for the fact that they may have a tumoricidal activity, while they lack either the toxic, and/or the lectin-like properties of TNF-α, and/or the metastasis promoting effects of TNF-α, and/or the inflammatory cytokines inducing capacities of TNFα, and/or the adhesion molecules inducing capacities of TNFα, or mixture of these effects, and/or because they have an increased half life compared to TNF-α.

According to another embodiment, the present invention relates to the use of an antibody specifically detecting an epitope residing in the region encompassing amino acids 101 to 116 of TNF-α, preferably in the region encompassing amino acids 105 to 110 of TNFα more particularly a monoclonal antibody, characterized in that it:

either modulates the lectin-like activities of TNF-α, and/or inhibits the toxic activity of TNF-α, and/or modulates the inflammatory cytokines inducing capacities of TNf-α, and/or modulates the adhesion molecules inducing capacities of TNF-α, and/or inhibits the metastasis promoting activity of TNF-α, for the preparation of a medicament used for treating TNF-α-induced septic shock, or for treating any pathological condition associated with the in vivo lectin-like activities of TNF-α, such as for treating sepsis, septic shock, Gram negative sepsis, endotoxic shock, toxic shock syndrome, cachexia, microbial infections, rheumatoid arthritis, inflammatory conditions, respiratory distress syndrome, pulmonary fibrosis, infections, graft-versus-host-disease, reperfusion damage such as myocardial ischaemia, AIDS, cancer, immunosuppression, cerebral malaria, etc.

It is to be understood that the antibodies according to the present invention are characterized in that they have at least one of the following effects:

they modulate (i.e. inhibit or stimulate), preferably inhibit, the lectin-like effects of TNF-α preferentially from 5 to 100%, preferably at least 25%, more preferably at least with 50%, most preferably with at least 75%; or, they inhibit the toxic effect of TNF-α with from 5 to 50%, preferably at least 10%, more preferably with at least 25%, most preferably with at least 35%; or, they modulate (i.e. inhibit or stimulate), preferably inhibit, the inflammatory cytokines inducing capacities of TNF-α from 5 to 100%, preferably with at least 25%, more preferably with at least 50%, most preferably with at least 75%; or, they modulate (i.e. inhibit or stimulate), preferably inhibit, the adhesion molecules inducing capacities of TNF-α from 5 to 100%, preferably with at least 25%, more preferably with at least 50%, most preferably with at least 75%; or, they inhibit the metastasis promoting activity of TNF-α from 5 to 100%, preferably with at least 25%, more preferably with at least 50%, most preferably with at least 75% with respect to TNF-α.

The inhibition/stimulation of the lectin-like activities of TNF-α by the antibodies of the invention is measured as the percentage of inhibition of trypanocidal activity upon prior incubation of TNF-α with said antibody of the invention in the presence and/or absence of N,N'-diacetylchitobiose; or by any other method known in the art.

The inhibition of the toxic activity of TNF-α by the antibodies of the invention may be measured by the increase in survival time of Balb/C mice, upon treatment with LPS in the presence of different concentrations of the antibody of the invention, as illustrated in the Examples section.

The inhibition of the tumoricidal activity may be measured by means of any assay comprised in the art which measures this activity in vivo on TNF-sensitive tumor cells. In the example section of this application, an in vitro assay to measure the cytotoxic (cytolytic) activity of TNF-α on L929 TNF-sensitive fibrosarcoma cells is reported. An in vivo assay to evaluate the tumoricidal activity of TNF-α on HT-29 tumors in nude mice, and by means of the B16B16 melanoma test system, are also reported in the examples section.

The inhibition/stimulation of these antibodies on the inflammatory cytokines inducing capacities of TNFα may be measured in vivo by any technique known in the art, more particularly any of the techniques disclosed in the examples section of the present invention.

The inhibition/stimulation of these antibodies on the adhesion molecules inducing capacities of TNF-α may be measured in vivo by any technique known in the art.

The inhibition of metastasis promoting activity by these antibodies of TNF-α may be measured in vivo by any technique known in the art, or as disclosed in the examples section.

In order to assume inhibition of one or combinations of any of the mentioned effects in vivo, the monoclonal antibody of the invention should form an immunological complex with the subregion of the TNF-α "tip-region" responsible for either of the effects of TNF-α.

According to a preferred embodiment, the present invention relates to the use of an immunological complex, comprising a monoclonal antibody as defined above, and TNF-α, for the preparation of a medicament.

According to this embodiment of the invention, a pharmaceutical composition, containing, as active substance, an immunological complex comprising a monoclonal antibody as defined above, and complete TNF-α, in association with a pharmaceutical acceptable vehicle, is provided.

Instead of, or in addition to TNF-α, the above mentioned compositions could also contain IL-1α, IL-1β, IL-6, IFN-gamma, IFN α/β, IL-8, or any other immunoreactive agent.

The above-mentioned composition can be used for treating illnesses wherein a treatment with TNF-α is beneficial such as tumors.

Moreover, the above-mentioned composition may especially be used for the fact that it exterts a tumoricidal activity, while lacking either the toxic, and/or the lectin-like properties of TNF-α, and/or the metastasis promoting effects of TNF-α, and/or inflammatory cytokines inducing capacities, and/or adhesion molecules inducing capacities, or mixture of these effects, and/or because they have an increased half life compared to TNF-α. Therefore, they are ideally suited for treating tumors or cancers.

The antibodies according to this embodiment of the invention may include polyclonal or monoclonal antibodies.

The monoclonal antibodies of the invention can be produced by any hybridoma liable to be formed according to classical methods from splenic cells of an animal, particularly of a mouse or rat, immunized against the polypeptides according to the invention, or muteins thereof, or fragments thereof defined above on the one hand, and of cells of a myeloma cell line on the other hand, and to be selected by the ability of the hybridoma to produce the monoclonal antibodies recognizing the polypeptides which has been initially used for the immunization of the animals.

The antibodies involved in the invention can be labelled by an appropriate label of the enzymatic, fluorescent, or radioactive type.

In the case of treatment of human illnesses, the monoclonal antibodies according to this preferred embodiment of the invention may be humanized versions of mouse monoclonal antibodies made by means of recombinant DNA technology, departing from parts of mouse and/or human genomic DNA sequences coding for H and L chains or from cDNA clones coding for H and L chains.

Alternatively the monoclonal antibodies according to this preferred embodiment of the invention may be human monoclonal antibodies. Such human monoclonal antibodies are prepared by EBV immortalization or, for instance, by means of human peripheral blood lymphocyte (PBL) repopulation of severe combined immune deficiency (SCID) mice (for recent review see Duchosal et al., 1992).

The invention also relates to the use of the peptides or polypeptides of the invention for the selection of recombinant antibodies by the process of repertoire cloning (Perrson et al., 1991).

Monoclonal antibodies can be characterized according to their subclass by known methods such as Ouchterlony immunodiffusion.

It is furthermore known in the art that monoclonal antibodies, or fragments thereof, can be modified for various uses, and fragments can be generated which retain the antigen binding properties. Such fragments are commonly generated by, for instance enzymatic digestion of the antibodies with papain, pepsin, or other proteases.

The peptides according to this embodiment of the invention may be circularized before immunization. The expression "circularized" refers to a joining of the N- and C-terminal cysteine residues by means of oxidation at low molar concentration to promote intramolecular disulfide bridges or by any other technique comprised in the art.

If desired, all above-mentioned peptides or polypeptides can be provided for with an extra N- and C-terminal cysteine residue, in order to circularize the peptide.

The peptides used for immunization are preferably in the form in which they are joined to a biotin molecule, or any other carrier molecule in order to achieve a good immunogenic response. As demonstrated in the Examples section, the biotin molecule may be coupled to the peptide of choice via a linker, such as Gly—Gly, or any other linker comprised in the art.

Furthermore, the peptides used for immunization preferentially contain only naturally occuring L-amino acids. If required, D-amino acids may be incorporated as long as the immunogenic, lectin-like, toxic and/or trypanocidal properties of the peptides have been retained.

The TNF-induced septic shock effect may be assayed by means of the increase of the survival time after injections of the antibody to LPS-treated Balb/C mice as illustrated in the Examples section.

As mentioned above, the tip region of TNF-α may be implicated in the toxic side effects of the cytokine on cells, thereby limiting the wider therapeutic use of TNF-α on normal cells (reviewed by Taniguchi and Sohmura, 1991). Therefore, antibodies recognizing the tip region of TNF-α can be of particular interest to discriminate between the tumoricidal effect of TNF-α on the one hand, and the trypanolytic and toxic effect of TNF-α on the other. Antibodies recognizing the above-mentioned TNF-α tip region polypeptides of the invention, will be further referred to as anti-tip antibodies.

The present invention relates also to the use of an antisense peptide of a peptide comprising at least part of the region extending from amino acids 101 to 116 of TNF-α, preferably comprising at least part of the region extending from amino acids 105 to 110 characterized in that it:

either modulates the lectin-like activities of TNF-α, and/or inhibits the toxic activity of TNF-α, and/or modulates the inflammatory cytokines inducing capacities of TNF-α, and/or modulates the adhesion molecules inducing capacities of TNF-α, and/or inhibits the metastasis promoting activity of TNF-α, for the preparation of a medicament for treating either the TNF-induced septic shock effect of TNF-α, or for treating pathological conditions associated with the in vivo lectin-like effect of TNF-α, such as for treating sepsis, septic shock, Gram negative sepsis, endotoxic shock, toxic shock syndrome, cachexia, microbial infections, rheumatoid arthritis, inflammatory conditions, respiratory distress syndrome, pulmonary fibrosis, infections, graft-versus-host-disease, reperfusion damage such as myocardial ischaemia, AIDS, cancer, immunosuppression, cerebral malaria, etc.

It is to be understood that the antisense peptides according to the present invention are characterized in that they have at least one of the following effects:

they modulate (ie inhibit or stimulate), preferably inhibit, the lectin-like effect of TNF-α preferentially from 5 to 100%, preferably at least 25%, more preferably at least with 50%, most preferably with at least 75%; or, they inhibit the toxic effect of TNF-α with from 5 to 50%, preferably at least 10%, more preferably with at least 25%, most preferably with at least 35%; or, they modulate (i.e. inhibit or stimulate), preferably inhibit the inflammatory cytokines inducing capacities of TNF-α from 5 to 100%, preferably with at least 25%, more preferably with at least 50%, most preferably with at least 75%; or, they modulate (i.e. inhibit or stimulate), preferably inhibit the adhesion molecules inducing capacities of TNF-α from 5 to 100%, preferably with at least 25%, more preferably with at least 50%, most preferably with at least 75%; or, they inhibit the metastasis promoting activity of TNF-α from 5 to 100%, preferably with at least 25%, more preferably with at least 50%, most preferably with at least 75% All these effects may be measured as mentioned for the antibodies.

More particularly, the term "antisense peptide" is reviewed by Blalock (1990) and by Roubos (1990). In this respect, the molecular recognition theory (Blalock, 1990) states that not only the complementary nucleic acid sequences interact but that, in addition, interacting sites in proteins are composed of complementary amino acid sequences (sense ligand with receptor or sense ligand with antisense peptides).

Thus, two peptides derived from complementary nucleic acid sequences in the same reading frame will show a total interchange of their hydrophobic and hydrophilic amino acids when the amino terminus of one is aligned with the carboxy terminus of the other. This inverted hydropathic pattern might allow two such peptides to assume complementary conformations responsible for specific interaction.

The antisense peptides can be prepared as described in Ghiso et al. (1990). By means of this technology it is possible to logically construct a peptide having a physiologically relevant interaction with a known peptide by simple nucleotide sequence analysis for complementarity, and synthesis of the peptide complementary to the binding site. The antisense peptides according of this preferred embodiment of the invention can be prepared by classical chemical synthesis.

The synthesis can be carried out in homogeneous solution or in solid phase.

For instance, the synthesis technique in homogeneous solution which can be used is the one described by Houben-weyl in the book entitled "Methode der organischen chemie" (Method of organic chemistry) edited by E. Wunsh, vol. 15-I et II. THIEME, Stuttgart, 1974.

The antisense peptides of the invention can also be prepared in solid phase according to the methods described by Atherton and Shepard in their book entitled "Solid phase peptide synthesis" (IRL Press, Oxford, 1989).

In order to assume the inhibition of at least one, or preferably a combination of at least two of the afore mentioned effects in vivo, the antisense peptide should form a complex with the subregion of the TNF-α tip region responsible for either of these effects of TNF-α.

The present invention relates also to the use of a complex consisting of an antisense peptide as defined above, and TNF-α, for the preparation of a medicament.

According to this embodiment of the invention, a pharmaceutical composition, containing, as active substance, a complex comprising an antisense peptide as defined above, and complete TNF-α, in association with a pharmaceutical acceptable vehicle, is provided.

Instead of, or in addition to TNF-α, the above mentioned compositions could also contain IL-1α, IL-1β, IL-6, IFN-gamma, IFN α/β, IL-8, or any other immunoreactive agent.

The above-mentioned composition can be used for treating illnesses wherein a treatment with TNF-α is beneficial such as tumors.

According to a preferred embodiment, the present invention relates to the use of an antibody or an antisense peptide as defined above, characterized in that it modulates the lectin-like activities of TNF-α.

According to an even more preferred embodiment, the present invention relates to the use of an antibody or an antisense peptide as defined above, characterized in that it inhibits the lectin-like activities of TNF-α. Illustrations of said embodiment containing an antibody are given in the examples section of the invention.

According to a possible embodiment, the present invention relates to the use of an antibody or an antisense peptide as defined above, characterized in that it stimulates the lectin-like activities of TNF-α.

According to yet another preferred embodiment, the present invention relates to the use of an antibody or an antisense peptide as defined above, characterized in that it inhibits the toxic activity of TNF-α.

According to yet another embodiment, the present invention relates to the use of an antibody or an antisense peptide as defined above, characterized in that it modulates the inflammatory cytokines inducing capacities of TNf-α.

According to yet another preferred embodiment, the present invention relates to the use of an antibody or an antisense peptide as defined above, characterized in that it inhibits the inflammatory cytokines inducing capacities of TNf-α.

According to yet another embodiment, the present invention relates to the use of an antibody or an antisense peptide as defined above, characterized in that it modulates the adhesion molecules inducing capacities of TNF-α.

According to yet another preferred embodiment, the present invention relates to the use of an antibody or an antisense peptide as defined above, characterized in that it inhibits the adhesion molecules inducing capacities of TNF-α.

According to yet another possible embodiment, the present invention relates to the use of an antibody or an antisense peptide as defined above, characterized in that it stimulates the adhesion molecules inducing capacities of TNF-α.

According to yet another preferred embodiment, the present invention relate to the use of an antibody or an antisense peptide as defined above, characterized in that it inhibits the metastasis promoting activity of TNF-α, According to yet another preferred embodiment, the present invention relates to the use of any of the above-defined antibodies or antisense peptides, characterized in that they increase the half life time of TNF-α. Antibodies or antisense peptides according to this latter embodiment are preferably used in combination with TNF-α.

It is to be understood that the TNF muteins according to the present invention can be administered either directly in the form of mutein protein in a pharmaceutical composition as described above, or in the form of cells transfected with the nucleic acid coding for such muteins, said nucleic acid being inserted into any suitable vector, as known to those skilled in the art.

Thus, the present invention relates also to a method for treating patients suffering from any of the above mentioned illnesses consisting of administering cells transfected with the cDNA coding for the TNF muteins as defined above, said nucleic acid being inserted into any suitable vector, as known to those skilled in the art.

The cells transfected by such a vector-nucleic acid combination are preferably autologous cells derived from the patient (e.g. a cancer patient) to be treated with such compositions. Said vector-nucleic acid combination has to be constructed in such a way as to allow continuous expression of the mutein protein at either a constant level or at a level which can be modified, depending on the exact nature of the vector used to make the vector-nucleic acid combination. In this format, the present invention may be used to treat cancer patients.

ABBREVIATIONS

TNF-α: tumor necrosis factor-alpha
mTNF-α: mouse tumor necrosis factor-alpha
hTNF-α: human tumor necrosis factor-alpha
Bio: Biotin group
r: recombinant
wt: wild-type

BRIEF DESCRIPTION OF THE FIGURES

FIG. 2: pIG2 nucleic acid sequence. (SEQ ID NO 2). The origin of nucleotide stretches used to construct plasmid pIG2 is specified hereafter.

Position

3300–206: lambda PL containing EcoRI-MboII blunt fragment of pBL(λ) (Pharmacia)

207–266: synthethic sequence containing multiple cloning sites and the ribosome binding site of which the ATG initiation codon is located at position 232–234

267–772: rrnBT$_1$T$_2$ containing HindIII-SspI fragment from pKK223 (Pharmacia)

773–3300: tetracycline resistance gene and origin of replication containing the EcoRI-DraI fragment of pAT 153 (Bioexcellence)

Figures 3A, 3B:
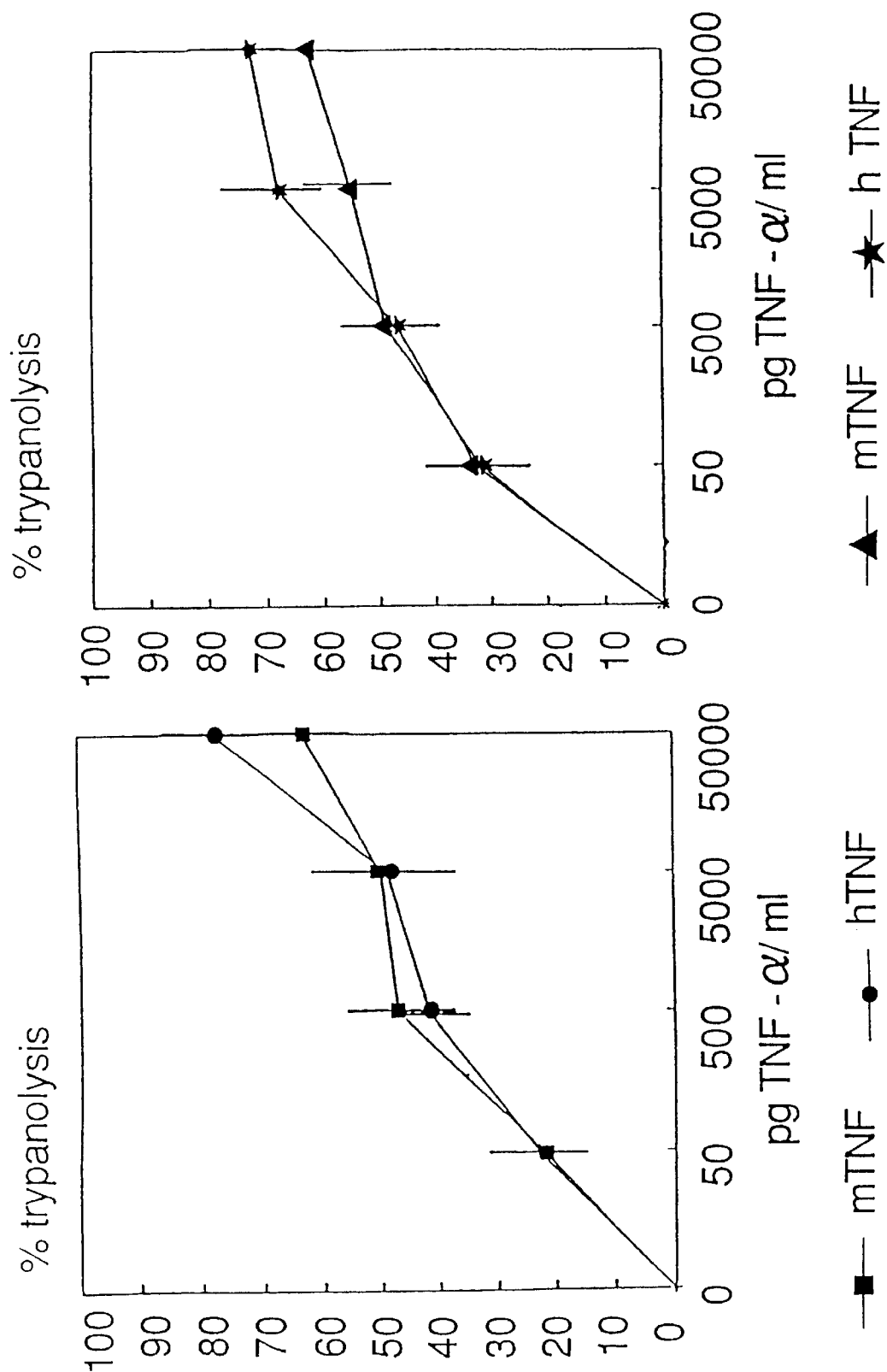

FIGS. 3A and 3B: In vitro trypanocidal activity of recombinant mouse (m) or human (h) TNF-α on $T.$ $brucei$ $brucei$ (A) and $T.$ $rhodesiense$ (B). Thereto, $2\times10^6$/ml purified bloodstream trypanosomes, isolated 1 day before the first in vivo maximum peak, are incubated for 5 hours in PBS, 1% glucose, 1% normal mouse serum at 37° C. with various concentrations of recombinant TNF-α. After 5 hours, the number of living parasites is assessed and is compared with the control wells in which only incubation medium was added. The spontaneous mortality in the control wells was always lower than 10%. The values represent the means of quadruplicates and the standard deviation.

Figure 4:
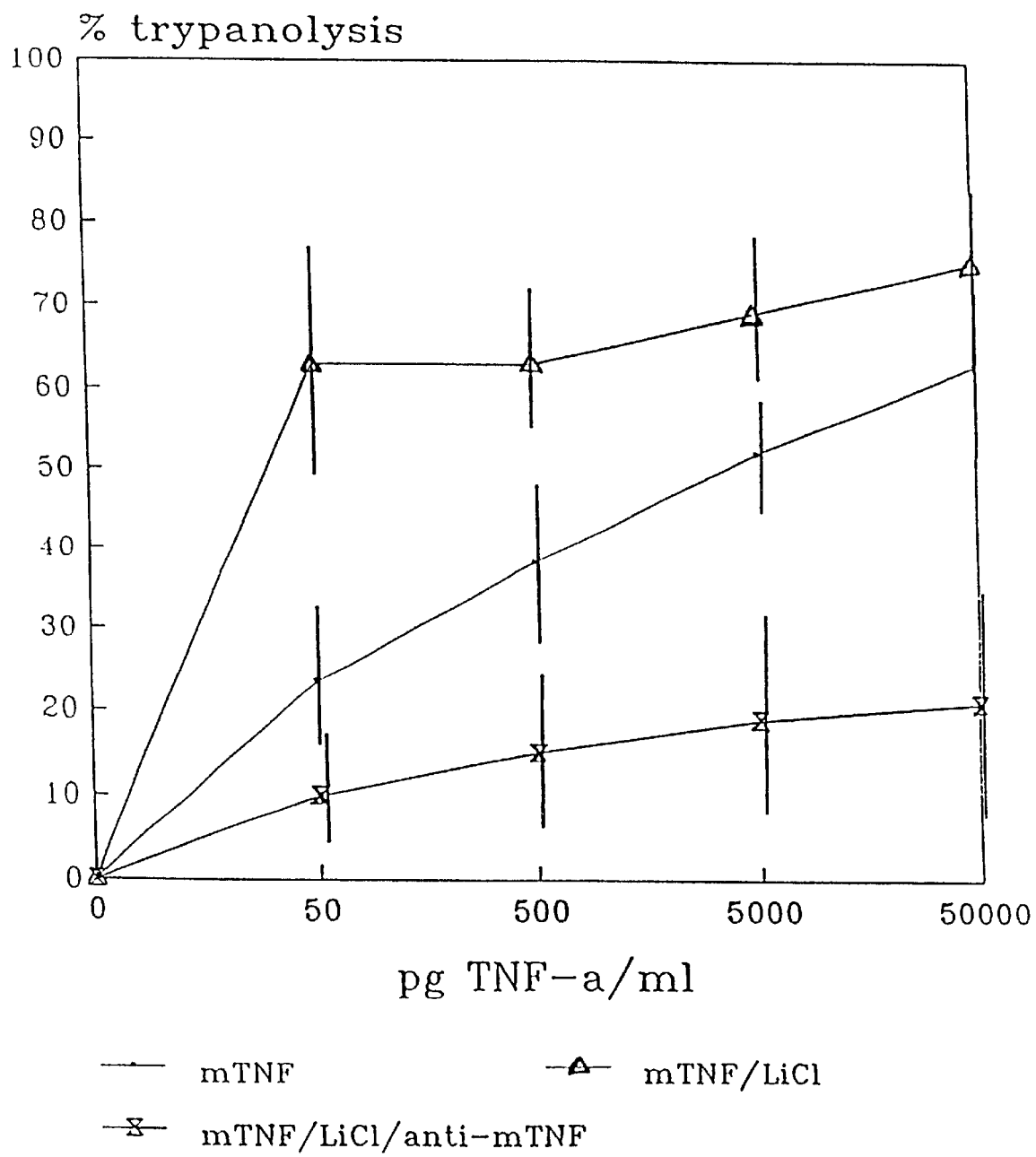

FIG. 4: LiCl potentiates the mouse TNF-α mediated trypanolysis in vitro. Trypanosomes were incubated for 5 hours with serial dilution of mTNF-α alone or enriched with 1 μg/ml of LiCl either in the presence or absence of anti-mTNF-α 1F3F3D4 monoclonal antibodies, which are capable of neutralizing the cytotoxic effect of TNF-α. The values represent the means of quadruplicates and the standard deviatation. Especially at low TNF-α concentrations (50 and 500 pg/ml), the values in the LiCl group differed significantly (<0.0008 and 0.009) from the control group indicating that LiCl synergistically potentiates the trypanocidal effect of mTNF-α. LiCl by itself had no effect on the survival of the trypanosomes as no difference with control values were seen (data not shown).

Figures 5A, 5B:
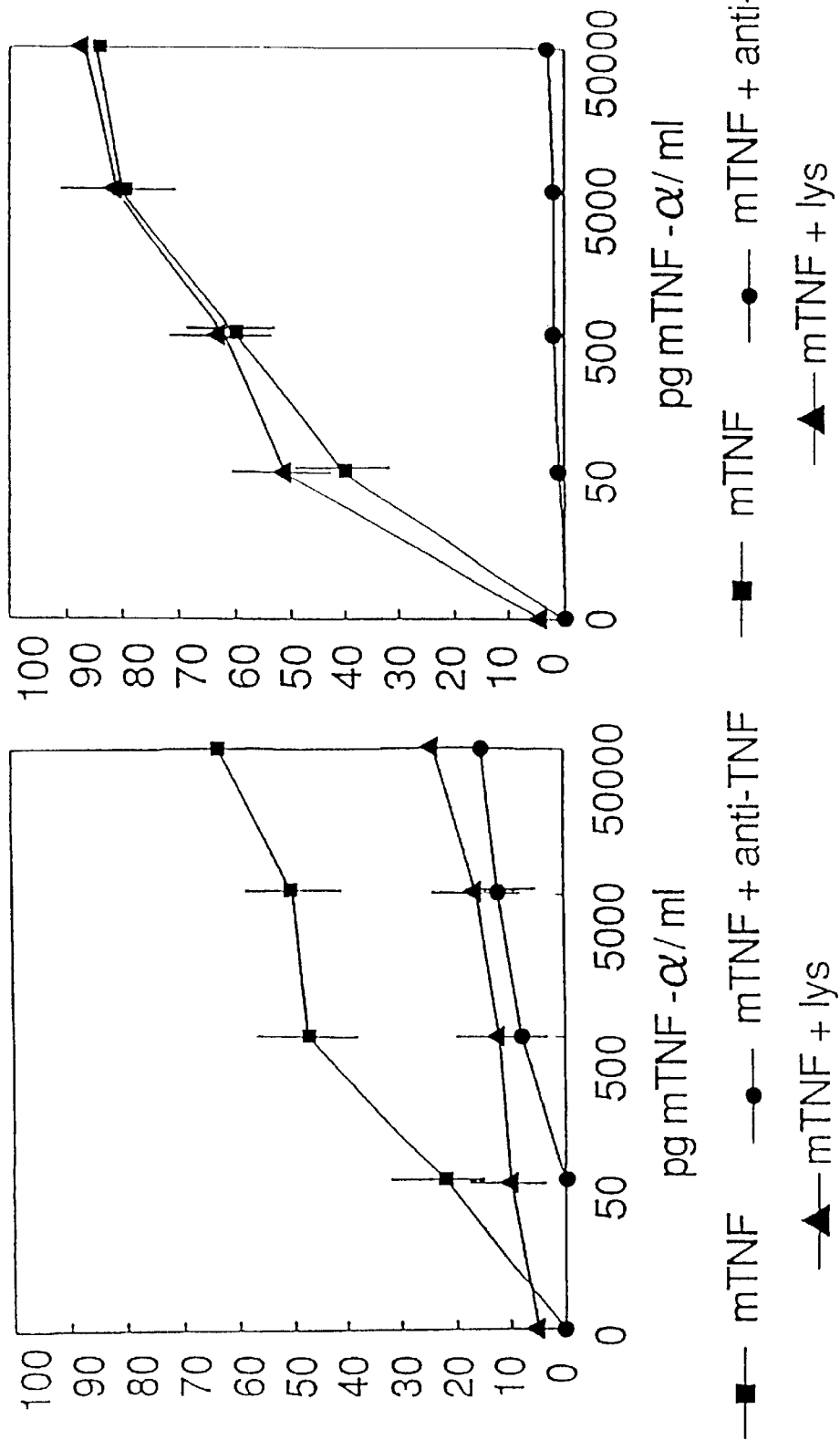

FIGS. 5A and 5B: $T.$ $brucei$ $brucei$ lysate inhibits the in vitro trypanocidal but not the cytolytic (cytotoxic) capacity of mTNF-α. Preincubation of mTNF-α for 1 h with 10 μg/ml of trypanosome lysate results in a potent inhibition of the TNF-α-specific trypanocidal effect (A), whereas it has no effect on the cytolytic or tumoricidal capacity of TNF-α (B). The neutralizing anti-mTNF-α 1F3F3D4 monoclonal antibody (anti-mTNF; Lucas et al., 1990) was used to demonstrate that cytolysis was specifically indicated by TNF-α. The values represent the means of quadruplicates and the standard deviation.

Figures 6A, 6B:
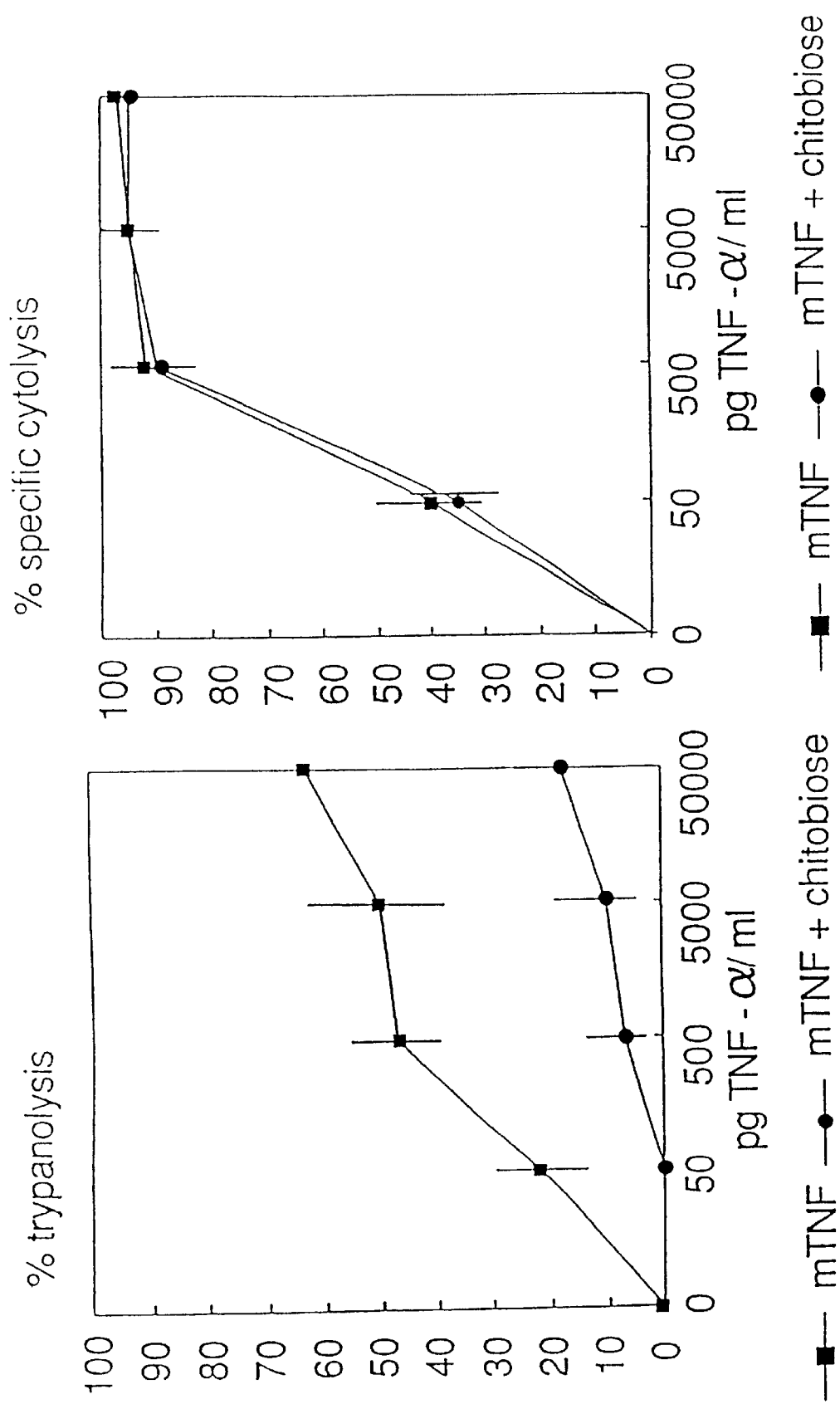

FIGS. 6A and 6B: Preincubation of mTNF-α with N,N'-diacetylchitobiose (indicated as chitobiose) potently inhibits the trypanocidal activity (A), but not the cytolytic activity (B) of mouse TNF-α. mTNF-α was preincubated for 2 h with 1 μg/ml of N,N'-diacetylchitobiose before adding it in a serial dilution to bloodsteam forms of $T.$ $brucei$ $brucei$ (A) or to L929 cells (B) to be tested on its trypanocidal or cytolytic activity (as described in the examples), respectively.

Figure 7:
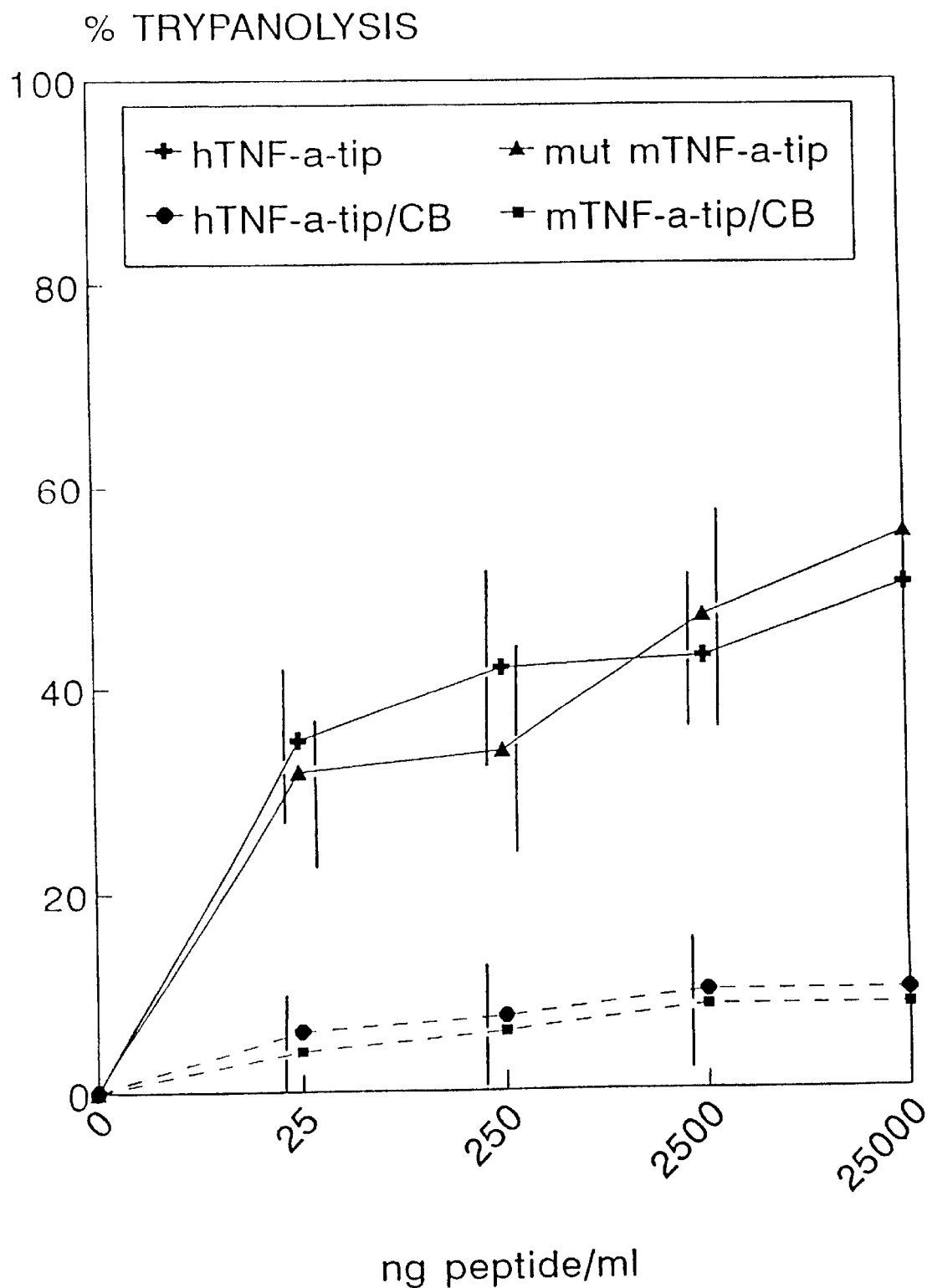

FIG. 7: Trypanocidal activity of the circularized, biotinylated mouse TNF-α tip peptide (Bio-GG-CGPKDTPEGAELKPWYC) (mtip) and the biotinylated human TNF-α tip peptide (Bio-GG-CGQRETPEGAEAKPWYC) (htip), and the biotinylated linear subpep1 (Bio-GG-CTPGAEC) (subtip) on the bloodstream forms of $T.$ $brucei$ $brucei$ and inhibition of the trypanocidal activity by pre-incubation with N,N'-diacetylchitobiose (Chitobiose). Serial dilutions of these circularized mouse or human TNF-α tip peptides were added either directly to $2\times10^6$/ml purified bloodstream trypanosomes or after pre-incubation for 2 h with 1 μg/ml of N,N'-diacetylchitobiose. After 5 hours, the number of living parasites is assessed and is compared with the control wells in which only incubation medium was added.

FIG. 8: Trypanocidal activity of different synthetic tip peptides. Serial dilutions of mTNF-α tip (Bio-GG-CGPKDTPEGAELKPWYC), hTNF-α tip (Bio-GG-CGQRETPEGAEAKPWYC), subpep 2 (Bio-GG-EGAELKPWY), subpep 1 (Bio-GG-C-TPEGAE-C) and the D-amino acid analogue of subpep 1 (=subpep 4) were added to $2\times10^6$/ml purified bloodstream forms of $T.$ $brucei$ $brucei$.

FIG. 9: Trypanocidal activity of subpeptide 1 and muteins thereof. Serial dilutions of subpep 1 (Bio-GG-C-TPEGAE-C), subpep 3 (Bio-GG-TPE), mutpep 1 (Bio-GG-C-α PEGAE-C), mutpep 2 (Bio-GG-C-TAEGAE-C), mutpep 3 (Bio-GG-C-TPAGAE-C), mutpep 4 (Bio-GG-C-TPEAAE-C) and mutpep 5 (Bio-GG-C-TPEGAA-C) made in 100 μl were added to $2\times10^5$/ml purified bloodstream forms of $T.$ $brucei$ $brucei$ (final concentration $10^6$ parasites/ml). As in FIG. 8, after 5 hours, the number of live parasites is assessed and compared with the control wells in which only incubation medium is added.

Figure 10:
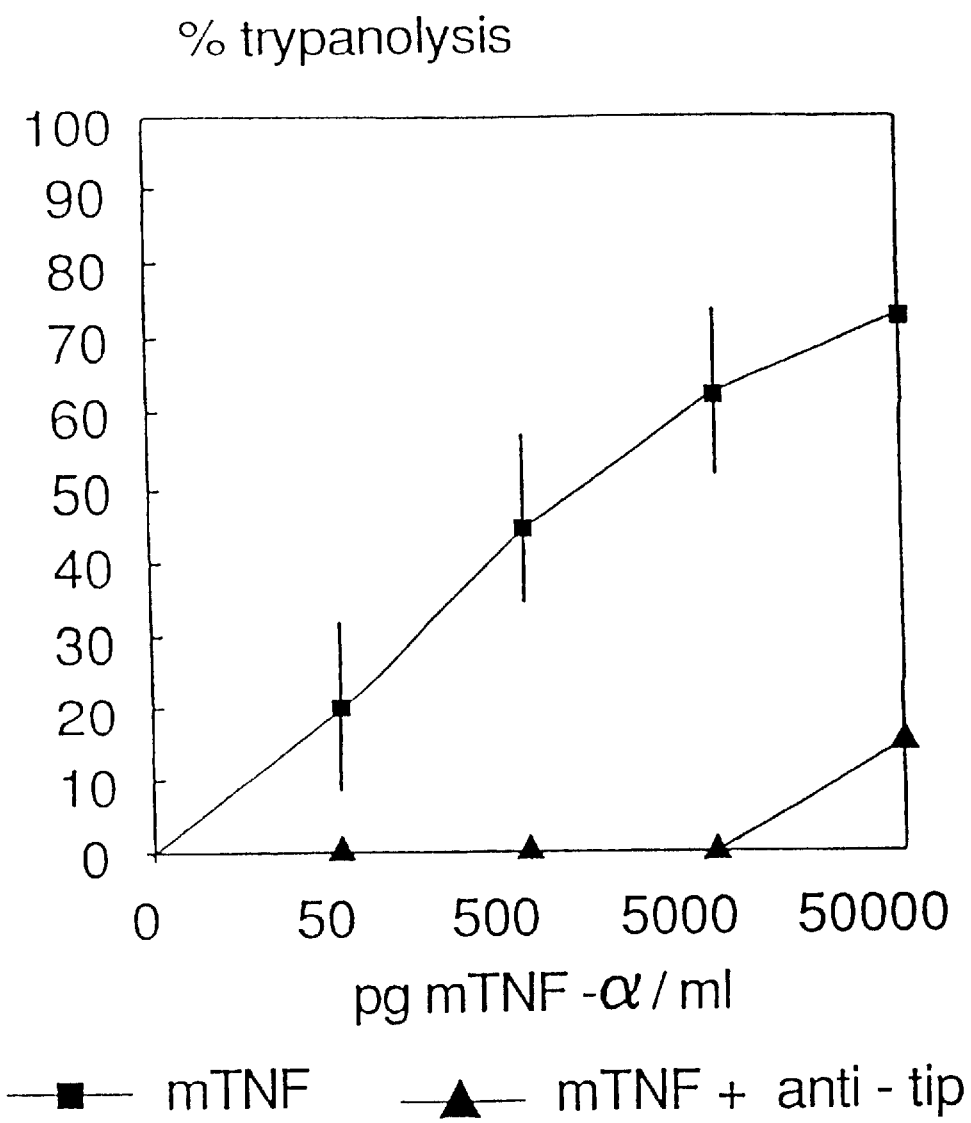

FIG. 10: The anti-mTNF-α tip polyclonal antibody (anti-tip) potently inhibits the trypanocidal effect of mTNF-α, but it only weakly inhibits the cytolytical activity against L929 cells. mTNF-α was preincubated for 1 h with 10 μg/ml of protein G purified anti-tip polyclonal IgG before adding it to $2 \times 10^6$ bloodstream purified *T. brucei brucei*/ml. After 5 hours the trypanocidal activity of mTNF-α alone or pretreated with anti-tip polyclonal IgG was evaluated by counting the number of live parasites. The cytolytical activity of TNF-α alone or pretreated with anti-tip polyclonal IgG was evaluated on cell survival of L929 cells after 48 hours incubation in the absence of actinomycin D.

Figure 11:
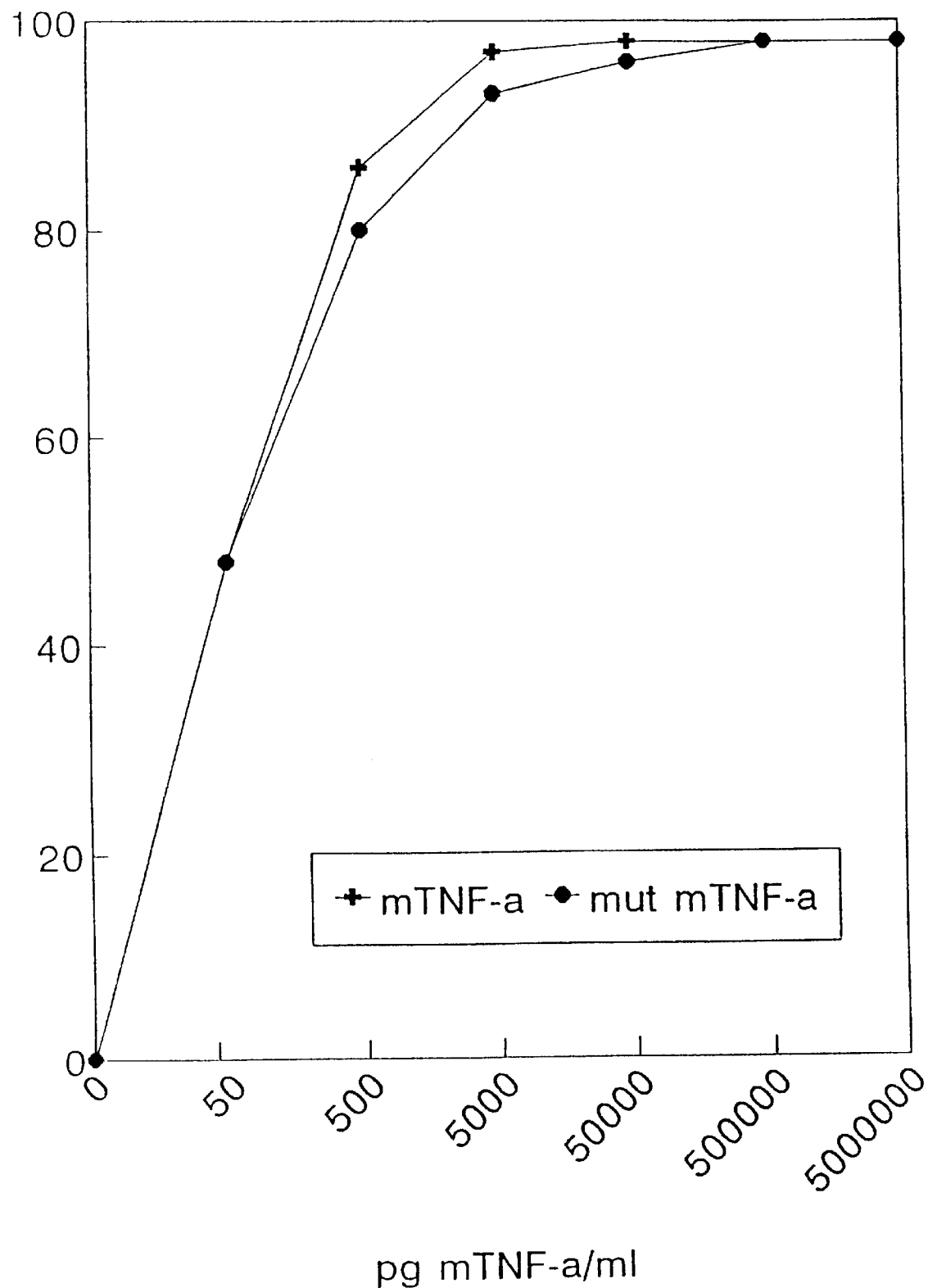

FIG. 11: In vitro cytolytic (cytotoxic) activity of wild type mTNF-α and mTNFT105A on L929 cells as tested in the 48 hours assay in the absence of Actinomycin D. The assay was performed as explained in the Materials and Methods section of the Examples.

FIG. 12: In vitro *T. brucei brucei* trypanocidal of wild type mTNF-α and T105A mTNF-α. The trypanocidal activity of wild type and T105A mutated mTNF-α was tested as explained in the legend of FIG. 3.

FIG. 13: Effect of the intravenous (i.v.) injection of different concentrations of wild type and T105A mutated mTNF-α on the survival time of C57BL/6 mice. Per group of 6 mice, 10 μg top left), 5 μg (top right), 2.5 μg (bottom left) or 1 μg (bottom right) per 200 μl of PBS of either wild type mTNF-α or T105A tip mutated mTNF-α was i.v. injected and the survival time was assessed until 72 hours after injection.

EXAMPLES

Materials and Methods

1. Animals

Female 10-week old Balb/C mice (SCK, Mol, Belgium) were used in all in vivo LPS-induced septic shock experiments.

Female 10-weeks old C57BL/6 mice (Iffa Credo, France) were used in all in vivo TNF-induced lethal shock experiments.

2. Cell Lines

L929 fibrosarcoma cells were obtained from the Rega Institute, Leuven, Belgium.

3. Trypanosomes

The *Trypanosoma brucei brucei* AnTat 1.1 (EATRO 1125) pleomorphic bloodstream form was kindly provided to us by Dr. N. Van Meirvenne of the Institute for Tropical Medecine, Antwerp, Belgium, and the *Trypanosoma brucei rhodesiense* Trp 11 pleomorphic bloodstream form was kindly provided to us by Dr. E. Bajyana Songa (Dept. Molecular Biology, Free University of Brussels, Belgium)

A *T. brucei* lysate was prepared by a triple freeze-thaw cycle of purified trypanosomes.

4. Cytokines, Antibodies and Biochemicals

Purified recombinant mTNF-α and recombinant hTNF-α, produced in *E. coli*, with a specific activity of $10^8$ units/mg and $2 \times 10^7$ units/mg respectively, were produced by Innogenetics, Gent, Belgium. Human recombinant TNF-β (lymphotoxin) is commercially available from the Genzyme Corporation (Cambridge, Mass., USA).

The rat-anti-recombinant mTNF-α 1F3F3D4 (Lucas et al., 1990) and the mouse-anti-recombinant hTNF-α monoclonal antibodies are both commercially available from Innogenetics (Ghent, Belgium).

The soluble p55 hTNF-α receptor protein was obtained from Dr. D. Wallach (Dept. of Membrane Research & Biophysics, Weizmann Institute, Rehevot, Israel).

Lipopolysaccharide W *E. coli* 055:B5 (LPS) was purchased from Difco Laboratories, Detroit, Mich., USA.

5. Oligosaccharides/lectins

N,N'-diacetylchitobiose was purchased from Sigma (St. Louis, Mo., USA). In the in vitro TNF-α-trypanocidal assay, the TNF-α-derived tip peptides are preincubated for 1 h with 1 μg/ml oligosaccharide.

The lectins *Griffonia (Bandeiraea) simplicifolia* A4 (GSI-A4) and *Triticum vulgaris* agglutinin (WGA) were purchased from Sigma (St. Louis, Mo., USA).

*Galanthus nivalis* agglutinin (GNA) and *Urtica dioica* agglutinin (UDA) were purified and kindly provided by Dr. L. Wijns (Laboratory of Crystallography, Free University of Brussels, Belgium).

6. In vitro biological assay to measure the cytotoxic and trypanocidal activity of recombinant hTNF-α or mTNF-α

6.1. L929 cell killing assay

TNF-sensitive mouse fibrocarcinoma L929 cells in complete RPMI 1640 medium (Gibco BRL, Paisley, Scotland) were treated with actinomycin D (1 μg/ml) at a cell concentration of $3 \times 10^5$ cells/ml. Thus, 100 μl of the suspension in 96-well flat bottomed culture plates was mixed with 100 μl, containing either medium (negative control), 100 μl h/mTNF-α (serially diluted in medium; positive control), or 100 μl h/mTNF-α+1 μg/ml of oligosaccharide, or 100 μl of the TNF-α derived tip peptides (serially diluted in medium). After 18 h of culture at 37° C., viability of the cell cultures was assessed by dye uptake analysis. The latter was accomplished by decanting the medium from the plates and staining the cells for 10 min with Crystal Violet (0.5% Crystal Violet, 8% (v/v) formaldehyde (40%), 0.17% NaCl, 22.3% (v/v) ethanol). After staining, the cells were extensively washed with tap water and the dye was dissolved in 100 μl/well of 33% acetic acid. The plates were read spectrophotometrically at 577 nm with a Titertek multiscan MCC340 ELISA Reader (Flow Laboratories, McLean, Va.). Sometimes, the cytotoxic assay was performed in the absence of actinomycin D using an identical experimental set-up but a longer incubation period (48 instead of 18 hours). The latter assay is less sensitive but measures the intrinsic cytotoxic activity of the TNF-α protein.

6.2. In vitro trypanocidal assay

Two times $10^6$/ml purified bloodstream forms of *Trypanosoma brucei brucei* or *T. brucei rhodesiense* isolated 1 day before the first in vivo maximum peak is reached, were incubated for 5 h in phosphate buffered saline (PBS), 1% glucose, 1% normal mouse serum (incubation medium) at 37° C. with various concentrations of recombinant mTNF-α, recombinant hTNF-α or the TNF-α-derived tip peptides, all in the absence or the presence of anti-tip peptide polyclonal or monoclonal antibodies. After 5 h of incubation, the number of live (=moving) parasites was assessed (counting chamber) and compared the control wells in which only incubation medium was added to the trypanosomes. The spontaneous mortality in the control wells after 5 h was always lower than 10%. All treatments were done in quadruplicate and all reported in vitro trypanolysis experiments were repeated at least 3 times.

7. In vivo assay to evaluate the tumoricidal effect of human and mouse TNF-α

7.1. Anti-tumor effect of hTNF-α on subcutaneous HT-29 tumors in nude mice.

To test the anti-tumor effect of wild type and tip-mutated or -deleted hTNF-α, $5 \times 10^6$ HT-29 human adenocarcinoma (ATCC HTB38) were subcutaneously (s.c.) injected in nude mice (Iffa Credo, France). The treatement comprises daily perilesional injections for 6 days per week, followed by 1 day without a treatment this for a period of 1 month. Perilesional is a subcutaneous injection near the site of the tumor but outside the tumor nodule. Per mouse, 5 μg of human recombinant TNF-α was injected. Tumor volume was estimated every 3 or 4 days by measuring the larger (a)

and the smaller (b) diameter and calculating the a×b²×0.4 as known in the art.

7.2. The B16B16 melanoma model to test the anti-tumor activity of wild type and tip-mutated or tip-deleted mTNF-α.

5.10⁶ B16B16 melanoma cells (Hart and Fidler, 1980) are injected subcutaneously (s.c.) in the back of C57/black mouse (Iffa Credo, France). Between days 8 and 10, a subcutanous tumor nodule appears at the inoculum site in all animals. Treatment started at day 10 for 10 days and consisted of a daily perilesional injection of 5 μg mTNF-α/mouse. The tumor volume was estimated as mentioned above.

8. In vivo assays to evaluate the toxic effect or septic shock effect of recombinant hTNF-α or mTNF-α

8.1. Induction of the LPS-induced septic shock syndrome in mice

Intraperitoneal (i.p.) injection of 500 μg of LPS/mouse causes death within 48 hours. Protection against septic shock syndrome was assayed by injecting 10-weeks old Balb/C mice (10 mice/group) with 100 μg of the protein G-purified rabbit-anti-mTNF-α-tip peptide polyclonal antibodies in 200 μl PBS, or with an equal amount of control rabbit polyclonal antibodies or with 200 μl PBS, 2 h before injection of 500 μg of LPS/mouse. The number of days of postinjection survival was then assessed.

8.2. Induction of the TNF-α-induced lethal shock

Intravenous (i.v.) injection of 10-week-old C57BL/6 mice with 10 μg/mouse of mTNF-α causes death within 48 hours.

Ten weeks old C57BL/6 mice (5 to 6/group) were injected with different doses of wild type or mutant mouse TNF-α and the postinjection survival time was then assessed.

9. Statistics

All data were analyzed using the Mann-Whitney U test.

10. Biotinylated peptide synthesis

All amino acid sequences are given in the conventional and universally accepted three-letter or one-letter code.

The peptide sequences are given left to right which, by convention, is the direction from the amino terminus to the carboxyterminus.

A number of unconventional codes are also used to represent chemical groups or modifications and are defined as follows:

Ac=acetyl group
Bio=D-biotinyl group
Fmoc=9-fluorenylmethoxycarbonyl group
tBoc=tertiary butyloxycarbonyl group All of the peptides described were synthesized on Tenta-Gel S-RAM (Rapp Polymere, Tübingen, Germany), a polystyrene -polyoxyethylene graft copolymer functionalized with the acid-labile linker 4-(α-Fmoc-amino-2',4'-dimethoxybenzyl) phenoxyacetic acid (Rink et al., 1987) in order to generate peptide carboxy-terminal amides upon cleavage. t-Butyl-based side chain protection and Fmoc-α-amino-protection was used. The sulfhydryl group of cysteine was protected with a trityl group. Couplings were carried out using preformed O-pentafluorophenyl esters. Biotin was coupled using TBTU as the activating agent in the presence of two equivalents of the base N-methylmorpholine. All syntheses were carried out on a Milligen 9050 PepSynthesizer (Novato, Calif.) using continuous flow procedures. Following cleavage with trifluoroacetic acid in the presence of scavengers and extraction with diethylether, all peptides were analyzed by C18-reverse phase chromatography.

11. ELISA assay to quantify wild type and tip-mutated or tip-deleted mouse TNF-α protein An ELISA assay to measure the protein concentration of the wild type and tip-deleted or tip-mutated mouse TNF-α protein was developed. Thereto, the microtiter plates were coated overnight at room temperature with 100 μl per well of 2.5 μg/ml of rabbit anti-mouse TNF-α (Innogenetics, Belgium) in 10 mM Tris, 10 mM NaCl, 10 mM NaN3. Subsequently, the plates were washed once with washing buffer (PBS, 0.05% Tween-20) and the remaining binding sites were blocked for at least one hour at 37° C. with 300 μl per well of PBS buffer supplemented with 1% BSA and 0.1% NaN3. Dilutions of sample or standard mTNF-α (0.01 to 10 ng/ml mTNF-α), made in 100 μl of PBS supplemented with 1% BSA, 1% rabbit serum, and 0.1% mertiolate are then added to each well and incubated for 2 hours at 37° C. Thereafter, the plates are washed 4 times with washing buffer and 100 μl/well of biotinylated rabbit anti-mouse TNF-α which has been diluted with sample diluent to a concentration of 0.125 μg/ml is added for another 2 hours at 37° C. Subsequently, the plates are washed four times with washing buffer wherafter 100 μl of straptavidin-horseradish peroxidase (Jackson Immunoresearch Labs), which has been diluted in sample diluent to a concentration of 100 ng/ml is added and incubated for 30 minutes at 37° C. To each well, 100 μl of TMB solution (8.7 g/l tetramethyl benzidine in DMSO) which has been diluted 100 times in substrate buffer (solution A: 0.1M Na2HP4.2H2O; solution B: 0.1M citric acid; solution C: 3% H2O2. Mix 149 parts of solution A with 100 parts of solution B, and add 2 ml of solution C per 1 liter mix) is added and incubated for 30 minutes at room temperature. The reaction is stopped by adding 100 μl per well of 2N H2SO4 wherafter the optical density is read at dual wavelength (450/595 nm).

EXAMPLE 1

Generation of Recombinant Wild-type and Tip-mutated or -Deleted mTNF-α Protein in *E. coli*

A schematic overview of the amino acid sequence spanning the region of amino acids 105 to 110 of mTNF-α and all constructed mTNF-α muteins is given in Table II.

TABLE II

| Positions | 105 | 106 | 107 | 108 | 109 | 110 |
|---|---|---|---|---|---|---|
| mTNF-α | Thr | Pro | Glu | Gly | Ala | Glu |
| T105A mTNF | Ala | Pro | Glu | Gly | Ala | Glu |
| P106A mTNF | Thr | Ala | Glu | Gly | Ala | Glu |
| E107A mTNF | Thr | Pro | Ala | Gly | Ala | Glu |
| E110A mTNF | Thr | Pro | Glu | Gly | Ala | Ala |
| E107A/E110A mTNF | Thr | Pro | Ala | Gly | Ala | Ala |
| T105A/E110A mTNF | Ala | Pro | Glu | Gly | Ala | Ala |
| T105A/E107A mTNF | Ala | Pro | Ala | Gly | Ala | Glu |
| T105A/E167A/E110A mTNF | Ala | Pro | Ala | Gly | Ala | Ala |
| del TPEGAE mTNF | — | — | — | — | — | — |

1. Construction of pIG2mTNF

A 701 bp TaqI/XbaI fragment, containing the mTNF-α coding sequence except the signal sequence and the first 21 bp of the mature sequence, was isolated from pBSK(+) mTNF. This pBSK(+)mTNF vector contains the full-size mTNF-α cDNA as been published by Fransen et al, (1985).

This fragment was subsequently ligated to the following synthetic DNA sequence:

5'-CATGCTCAGATCAAGTAGTCAAAATT-3' (SEQ ID NO 3)

3'-GTACGAGTCTAGTTCATCAGTTTTAAGC-5' (SEQ ID NO 4) startcodon mature mTNF-α

Figure 1A:
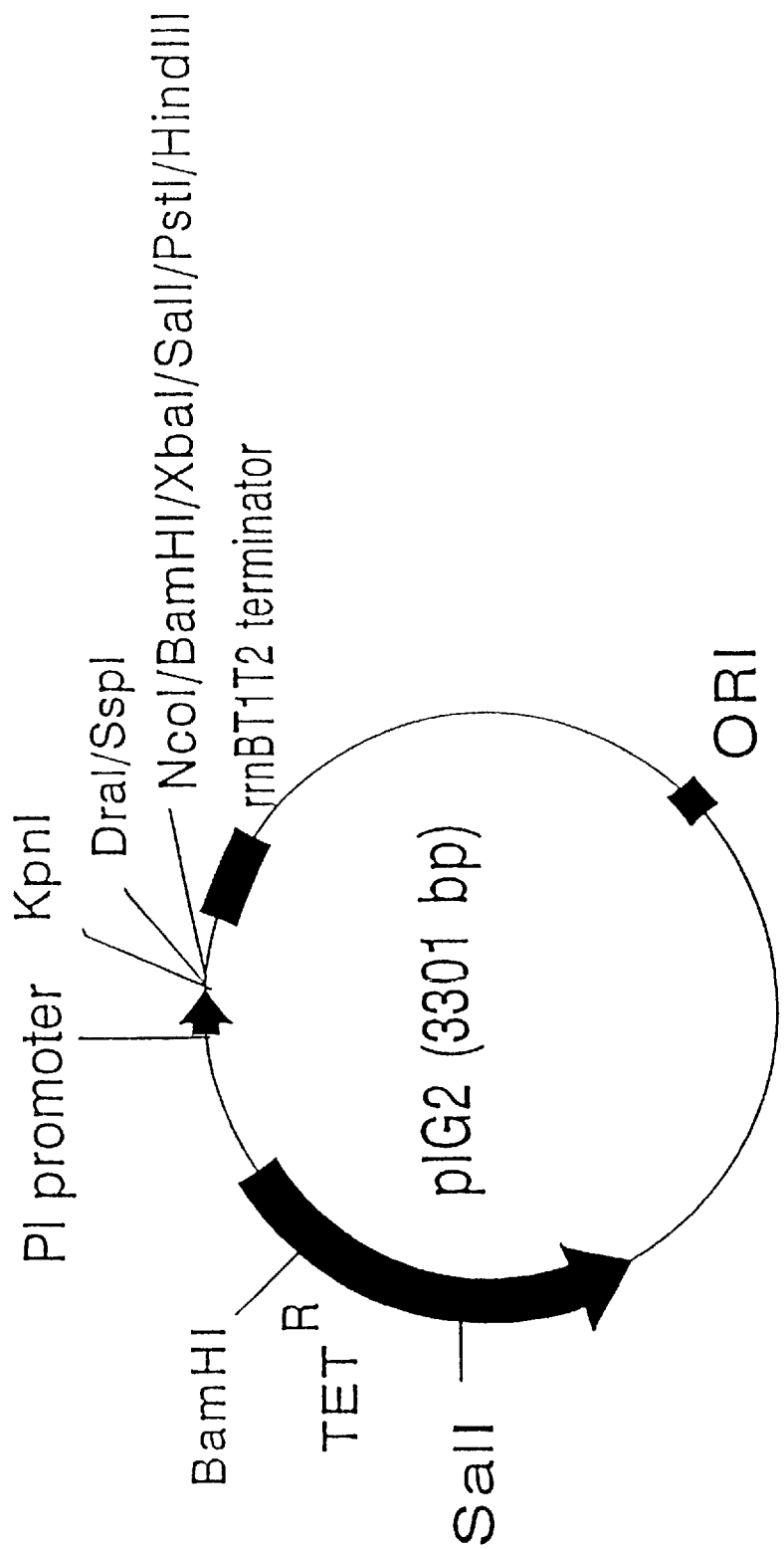
FIGS. 1A and 1B: Restriction map of the plasmid pIG2 used to express the wild type and tip-mutated or tip-deleted mTNF-α.
Figure 1B:
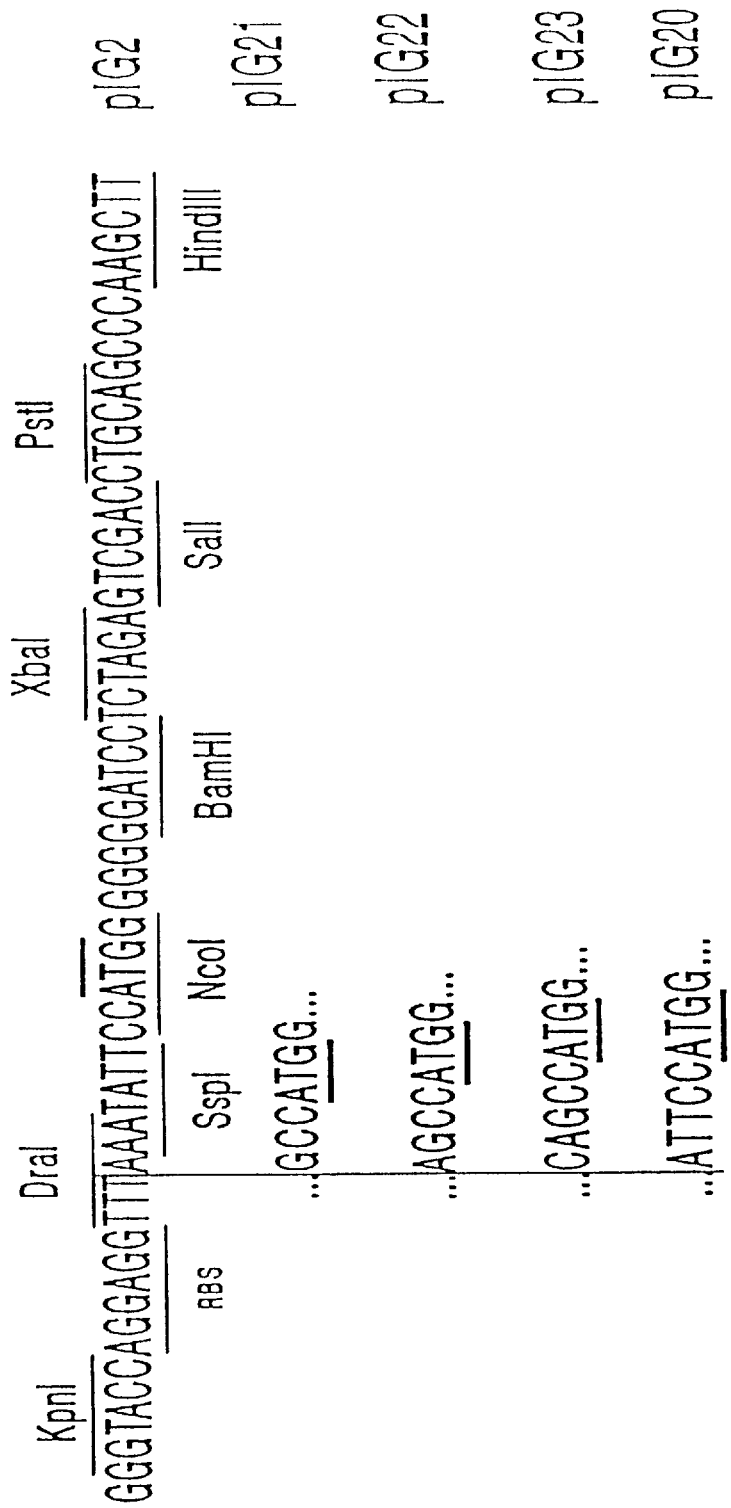

This new 727 bp sequence was then ligated into the SspI/XbaI opened vector pIG2 (SEQ ID NO 2), resulting in the vector pIG2mTNF.

pIG2 is a versatile expression vector for E. coli. It contains the temperature-inducible leftward promotor of phage lambda, a synthetic ribosome binding site, a multilinker sequence, the rrnBT1T2 transcriptional terminator and a tetracycline resistance gene (FIGS. 1 and 2)

Transformation and subsequent induction of pIG2mTNF to E. coli host MC1061(pAcI) resulted in an expression level of ±10% of total cellular protein (data not shown).

2. Construction of mTNF-α Thr105 mutant pIG2mTNFT105A

The mTNF-α Thr105 mutant, wherein the Thr105 was replaced by an Ala residue, was generated by introducing the synthetic oligonucleotide primers 5'-CAAGGACGC TCCGGAGGGGGCTGAGCT-3' and 5'-CAGCCCCC TCCGGAGCGTC-3' in the StyI-SacI digested wild type (wt) mTNF-α, thereby replacing the Thr105 by an Ala residue and creating an unique BstEI control restriction site in the mutated TNF insert, which is not present in the wt TNF-α sequence.

Thereto pIG2mTNF DNA (13 μl=±8 μg) was cut with BamHI (40 Units, 10 Units/μl, Boehringer Mannheim) in a total volume of 80 μl buffer B (Boehringer Mannheim) for 3 hours at 37° C. The digested DNA was purified via the Geneclean method (Bio101, La Jolla) and resuspended in 68 μl of sterile doubledistilled water. To this volume 8 μl of 10 times concentrated buffer H (Boehringer Mannheim) and 40 Units StyI (Boehringer Mannheim, 10 Units/μl) )were added and again incubated for 3 hours at 37° C. A 911 bp BamHI/StyI fragment was isolated from a 1.2% agarose gel via the Geneclean method and resuspended in 20 μl sterile doubledistilled water. This material is called fragment 1.

To generate the second fragment, pIG2mTNF DNA (8 μl=±5 μg) was cut with BamHI (40 U, 10 U/μl, Boehringer Mannheim) in a total volume of 80 μl buffer B (Boehringer Mannheim) for 3 hours at 37° C. The digested DNA was purified via the Geneclean method (Bio101, La Jolla) and resuspended in 68 μl of sterile doubledistilled water. To this volume 8 μl of 10 times concentrated buffer A (Boehringer Mannheim) and 40 Units SacI (Boehringer Mannheim, 10 U/μl) were added and again incubated for 3 hours at 37° C. A 3071 bp SacI/BamHII fragment was isolated from a 1.2% agarose gel via the gene clean method and resuspended in 40 μl sterile doubledistilled water. This material is called fragment 2.

To generate the mTNF-α Thr105 mutant pIG2mTNFT105A, 400 pmole (100 pmole/μl) of each of the synthetic oligos in a total volume of 10 μl were heated for 3' at 95° C., 10' at 65° C. and were subsequently allowed to reach roomtemperature. The annealed oligos were subsequently placed in ice.

buffer (Boehringer Mannheim), 1 Units of T4 ligase (Boehringer Mannheim, 1 Unit/μl) was added and the mixture was incubated for 3 hours at 15° C. The ligation mixture was transformed to DH1(lambda) competent cells, plated out on Tetracyclin containing LB plates and grown overnight at 37° C. Plasmid DNA was prepared from selected colonies and analysed via restriction digestion (BspEI, BamHI, StyI and SacI). A via restriction analysis confirmed vector pIG2mTNFT105A was transformed to MC1061 (pAcI). This vector/host combination was further used for prokaryotic expression of the mTNFT105A mutein.

3. Construction of mTNF-α Pro106 mutant pIG2mTNFP106A

In this construct the Pro106 of mTNF-α is changed to an Ala residue. In the course of the construction an extra NarI was created in the mTNF coding sequence, which is not present in the wt mTNF sequence.

Thereto pIG2mTNF DNA (13 μl=±8 μg) was cut with BamHI (40 Units, 10 Units/μl, Boehringer Mannheim) in a total volume of 80 μl buffer B (Boehringer Mannheim) for 3 hours at 37° C. The digested DNA was purified via the Geneclean method (Bio101, La Jolla) and resuspended in 68 μl of sterile doubledistilled water. To this volume 8 μl of 10 times concentrated buffer H (Boehringer Mannheim) and 40 Units StyI (Boehringer Mannheim, 10 U/μl) were added and again incubated for 3 hours at 37° C. A 911 bp BamHI/StyI fragment was isolated from a 1.2% agarose gel via the Geneclean method and resuspended in 20 μl sterile doubledistilled water. This material was called fragment 3.

To generate the second fragment, pIG2mTNF DNA (8 μl=±5 μg) was cut with BamHI (40 Units, 10 Units/μl, Boehringer Mannheim) in a total volume of 80 μl buffer B (Boehringer Mannheim) for 3 hours at 37° C. The digested DNA was purified via the Geneclean method (Bio101, La Jolla) and resuspended in 68 μl of sterile doubledistilled water. To this volume 8 μl of 10 times concentrated buffer A (Boehringer Mannheim) and 40 Units SacI (Boehringer Mannheim, 10 U/μl) were added and again incubated for 3 hours at 37° C.

A 3071 bp SacI/BamHII fragment was isolated from a 1.2% agarose gel via the Geneclean method and resuspended in 40 μl sterile doubledistilled water. This material was called fragment 4.

To generate the mTNF-α Pro106 mutant pIG2mTNFP106A, 400 pmole (100 pmole/μl) of each of the synthetic oligos in a total volume of 10 μl were heated for 3' at 95° C., 10' at 65° C. and were subsequently allowed to

```
5'-CAAGGACGCTCCGGAGGGGGCTGAGCT-3'     27-mer     (SEQ ID NO 5)

3'-CTGCGAGGCCTCCCCCGAC-5'         19-mer     (SEQ ID NO 6)
       |_____|
        BspEI
```

Fragment 1 (5 μl), fragment 2 (1.5 μl) and the annealed oligos (10 μl) were mixed in a total volume of 19 μl ligation reach room temperature. The annealed oligos were subsequently placed on ice.

Fragment 3 (5 μl), fragment 4 (1.5 μl), and the annealed oligos (10 μl) were mixed in a total volume of 19 μl ligation buffer (Boehringer Mannheim). One Unit of T4 ligase (Boehringer Mannheim, 1 U/μl) was added and the mixture was incubated for 3 hours at 15° C. The ligation mixture was transformed to DH1(lambda) competent cells, plated out on tetracyclin containing LB plates and incubated at 37° C. Plasmid DNA was prepared from selected colonies and analyzed via restriction digestion (NarI, BamHI, StyI and SacI). A vector confirmed via restication analysis (pIG2mTNFP106A) was transformed to MC1061 (pAcI). This vector/host combination was further used for expression of the mTNFP106A mutein.

4. Construction of other tip mutated mTNF-α

4.1. Construction of pIG2mTNFE107A

In this construct, the Glu107 residue of mTNF was replaced with an Ala residue. In the course of the construction, a unique PstI restriction site was created in the mTNF coding sequence, which is not present in the wt mTNF sequence.

Construction of the vector was similar to the previously constructed mutants with the following differences:

fragment 1=911 bp BamHI/StyI fragment from pIG2mTNF fragment 2=3071 bp SacI/BamHI fragment from pIG2mTNF fragment 2=3071 bp SacI blunt/BamHI fragment from pIG2mTNF Blunting of the SacI site was done by cutting the pIG2mTNF vector with SacI, purifying the linear DNA via the gene clean method (resuspended in 20 μl distilled water). DNA in 20 μl water +3 μl of a 500 mM Tris-Cl pH 7.4, 5 mM MgCl2, 2 mM β-Me EtOH solution +1 μl dXTP solution 5 mM each +2 μl T4 polymerase (1 U/μl)

+4 μl doubledistilled water

The mixture specified above was incubated for 60 min at 37° C. followed by the purification of the blunted DNA via the gene clean procedure and digestion of the DNA with BamHI.

Oligos

4.3. Construction of pIG2mTNFE107A/E110A

In this construct, the Glu107 and Glu110 residues of mTNF were replaced with Ala residues. In the course of the Oligos

4.2. Construction of pIG2mTNFE110A mutant

In this construct, the Glu110 residue of mTNF was replaced with an Ala residue. In the course of the construction, a unique NarI restriction site was created in the mTNF coding sequence, which is not present in the wt mTNF sequence. Moreover, the unique SacI restriction site present in the wt mTNF sequence was destroyed.

Construction of the vector was similar to the previous constructed mutants with the following differences:

fragment 1=911 bp BamHI/StyI fragment from pIG2mTNF construction unique NarI and PstI restriction sites were created in the mTNF coding sequence, which were not present in the wt mTNF sequence. Moreover, the unique SacI restriction site present in the wt mTNF sequence was destroyed.

Construction of the vector was similar to the previous constructed mutants with the following differences:

fragment 1=911 bp BamHI/StyI fragment from pIG2mTNF fragment 2=3071 bp SacI blunt/BamHI fragment from pIG2mTNF Oligos

```
         K   D   T   P   A   G   A   A
5'-CAAGGACACCCCTGCAGGCGCCGCCCT-3'           27-mer    (SEQ ID NO 13)
      3'-CTGTGGGGACGTCCGCGGCGGGA-5'         23-mer    (SEQ ID NO 14)
```
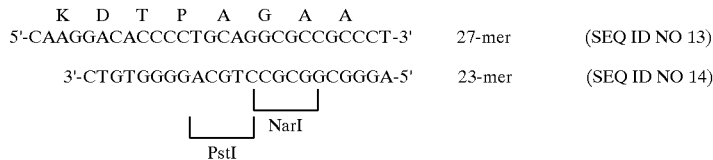

4.4. Construction of pIG2mTNFT105A/E110A

In this construct, the Thr105 and Glu110 residues of mTNF were replaced with Ala residues. In the course of the construction unique NarI and BSpEI restriction sites were created in the mTNF coding sequence, which were not present in the wt mTNF sequence. Moreover, the unique SacI restriction site present in the wt mTNF sequence was destroyed.

Construction of the vector was similar to the previous constructed mutants with the following differences:

fragment 1=911 bp BamHI/StyI fragment from pIG2mTNF fragment 2=3071 bp SacI blunt/BamHI fragment from pIG2mTNF Oligos

```
         K   D   A   P   E   G   A   A
5'-CAAGGACGCTCCGGAGGGCGCCGCCCT-3'           27-mer    (SEQ ID NO 15)
      3'-CTGCGAGGCCTCCCGCGGCGGGA-5'         23-mer    (SEQ ID NO 16)
```
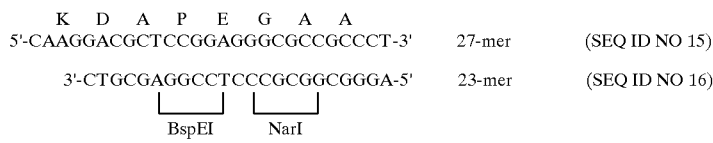

4.5. Construction of pIG2mTNFT105A/E107A

In this construct, the Thr105 and Glu107 residues of mTNF were replaced with Ala residues. In the course of the construction unique NciI and BsgI restriction sites were created in the mTNF coding sequence, which were not present in the wt mTNF sequence.

Construction of the vector was similar to the previous constructed mutants with the following differences:

fragment 1=911 bp BamHI/StyI fragment from pIG2mTNF fragment 2=3071 bp SacI/BamHI fragment from pIG2mTNF Oligos

4.6. Construction of pIG2mTNFT105A/E107A/E110A

In this construct, the Thr105, Glu107 and Glu110 residues of mTNF were replaced with Ala residues. In the course of the construction, unique EagI and SfiI restriction sites were created in the mTNF coding sequence, which were not present in the wt mTNF sequence. Moreover, the unique SacI restrictionsite present in the wt mTNF sequence was destroyed.

Construction of the vector was similar to the previously constructed mutants with the following differences:

fragment 1=911 bp BamHI/StyI fragment from pIG2mTNF fragment 2=3071 bp SacI blunt/BamHI fragment from pIG2mTNF Oligos

```
         K   D   A   P   A   G   A   E
5'-CAAGGATGCCCCGGCGGGTGCAGAGCT-3'           27-mer    (SEQ ID NO 17)
        3'-CTACGGGGCCGCCCACGTC-5'           19-mer    (SEQ ID NO 18)
```
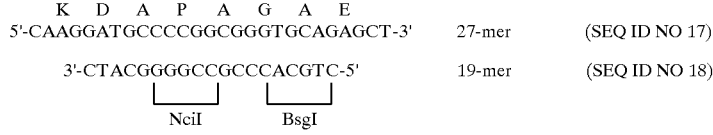

```
                                      K   D   A   P   A   G   A   A
                             5'-CAAGGATGCTCCGGCCGGTGCGGCCCT-3'       27-mer    (SEQ ID NO 19)
```

-continued

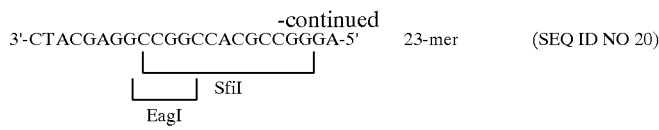
3'-CTACGAGGCCGGCCACGCCGGGA-5'  23-mer  (SEQ ID NO 20)

5. Construction of the tip-deleted mTNF-α or pIG2mTNF TPEGAE

In this construct, the TPEGAE coding sequence is deleted from the mTNF gene. In the course of the construction a unique NcoI restriction site was created in the mTNF coding sequence, which is not present in the wt mTNF sequence.

Construction of the vector was similar to the previously constructed mutants with the following differences:

fragment 1=911 bp BamHI/StyI fragment from pIG2mTNF fragment 2=3046 bp BstXI/BamHI fragment from pIG2mTNF Oligos

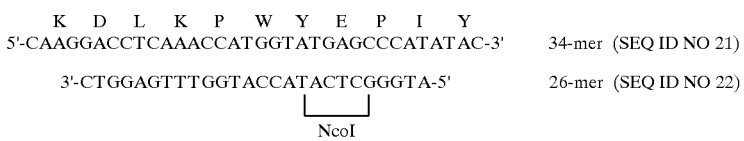
5'-CAAGGACCTCAAACCATGGTATGAGCCCATATAC-3'  34-mer  (SEQ ID NO 21)
3'-CTGGAGTTTGGTACCATACTCGGGTA-5'  26-mer  (SEQ ID NO 22)

The construction of additional tip-region deleted mTNF-α mutants also lies within the object of the present invention. These additional mutants are to be constructed using techniques known in the art as described above.

6. E. coli expression of wild type and tip-mutated or deleted mTNF-α.

Batch fermentations were conducted in LB medium (0.5% yeast extract, 1% bactotryptone, 0.5% NaCl), at a 15-liter scale, with a minimum dissolved oxygen content of 50%. pH was maintained constant during the whole fermentation at a value of 6.9. Foaming problems were avoided by adding 0.013% polypropylene glycol P2000.

Precultures of the different vector/host combinations were grown overnight in LB medium supplemented with tetracycline 0.001% for 18 hours at 28° C. After inoculation of the medium with a final $OD_{650}$ of 0.05, the bacteria were subsequently grown for 4 generations at 28° C., and for 4 hours at 42° C. At the end of the fermentation, the cells were separated from the medium by centrifugation, suspended in lysis buffer (10 mM KCl, 10 mM Tris-HCl, pH 6.8, 5 mM EDTA) and stored at −70° C.

7. Purification of recombinant wild-type and tip-mutated or deleted mTNF-α.

7.1 Purification of wild type mouse TNF-α

To the bacterial cell suspension, aminocaproic acid, PMSF and DTT are added to a final concentration of respectively 25 mM, 1 mM and 1 mM before lysing by French Press (14,000 psi, AMINCO, SLM Instruments, Urbana, USA). Subsequently, the suspension is centrifugated for 20 minutes at 16,500 rpm at 4° C. using a JA-20 rotor (Beckman). Wild-type mTNF-α is found in the supernatant fraction as assessed by SDS-polyacrylamide gelelectrophoresis (SDS-PAGE). Some of the TNF-α tip muteins were retrieved in the soluble and insoluble fraction. The described procedure is directed to the recovery of the mTNF-α material out of the soluble fraction. No attemps were made to purify and renaturate mTNF from the insoluble fraction. The nucleic acids in the supernatant were precipitated at pH 7.0 by the addition of polyethylene-imine to a final concentration of 0.4% followed by centrifugation by a JA-20 rotor for 20 minutes at 16,500 rpm at 4° C. mTNF-α or mutein protein were then enriched by a differential amoniumsulphate precipitation whereby a 40% step is followed by a second step at 65% saturation. mTNF-α or muteins remained in the 65% amonium sulphate pellet.

The pellet was resuspended in 25 mM Tris-HCl pH 7.2 and the conductivity of the solution was adjusted to 10 mS above the conductivity of the Phenyl sepharose column startbuffer (25 mM TrisHCl pH 6.9, 25% (NH4)2SO4). The material was then loaded at 0.5 cm/minute on the Phenyl Sepharose 4B matrix (Pharmacia) and washed with 8 column volumes of starting buffer. Proteins bound to the matrix were eluted with a linear salt gradient of 0% to 60% buffer B (20 mM ethanolamine, 10% ethylene glycol pH 9.0) over 6 column volumes.

The flow through fractions containing the mTNF-α protein were pooled and dialysed overnight against 25 mM Tris-HCl pH 7.2. After centrifugation, the material was loaded on Q Sepharose FF (Pharmacia) equilibrated against 25 mM Tris-HCl pH 7.2 at 1 cm/minute. The column was washed with 4 column volumes of starting buffer and eluted with a linear salt gradient form 0 mM to 300 mM NaCl in the same buffer followed by stepwise elution with 2 column volumes at 1 mM NaCl. Recombinant mTNF-α eluted at 300 mM NaCl.

By this procedure 98% pure mTNF-α could be obtained with a molecular mass of 17 kDa, as defined by SDS-PAGE under reducing conditions, and a specific activity of $\pm 2 \times 10^8$ U/mg as assessed by bioactivity on L929 cells.

7.2. Purification of P106A mTNFα mutein

Cell lysis, clearing and polyethylene imine treatment were performed as described in 7.1. In contrast to the physico chemical behaviour of wt mTNF, the P106A mutein was recovered in the PEI pellet. Therefore, the pellet was extracted with 20 mM Tris-Hcl, pH-7.0, 0,5 MNaCl (200 ml/pellet) and cleared by centrifugation (JA 20 rotor, 16 500 rpm, 20 min, 4° C.). The purification process ((NH4)2SO4 fractionation and chromatography steps on Phenyl Sepharose 4B and Q Sepharose FF) were identical to these described in the section 7.1 as for wt mTNF-α. Over 95% pure P106A mTNF-α was obtained by this procedure with a specific activity of $\pm 1.81 \times 108$ U/mg as assessed by bioassay on L-929 cells in the presence of Actinomycin D.

7.3. Purification of the T105A mTNFα mutein

Cell lysis, clearing and PEI treatment of the supernatans were performed as described in for wild type TNF-α. As for the P106A mutein, the T105A mTNF-α was recovered in the PEI pellet. Extraction and clearing were therefore performed as already described in section 7.2 for the P106A mutein.

The conductivity of the supernatant was adjusted to 10 mS above this of the equilibration buffer of the Phenyl Sepharose 4B column. The chromatographical conditions were identical to those described in section 7.1, except that an equivalent of a 5 liter cell culture was loaded on a 40 ml column. The T105A mTNF-α mutein was recovered in the first part of the gradient (about 0.9M→0,5M (NH4)2SO4). The pools of the 3 runs on Phenyl Sepharose 4B were mixed and after adjustment of the pH and the conductivity, the total pool was loaded on a 16 ml Phenyl Q Sepharose FF column. Chromatography conditions (flow rate (cm/h) and slope of the gradient) were kept identical as for these used on the previous Phenyl Sepharose 4B column.

Strongly enriched mTNF-α mutein was found in the flow through and wash as well as in the 100% B eluate (20 mM ethanol amine, 10% ethylene glycol, pH 9.0). All TNF-α containing fractions were collected and both pools were dialysed separately against 20 mM Tris-HCl, pH 7.2 and loaded on a Q Sepharose (Pharmacia), equilibrated with the same buffer. The chromatographical conditions were identical to those described as for wt mTNF-α (see section 7.1).

SDS PAGE under reducing conditions showed that from the Phenyl Sepharose 4B eluate a preparation of more then 95% pure T105A TNF material could be obtained with a specific activity of ±1×108 U/mg as assessed by bioassay on L929 cells in the presence of Actinomycin D.

7.4 Purification of tip deleted mTNF-α mutein (del mTNF-α)

Cell lysis, PEI treatment of the supernatant as well as the (NH4)2SO4 fractionation were identical as these described for the P106A mTNF-α mutein. The chromatography on Phenyl Sepharose 4B was identical to this described in 7.1 (wt MTNF) except that 7,5 cell culture equivalent was loaded on a 40 ml column (this means 2 runs instead of 4). The conductivity of the non-bound fraction of the phenyl sepharose runs was adjusted to 10 mS above this of the equilibration buffer of the Phenyl Sepharose 4B column and the material was loaded on a 10 ml TSK butyl 650M column (Merck) (flow rate: 1,5 cm/min; 10 mg protein/ml gel; protein quantification based on absorbance at 280 mm). The buffers for chromatography on TSK butyl 650M are identical to those used in the chromatography on Phenyl Sepharose 4B. After an extensive wash with equilibration buffer (12 column volumes), bound proteins were eluted by applying a linear gradient over 16 column volumes (100% A–100% B).

The non-bound protein fraction was dialysed against 25 mM Tris-HCl, pH 9.0 and applied at 1 cm/min on a Q Sepharose FF column (Pharmacia) (>5 mg protein/ml gel). Bound proteins were eluted at 1 cm/min by applying a linear salt gradient (0–300 mM NaCl), followed by a 300 mM NaCl wash (2 column volumes). SDS-PAGE shows that the del mTNF-α protein was found all over the eluate, but only the fractions eluting between 70–230 mM NaCl were pooled. These fractions were lacking the contaminating *E. coli* proteins with a molecular weight of about 14000, 15000 and 70000. The pooled fractions were diluted with the 25 mM Tris-HCl, pH 9.0 buffer and incubated for about 4 h at 4° C. Thereafter, the del mTNF-α pool was reloaded on the Q-sepharose FF column but now at a concentration <300 μg protein/ml gel (protein quantity based on absorbance at 280 nm). The wash and elution conditions were identical to these described for the first chromatography on Q Sepharose. The tip-deleted mTNF-α protein eluted in 2 well separated peaks with pure del mTNF-α protein in the second peak (elution at about 280 mM NaCl). The material has a specific activity of about 1×108 U/mg of protein as assessed by bioassay on L-929 cells in the presence of Actinomycin D.

7.5. Purification of the T105A-E107A mTNF-α double mutant

To the bacterial cell suspension, aminocapronic acid, PMSF and DDT weree added to a final concentration of respectively 25 mM, 1 mM and 1 mM before lysing by French Press (14,000 psi, AMINCO, SLM Instruments, Urbana, USA). Subsequently, the suspension was centrifugated for 20 minutes at 16,500 rpm at 4° C. using a JA-20 rotor (Beckman). The mTNF-α double mutant could be found back in the supernatant fraction as assessed by SDS-PAGE and therefore only this fraction was used for further purification. The nucleic acids in the supernatant were precipitated by the addition of polyethylene-immine to a final concentration of 0.4% followed by centrifugation for 20 minutes at 16,500 rpm at 4° C. The mTNF-α double mutant precipitated only partially after polyethylene imine treatment and was recovered from the pellet by introducing a washing step with 0.5 ml NaCl pH 7.2. Both fractions were then enriched by a differential amoniumsulphate precipitation whereby a 40% step is followed by a second step at 65% saturation. The mTNF-α mutein remained in the 65% amonium sulphate pellet.

The pellet was resuspended in 25 mM Tris-HCl pH 7.2 and the conductivity of the solution was adjusted to 10 mS above the conductivity of the Phenyl Sepharose 4B column startbuffer (25 mM TrisHCl pH 6.9, 25% (NH4)2SO4). The material was loaded at 0.5 cm/minute on the Phenyl Sepharose 4B matrix (Pharmacia) and washed with 8 column volumes of starting buffer. Proteins bound to the matrix were eluted with a linear salt gradient of 0% to 60% buffer B (20 mM ethanolamine, pH 9.0) over 6 column volumes.

The flow through fractions containing the mTNF-α double mutant protein were pooled and dialysed overnight against 25 mM Tris-HCl pH 7.2. After centrifugation, the material was loaded at 1 cm/minute on Q Sepharose FF (Pharmacia) equilibrated against 25 mM Tris-HCl pH 7.2. The column was washed with 4 column volumes of starting buffer and eluted with a linear salt gradient from 0 mM to 300 mM NaCl in the same buffer followed by stepwise elution with 2 column volumes of 300 mM NaCl and 2 column volumes of 1 mM NaCl. The mTNF-α double mutant eluted at 300 mM NaCl. A further purification was performed on a column of Fractogel TSK butyl 650M (Merck). To the protein solution, 25% (NH4)2SO4 was added and loaded on the column at a flow-rate of 1 cm/minute (3 mg/ml gel). The mTNF-α mutein protein was recovered in the flow through fraction and the proteins bound to the matrix were eluted with 10 column volumes of a linear gradient from 0% to 100%. As a final polishing step the T105A-E107A mTNF protein was purified by gel filtration on a Superdex 75 HR 10/30 column (Pharmacia) whereon it eluted as the second (or largest) protein peak with an apparent weight of 66 kD.

7.6 Purification of the T105A-E107A-E110A mTNF-α triple mutant

To the bacterial cell suspension, aminocapronic acid, PMSF and DDT was added to a final concentration of respectively 25 mM, 1 mM and 1 mM before lysing by French Press (14,000 psi, AMINCO, SLM Instruments, Urbana, USA). Subsequently, the suspension was centrifugated for 20 minutes at 16,500 rpm at 4° C. using a JA-20 rotor (Beckman). The mTNF-α mutein could be found back in the supernatant fraction as assessed by SDS-PAGE. The nucleic acids in the supernatant was then precipitated by the addition of polyethylene-imine to a final concentration of 0.4% followed by centrifugation for 20 minutes at 16,500 rpm at 4° C. The mTNF-α triple mutant was then enriched by a differential amoniumsulphate precipitation whereby a 40% step is followed by a second step at 65% saturation. mTNF-α or muteins remain in the 65% amonium sulphate pellet.

The pellet was resuspended in 25 mM Tris-HCl pH 7.2 and the conductivity of the solution was adjusted to 10 mS above the conductivity of the Phenyl Sepharose 4B column startbuffer (25 mM Tris-HCl pH 6.9, 25% (NH4)2SO4). The material was loaded at 0.5 cm/minute on the Phenyl Sepharose 4B matrix (Pharmacia) and washed with 8 column volumes of starting buffer. Proteins bound to the matrix were eluted with a linear salt gradient of 0% to 60% buffer B (20 mM ethanolamine, pH 9.0) over 6 column volumes. The fractions containing the mTNF-α triple mutant (this is the flow through and the 20 to 40% eluate fractions) were pooled and loaded on a TSK-C4 650M (Merck) at 1 cm/h (10 mg/ml) and washed with 8 column volumes of Phenyl Sepharose starting buffer. The proteins bound to the matrix were eluted with a linear gradient of 10 column volumes from 0% B to 100% B (20 mM ethanolamine pH 9.0).

The flow through fractions containing the mTNF mutein protein were pooled and loaded at a flow rate of 1 cm/min (5 mg/ml protein) on a Cu2+ IDA Sepharose fast flow column (Pharmacia) equilibrated against 20 mM sodium phosphate, 500 mM NaCl pH 6.8. The protein bounding to the matrix were eluted with a linear gradient from 0% to 70% B (20 mM sodium phosphate, 0,75M NH4Cl pH 7.8) during 10 column volumes, one column volume of 70% B and one column volume of 100% B. The protein of interest eluted in the 70% B fraction. The fractions were pooled and dialysed against 25 mM Tris-HCl pH 9,0.

The material was then loaded on a Q Sepharose FF (Pharmacia) column equilibrated against 25 mM Tris-HCl pH 7.2 at 1 cm/minute.

The column was washed with 4 column volumes of starting buffer and eluted with a linear salt gradient from 0 mM to 300 mM NaCl in the same buffer followed by stepwise elution with 2 column volumes of 300 mM NaCl. The triple mTNF-α mutant eluted at 250 mM NaCl.

EXAMPLE 2

The Trypanocidal Region of TNF-α Contains a Lectin-like Activity of the Molecule 1. Recombinant mTNF-α and hTNF-α are trypanocidal for *T. brucei brucei* and *T. brucei rhodesiense* and the effect is potentiated by cotreatement with LiCl Incubation of purified bloodstream forms of *T. brucei brucei* (FIG. 3A) and *T. brucei rhodesiense* (FIG. 3B) for 5 h with rm/hTNF-α results in the mortality of a part of the parasites: 50% of the animals are killed with 5000 pg/ml of rm/hTNF-α on *T. brucei brucei* and *T. brucei rhodesiense*. In the same assay, equal concentrations of hTNF-β, mouse interleukin 1α or mouse interleukin 1β do not cause any mortality of *T. brucei brucei* or *T. brucei rhodesiense* (data not shown). As shown in FIG. 4, this trypanocidal effect of TNF-α is potentiated 100-fold by co-treating the trypanosomes with 1 µg/ml of LiCl, demonstrating that not only the cytotoxic effect of TNF-α on tumor cells (Beyaert et al., 1989) but also the trypanocidal activity of the molecule is increased by LiCl.

2. The trypanocidal activity of mTNF-α in vitro is inhibited by preincubating TNF-α with a trypanosome lysate, whereas preincubation of the mTNF-α with the soluble p55 hTNF-α receptor protein does not block this effect Preincubation of the mTNF-α during 1h with different concentrations of a lysate from *T. brucei brucei* prepared as described in the materials section potently inhibits the mTNF-α trypanocidal effect (FIG. 5*a*), whereas the tumoricidal activity of mTNF-α on L929 cells is not affected (FIG. 5*b*).

On the other hand, preincubation of the mTNF-α during 1 h with 5 µg/ml of the soluble p55 hTNF-α receptor potently inhibits the mTNF-α tumoricidal activity against L929 cells, whereas the trypanocidal effect is hardly influenced (Table III). This result clearly demonstrates that the region responsible for the trypanocidal activity of the TNF-α molecule can be separated from the cellular p55 receptor binding domain on the TNF-α protein.

TABLE III

Inhibitory capacity of soluble p55 hTNF receptor on the mTNF-α tumoricidal and trypanocidal activity

| mTNF-α | Trypanocidal activity (% lysis) | | | Tumoricidal activiy (% lysis) | | |
|---|---|---|---|---|---|---|
| (pg/ml) | -p55 | +p55 | Δ | -p55 | +p55 | Δ |
| 100 | 30 ± 2 | 25 ± 3 | 15 ± 5 | 40 ± 2 | 0 ± 1 | 100 ± 5 |
| 1000 | 45 ± 5 | 41 ± 4 | 10 ± 4 | 92 ± 3 | 0 ± 1 | 100 ± 4 |
| 10000 | 60 ± 4 | 56 ± 3 | 7 ± 5 | 98 ± 4 | 93 ± 3 | 5 ± 2 |

TABLE III: Δ:% inhibition of activity by the addition of the p55 hTNF-α receptor protein
3. The TNF-α lectin-like region is probably involved in the trypanocidal activity of the protein As shown in FIG. 6A, preincubation of mTNF-α for 1 h with 1 µg/ml of N,N'-diacetylchitobiose, an oligosaccharide for which TNF-α has been shown to have a lectin-like affinity (Hession et al., 1987; Sherblom et al., 1988), results in a potent inhibition of the mTNF-α trypanocidal effect, whereas the mTNF-α tumoricidal activity as measured on L929 cells is not affected (FIG. 6B.)

Moreover, preincubation of the *T. brucei brucei* trypanosomes with lectins (added at a concentration of 10 µg/ml) that have a specificity for N,N'-diacetylchitobiose, such as *Urtica dioica* agglutinin and *Triticum vulgaris* agglutinin, also results in an inhibition of the mTNF-α trypanocidal activity, whereas lectins with a different specificity (and added at the same concentration of 10 µg/ml), such as *Galanthus nivalis* agglutinin and *Griffonia simplicifolia* A4, did not have any effect upon preincubation with the mTNF-α (Table IV). Moreover, none of these lectins had any effect on the tumoricidal activity of TNF-α on L929 cells.

These results strongly suggest that the TNF-α lectin-like region is involved in the trypanocidal, but not in the tumoricidal activity.

TABLE IV

Inhibitory capacity of different lectins on mTNF-α
mediated trypanocidal activity against *T. brucei brucei*

| mTNF-α (pg/ml) | % inhibition of trypanocidal activity | | | |
|---|---|---|---|---|
| | WGA | UDA | GNA | GSI-A4 |
| 100 | 70 ± 4 | 80 ± 2 | 0 ± 1 | 0 ± 2 |
| 1.000 | 63 ± 5 | 63 ± 3 | 5 ± 3 | 0 ± 2 |
| 10.000 | 13 ± 5 | 29 ± 5 | 5 ± 2 | 2 ± 1 |
| 100.000 | 5 ± 3 | 3 ± 2 | 3 ± 2 | 0 ± 2 |
| 1.000.000 | 7 ± 5 | 2 ± 1 | 2 ± 1 | 0 ± 1 |

WGA: *Triticum vulgaris* agglutinin
UDA: *Urtica dioica* agglutinin
GNA: *Galanthus nivalis* agglutinin
GSI-A4: *Griffonia simplicifolia* A4
All lectins were added at the concentration of 10 μg/ml

EXAMPLE 3

The Tip Region of Mouse and Human TNF-α
Contains the Trypanocidal Activity and Lectin-like
Activities of the Molecule and is Involved in the
TNF-induced Lethal Shock 1. Design of the TNF-α-derived peptides The biotinylated tip peptides, inspired on the sequence spanning amino acid positions 100 to 116 of hTNF-α (Pennica et al., 1984) and mTNF-α (Fransen et al., 1985) were synthesized as indicated in the materials and methods section. Subsequently, the peptides were analyzed using a C18 reversed phase HPLC column. Analysis of the three-dimensional structure of the TNF-α molecule upon consulting the Brookhaven data base demonstrated that the identified epitope is located at the tip of the molecule. This location is interesting considering the fact that TNF-α was shown to be active in a membrane-bound form (Kriegler et al., 1988). The following substitutions in both m/hTNF-α tip regions were made: P(100) by C, C(101) by G, and E(116) by C. It should be noted that the wild-type sequence of TNF-α contains a Cys residue at location 101. In order to prevent inopportune closing of the loop with this Cys(101), resulting in an unwanted conformation, the Cys 101 residue was mutated to a Gly. It has been demonstrated that this mutation did not affect the cytotoxic activity of native TNF-α, indicating that this amino acid is not involved in the TNF-receptor binding (Arakawa et al., 1990). Furthermore, native TNF-α as well as the tip peptide exert a trypanocidal activity as assayed by trypanosome survival in the in vitro assay. An overview of all the peptides synthesized is given in Table V below.

TABLE V

Overview of synthetic TNF-α tip region peptides.

| mTNFα-tip | Bio-GG-CGPKDTPEGAELKPWYC | (SEQ ID NO 24) |
|---|---|---|
| hTNFα-tip | Bio-GG-CGQRETPEGAEAKPWYC | (SEQ ID NO 25) |
| subpep 1 | Bio-GG-C - - - - TPEGAE - - - - - C | (SEQ ID NO 26) |
| subpep 2 | Bio-GG - - - - - - - - EGAELKPWY - | (SEQ ID NO 27) |
| subpep 3 | Bio-GG - - - - - - TPE - - - - - - - - - | (SEQ ID NO 28) |
| subpep 4 | Bio-GG-c - - - - tpeGae - - - - - c | (SEQ ID NO 29) |
| mutpep 1 | Bio-GG-C - - - - APEGAE - - - - - C | (SEQ ID NO 30) |
| mutpep 2 | Bio-GG-C - - - - TAEGAE - - - - - C | (SEQ ID NO 31) |
| mutpep 3 | Bio-GG-C - - - - TPAGAE - - - - - C | (SEQ ID N6 32) |
| mutpep 4 | Bio-GG-C - - - - TPEAAE - - - - - C | (SEQ ID NO 33) |
| mutpep 5 | Bio-GG-C - - - - TPEGAA - - - - - C | (SEQ ID NO 34) |

The sequences are given in the one letter amino acid code. The amino acids in the L or D configuration are anotated in the one letter code in capitals or in small letters, respectively. The annotation Bio-GG- denotes Biotin-Gly-Gly.

2. The synthetic mTNF-α tip peptide is directly trypanocidal in vitro, an effect that can be inhibited by preincubation of the peptide with N,N'-diacetylchitobiose To prove that the tip region of mTNF-α is directly implicated in its trypanocidal and its lectin-like effect, experiments were designed to test (i) whether the synthetic mTNF-α-tip peptide has any trypanocidal activity in vitro and (ii) if so, whether this activity can be inhibited by preincubating the peptide with N,N'-diacetylchitobiose. As shown in FIG. 7, the mTNF-α-tip peptide indeed shows a trypanocidal activity against bloodstream forms of *T. brucei brucei*, whereas it exerts no tumoricidal activity on L929 cells when tested in a similar dose response curve (data not shown). The hTNF-α-tip peptide shows similar results (FIG. 7). In the in vitro trypanocidal assay, h/mTNF-α has a specific activity of $2 \times 10^5$ U/mg of protein, while the peptide exerts its activity with an average specificity of $4 \times 10^2$–$4 \times 10^3$ U/mg of peptide.

Interestingly, the trypanocidal activity of the peptide can also be inhibited by preincubating it for 1 h with 1 μg/ml of N,N'-diacetylchitobiose (FIG. 7), demonstrating that the tip region of h/mTNF-α (from amino acid position 100 to 116) is involved in its trypanocidal and its lectin-like activity.

3. The short tip peptide, Thr Pro Glu Gly Ala Glu (SEQ ID NO 23), contains the trypanocidal activity of TNF-α and is linked with the described lectin-like activity of the protein since it can be inhibited by preincubation with N,N'-diacetylchitobiose The fact that both human and mouse TNF-α peptides exert in vitro trypanocidal activity with no significant differences in specific activity also implies that the amino acids which are common to the human and the mouse TNF-α tip region can be involved in the trypanocidal activity. This hypothesis was further investigated by testing the trypanocidal activity of two subpeptides of the tip region containing sequences similar to both species. The subpeptide 1, which consists of the positions T(105), P(106), E(107), G(108), A(109) and E(110) which are identical in m/hTNF-α still had full trypanocidal activity (FIG. 8), whereas subpeptide 2 which encompasses the positions E(107) to Y(115) of mTNF-α (with only L(111) different from hTNF-α) showed strongly reduced trypanocidal activity (FIG. 9). These results strongly suggest that the trypanocidal and, thus, perhaps also the lectin-like activity of TNF-α, is at least partially mediated by amino acid position T(105) to E(110), in which especially positions T(105) and/or P(106) seem(s) to be of the utmost importance. The trypanocidal activity of the different mutant peptides 1, 2, 3, 4 and 5 of h/mTNF-α was measured, wherein positions 105, 106, 107, 108 or 110 of the TPEGAE peptide were replaced consecutively by an A. The mutant peptides in which the T(105) or E(107) or E(110) was replaced by an A lost their trypanocidal activity, while the two other mutants were fully or even more active (FIG. 8 and 9).

Comparison of the trypanocidal activity of the fully active TPEGAE peptide with the synthetic oligopeptide tpeGae wherein the L amino acids were replaced by D residues demonstrated the stereospecificity of the TNF-α tip peptide trypanosome interaction since the latter peptide had lost its activity (FIG. 8).

EXAMPLE 4

Antibodies Raised against the Tip Region of Mouse
and Human TNF-α Inhibit the Trypanocidal
Acitivity and the Septic Shock Effects but not the
Tumoricidal Activity of TNF-α.

1. Generation of rabbit anti-tip mTNF-α and hTNF-α polyclonal antibodies

Polyclonal antibodies against the mTNF-α and hTNF-α-derived tip peptides were produced as follows: On day 0, rabbits were injected subcutaneously with 50 μg of a complex existing of 7 μg of the biotinylated tip peptide and 43 μg of avidin (Neutralite, Eurogentec, Belgium) dissolved in complete Freund's adjuvant (total volume: 1 ml) (Difco Laboratories, Detroit, Mich., USA). On day 21, rabbits were injected subcutaneously with 50 μg of the same complex dissolved in incomplete Freund's adjuvant (total volume: 1 ml). On day 42, the rabbits were injected subcutaneously with 100 μg of the avidin-tip peptide complex in 1 ml of PBS. On day 52, the rabbits were bled, and the sera which reacted positively in ELISA with both the synthetic h/mTNF-α tip peptide bound to streptavidin and with the native h/mTNF-α molecule, were purified on Protein G Sepharose CL4B (Sigma, St. Louis, Mo., USA) essentially as proposed by the supplier. The IgG concentration was assessed by the Bradford assay.

2. Generation of anti-tip mTNF-α monoclonal antibodies 2.1. Immunization

Balb/c mice were immunized with 100 μg of avidine-biotine-TNF-α tip peptide conjugates emulsified in complete Freund's adjuvant. Three weeks later the same animals were challenged with 400 μg of avidin. Biotin-TNF-α tip peptide conjugates emulsified in incomplete Freund's adjuvant. Another three weeks later, the mice were boosted with 10 μg of avidin-biotin-TNF-α tip peptide conjugates dissolved in PBS. Three days later the spleen cells were fused to generate monoclonal antibodies.

2.2. Fusion and Screening

Approximately $10^8$ spleen cells of immunized Balb/c mice were fused with the universal B cell fusion partner NSO via the PEG-fusion protocol (Galfré and Milstein, 1981). Positive hybridomas were identified via an ELISA screening on ELISA plates coated with TNF-α. The thus obtained anti-TNF-α tip monoclonal antibodies did not neutralize the tumoricidal activity of TNF-α.

3. Differential inhibition of the trypanocidal and the tumoricidal activities of mTNF-α by monospecific polyclonal anti-mTNF-α tip peptide antibodies or monoclonal mTNF-α anti-tip antibodies.

Preincubation of mTNF-α for 1 h at room temperature with 10 μg/ml of protein G-sepharose-purified rabbit-anti-rmTNF-α tip peptide polyclonal antibodies or with a mouse anti-rmTNF-α tip peptide monoclonal antibody results in a strong inhibition of the mTNF-α-mediated trypanocidal effect (FIG. 10), whereas only a weak inhibition of the mTNF-α-mediated tumoricidal effect on L929 cells was detected (data not shown).

The results stress once more that this region of the TNF-α molecule is directly involved in the trypanocidal and in the lectin-like activity of TNF-α.

4. Anti-mTNF-α tip polyclonal antibodies can inhibit LPS-induced septic shock in vivo Sherblom et al. (1988) have shown that TNF-α has a lectin-like affinity for the glycoprotein uromodulin. Interestingly, this glycoprotein is able to potently inhibit the LPS-induced shock in vivo, whereas it does not block the tumoricidal activity of TNF-α on L929 cells in vitro. The authors suggested therefore that the lectin-like region of TNF-α is implicated in the toxic effects of TNF-α in septic shock, but not in its tumoricidal activity on L929 cells. Since the TNF-α tip region is involved in the lectin-like activity of TNF-α, as demonstrated in the previous sections, the effect of the rabbit anti-mTNF-α tip polyclonal antibodies on LPS-induced septic shock in vivo was investigated. As shown in Table V, intraperitoneal injection of Balb/C mice (10 mice/group) with 100 μg of protein G-purified anti-tip polyclonal antibodies, 2 h before the injection of the lethal dose of 500 μg of LPS/mouse, resulted in an increased survival time as compared with the control mice that only received PBS or an irrelevant control polyclonal antibody preinjection (control IgG).

This result indicates that (pre)treatment of the animal with anti-m/hTNF-α tip antibodies can protect the animal from the lethal effects of the septic shock syndrome.

TABLE VI

Effect of lethal dose of LPS on survival time of mice

| days post injection | mortality (%) | | |
|---|---|---|---|
| | PBS | anti-tip | control IgG |
| 0 | 0 | 0 | 0 |
| 1 | 40 | 0 | 40 |
| 2 | 100 | 20 | 100 |
| 3 | 100 | 50 | 100 |
| 4 | 100 | 80 | 100 |
| 5 | 100 | 80 | 100 |
| 6 | 100 | 100 | 100 |

EXAMPLE 5

Tip-mutated or Tip-deleted TNF-α is not Hampered in its in vitro cytolytic/cytotoxic Activity and has a Reduced Lethal Effect 1. Recombinant and mutated mTNF-α and hTNF-α are cytotoxic to L-929 cells in vitro.

The purified recombinant mTNF-α and hTNF-α, produced in *E. coli*, had a specific activity of respectively, 2–3 $10^8$ Units/mg and 2–4 $10^7$ Units/mg as tested on specific cell lysis of L-929 cells in the 18 hours assay in the presence of Actinomycin D.

The mTNF-α tip-mutations or -deletion did not hamper the in vitro cytolytic activity of the molecule (FIG. 11).

2. T(105), E(107), and/or E(110) mutated or tip deleted TNF-α has lost the mTNF-α trypanocidal activity.

The T(105), E(107), and/or E(110) mutants, combinations of these and deletions of the TPEGAE human or mouse TNF-α tip domain result in a significant loss of mTNF-α trypanocidal activity (FIG. 12). It is to be remarked in this context that, mutation of the P(106) and/or G(108) in the tip peptide to A did not change the trypanocidal nor the cytolytic activity of TNF-α (data not shown).

3. T(105), E(107) and/or E(110) tip-mutated or tip-deleted mTNF-α has a lower LD50 value then wild type mTNF-α.

Wild type mTNF-α is lethal for C57BL/6 mice at a dose of 10 μg/mouse. It was tested if those mutations hampering the trypanocidal activity of mTNF-α (which could in previous examples be correlated with the lectin-like activity of the molecule) had any influence on the LD50 of the protein. As these TNF-α muteins of the present invention exert the same cell cytotoxic activity as wild type TNF-α and as this effect is directly linked with the in vivo tumoricidal activity of the cytokine, the TNF-α muteins of the invention could be useful as anti-tumor agens without the nefast toxic side effects of TNF-α. Moreover, any activity of TNF-α that could be linked with its lectin-like activity, such as induction of the septic shock syndrome, cachexia, the damage to endothelial cells, etc., could then be circumvented by using the above described TNF-α muteins.

FIG. 13 shows the survival rate of intravenously injected C57BL/6 mice when treated with 10 μg, 5 μg, 2.5 μg or 1

μg/mouse of either wild type mTNF-α or T105A mTNF-α (6 mice/group). At the the dose of 5 μg/mouse a differential effect of the wild type and the T105A mTNF-α could be observed.

EXAMPLE 6

The Tip Region of the TNF-α Molecule has an Effect on the in Vivo Half Life of the Molecule Since lectin-carbohydrate interactions may modulate the clearance of a protein, the effect of mutations in the tip region in vivo half life of the molecule was tested. Female 8 weeks old C57bL/6 mice (6 mice/group—Charles Rivers Deutshland) were injected intraperitoneally with 1 μg/mouse of either wild type mouse TNF-α or tip deleted TNF-α. Subsequently, the mice were bled 0.5, 5, 10, 15, 30, 60, 120, 180, or 240 minutes post-injection. The sera were tested for mTNF-α contents in the L-929 cytotoxic assay and in the indirect ELISA assay as detailed in the materials and methods sections detecting both wild type and tip mutated mouse TNF-α with the same sensitivity. The results of 2 experiments are given in Table VII below.

These experiments demonstrate a significant longer half life (at least 2 fold longer half life) for the tip deleted TNF-α mutant than for the wild type, TNF-α molecule.

TABLE VII

In vivo half life of mouse wild type and tip-deleted TNF-α.

| time post injection | concentration TNF-α (ng/ml) | |
|---|---|---|
| (minutes) | wild type TNF | tip deleted TNF |
| Experiment 1 | | |
| 0.5 | 1000 | 1000 |
| 5 | 880 | 990 |
| 10 | 650 | 640 |
| 15 | 500 | 550 |
| 30 | 420 | 580 |
| 60 | 320 | 450 |
| 120 | 20 | 250 |
| 180 | 10 | 100 |
| 240 | 0 | 10 |
| Experiment 2 | | |
| 0.5 | 1000 | 1000 |
| 15 | 550 | 600 |
| 30 | 500 | 500 |
| 60 | 480 | 500 |
| 120 | 20 | 330 |
| 180 | 0 | 240 |
| 240 | 0 | 20 |

EXAMPLE 7

The Tip Region of the TNF-α Molecule is Involved in the Induction of Endothelial Cells to Produce Inflammatory Cytokines 1. Tip-mutated TNF-α induces less human interleukin-6 (IL6) on human microvascular enothelial cells of the brain than wild type TNF-α

Human microvascular endothelial cells of the brain (hMVECb) are prepared as described by Grau and Lou (1993).

The cells were plated in 24 well plates at 106 cells/ml and treated for 24 hours with various doses of wild type or tip-muted TNF-α. Subsequently, the IL6 concentration in the supernatant of the cells was assessed using a commercially available hIL6 ELISA kit (Medgenix, Belgium). The results (shown in Table VIII) demonstrate that tip mutated TNF is less capable of inducing the endothelial brain cells to produce IL6.

TABLE VIII

IL6 production (pg/ml) by hMVECb cells by treatment with wild type mouse TNF-α or tip mutated mTNF-α

| | IL6 concentration (pg/ml) | |
|---|---|---|
| pg/ml | experiment 1 | experiment 2 |
| wt mTNF: 0 | 620 | 800 |
| 333 | 1520 | 1900 |
| 1000 | 1250 | 1400 |
| 1666 | 1220 | 1300 |
| del mTNF: 0 | 620 | 800 |
| 333 | 760 | 850 |
| 1000 | 1180 | 1600 |
| 1666 | 1240 | 1900 |
| T105A mTNF: 0 | 620 | 800 |
| 333 | 560 | 700 |
| 1000 | 1080 | 1300 |
| 1666 | 980 | 1250 |
| P106A mTNF: 0 | 620 | 800 |
| 333 | 720 | 1300 |
| 1000 | 560 | 750 |
| 1666 | 800 | 1300 |

2. The T105A and the P106A mTNF-α mutants induce less human interleukin 8 (IL8) than wild type TNF-α on human endothelial brain cells The conditioned medium of 106 hMVECb cells/ml treated for 24 hours with different doses of wild type or tip mutated TNF-α was analyzed on IL8 production using a commercially available human IL8 ELISA detection kit (Medgenix, Belgium). The results, shown in Table IX below, demonstrate that the T105A and P106A mutants are inducing about 3 fold less IL8 in these cells than wild type TNF-α while the tip deletion mutant was about two times more powerful in inducing the inflammatory cytokine IL8.

TABLE IX

IL8 production (pg/ml) by hMVEC6 cells by treatment with wild type mouse TNF-α or tip mutated mTNF-α

| | IL8 concentration (pg/ml) | |
|---|---|---|
| pg/ml | experiment 1 | experiment 2 |
| wt mTNF: 0 | 40 | 80 |
| 333 | 1050 | 1700 |
| 1000 | 1680 | 1800 |
| 1666 | 1200 | 1650 |
| del mTNF: 0 | 40 | 80 |
| 333 | 1800 | 2450 |
| 1000 | 1300 | 2200 |
| 1666 | 850 | 1250 |
| T105A mTNF: 0 | 40 | 80 |
| 333 | 600 | 750 |
| 1000 | 800 | 1250 |
| 1666 | 380 | 500 |
| P106A mTNF: 0 | 40 | 80 |
| 333 | 300 | 400 |
| 1000 | 1100 | 1500 |
| 1666 | 250 | 900 |

EXAMPLE 8

The Tip Region of TNF-α is Involved in the Metastatis-promoting Effect of the Molecule Besides the wall defined anti-tumor effect of TNF-α, experiments concerning the influence of exogenous TNF-α on metastis has been a point of discussion. In a murine fibrosarcoma model (Tomazic et al., 1988), a lung cancer model (Shultz and Atlom, 1990) and in melanoma models (Sylvester et al, 1990; Lollini et al., 1990) inhibition of formation of metastases by recombinant human TNF-α has been reported when the latter was given within 3 days of tumor cell inoculation. On the other hand, administration of recombinant human TNF-α led to an increase of pulmonary metastasis when given 1 hour prior to the intravenous inoculation of a human melanoma cell line into nude mice (Giavazzi et al., 1990) or promoted the implantation of human ovarian cancer xenografts in the peritoneal cavity of nude mice (Malik et al., 1989).

The metastasis-promoting effect of wild type and tip deleted mouse TNF-α was compared by use of the 3LL-R tumorigenic Lewis lung carcinoma cell line (wt and del mTNF-resistant Lewis lung carcinoma) (Remels et al., 1989). Thereto, 8 weeks old female C57bl/6 mice (5 mice/ group) (Charles River, Deutschland) were injected intraperitoneally with either PBS (control group) or 5 μg of wild type or tip-deleted mouse TNF-α per mouse, 5 hours prior to the intravenous injection of 2.106 3LL-R cells. This tumor inoculum normally leads to a 100% mortality 25 days after injection of the control group. After 17 days, the mice injected with wt mTNF/3LL-R all suffered from severe respiration problems whereas the mice in the del mTNF/ 3LL-R group looked significantly better and the mice in the PBS/3LL-R group looked completely healthy. At this time, all mice were killed and the lung weight as well as the amount of cancer cell nodules in the lung was assessed. The results are shown in Table X below. The weight of the lungs as well as the number of nodules present in the lungs was significantly higher (at least 100x) in the TNF-α treated mice indicating that TNF-α indeed is capable of enhancing the metastatic potential of TNF-resistant tumor cells. However, the metastatic enhancing potential of the TNF tip deletion mutant lays considerably lower than that of wild type TNF.

The observed metastasis-promoting effect for TNF-α might reside in an influence of TNF-α on the interaction of circulating tumor cells with the endothelium supporting the arrest, diapedesis and extravasation of tumor cells. As the tip-deleted TNF-α protein has significantly less metastasis promoting capacity than wild type TNF-α, the tip region of the molecule may interfere with the interaction of TNF-α with the endothelium. This interaction can be due to the enhanced expression of adhesion molecules on endothelial cells and/or tumor cells by a direct action of TNF-α on these cells or being mediated via additional cells e.g. granulocytes or platelets.

TABLE X

Experimental metastasis inducing capacity of wild type and tip deleted TNF-α on TNF resistant 3LL-R lewis Lung carcinoma cells.

| treatment | mean lung weight | # nodules in lung |
|---|---|---|
| control/3LL-R | 153 | 0 |
| PBS/3LL-R | 141.6 ± 11.3 | 0.2 ± 0.4 |
| wt mTNF/3LL-R | 1088.2 ± 315.7 | >50/>50/>50/>50/>50 |
| del mTNF/3LL-R | 566 ± 318 | >50/>50/40/20/20 |

REFERENCES

Aggarwal B, Eessalu T, Hass P (1985) Characterization of receptors for human tumor necrosis factor and their regulation by gamma-interferon. Nature 318:665–667.

Androlewicz A, Browning J, Ware C (1992) Lymphotoxin is expressed as a heteromeric complex with a distinct 33-kDa glycoprotein on the surface of an activated human T-cell hybridoma. J Biol Chem, 267:2542–2547.

Amiri P, Locksley R, Parslow T, Sadick M, Rector E, Ritter D, Mc Kerrow J (1992). Tumor necrosis factor α restores granulomas and induces parasite egg-laying in schistosome-infected SCID mice. Nature 356:604–607.

Arakawa T, Visger J, McGinley M, Rohde M, Fox G, Narhi L (1990). Alteration in folding efficiency and conformation of recombinant human tumor necrosis factor alpha by replacing cystein 69 and 101 with aspartic acid 69 and arginine 101. Prot Eng 3:724–724.

Atherton & Shepard (1989) in "Solid phase peptide synthesis" IRL Press, Oxford

Beutler B, Cerami A (1987) Cachectin: more than a tumor necrosis factor New Engl J Medicine 316:379

Beutler B, Cerami A (1989) The biology of cachectin/ TNF—a primary mediator in the host response. Ann Rev Immunol 7:625–655.

Beutler B, Greenwald D, Hulmes J, Chang M, Pan Y, Mathison J, Vlevitch R, Cerami A (1985). Identity of tumor necrosis factor and the macrophage-secreted factor cachectin. Nature 316:552–554.

Beyaert R, Vanhaesebroek B, Suffys P, Van Roy F, Fiers W (1989) Lithium chloride potentiates TNF-mediated cytotoxicity in vitro and in vivo. Proc Natl Acad Sci USA 86:9494–9498.

Blalock J (1990) Complementarity of peptides specified by 'sense' and 'antisense' strands of DNA. Trends Biotechnol 8:140–144.

Carswell E, Old L, Kassel R, Green S, Fiore N, Williamson B (1975) An endotoxin induced serum factor that causes necrosis of tumors. Proc Natl Acad Sci USA 72: 3666–3670

Cerami A, Beutler B (1988). The role of cachectin/TNF in endotoxic shock and cachexia. Immunol Today 9:28–31.

Clark I (1987). Cell mediated immunity in protection/ pathology of malaria. Parasit Today 3:300–305.

Clark I, Hunt N, Butcher G, Cowden W (1987). Inhibition of murine malaria (*Plasmodium chabaudi*) in viva by recombinant interferon-λ or tumor necrosis factor and its enhancement by butylated hydroxyanisole. J Immunol 139:3493–3496.

Cumming D (1991). Glycosylatin of recombinant protein therapeutics: control and functional implications. Glycobiology 1:115–130.

Dembic Z, Loetscher H, Gubler U, Pan Y, Lahm H, Gentz R, Brockhaus M, Lesslauer W (1990) Cytokine 2: 231–237

Duchosal A, Eming S, Fischer P (1992). Immunization of hu-PBL-SCID mice and the rescue of human monoclonal Fab fragments through combinatorial libraries. Nature 355:258–262.

Eck M, Ultsch M, Rinderknecht E, De Vos A, Sprang S (1992) The structure of human lymphotoxin at 1.9-A resolution J Biol Chem 267: 2119–2122

Galfré G, Milstein C (1981) Preparation of monoclonal antobodies: strategies and procedures. Methods Enzymol 73:3–46.

Giavazzi R, Garofolo A, Bani M, Abbate M, Ghezzi P, Boraschi D, Mantovani A, Dejana E (1990) Interleukin-1-induced augmentatio, of experimental metastases from a human melanoma. Cancer Res 50:4771.

Fransen L, Mueller R, Marmenout A, Tavernier J, Van Der Heyden J, Kawashima E, Chollet A, Tizard R, Van Heuverswijn H, Van Vliet A, Ruysschaert M, Fiers W (1985)

Molecular cloning of mouse tumor necrosis factor cDNA and its eukaryotic expression. Nucl Acid Res 13:4417–4429.

Ghiso J, Saball E, Leoni J, Rostagno A, Frangion (1990) Binding of cystatin C to C4: the importance of antisense peptides in their interaction. Proc Natl Acad Sci USA 87:1288–1291.

Grau G, Piguet P, Vassalli P, Lambert P (1989). Tumor necrosis factor and other cytokines in cerebral malaria: experimental and clinical. Imm Rev 112:49–70.

Grau G, Lou J (1993) TNF in vascular pathology: the importance of platelet-endothelium interactions. Research in Immunology 155:355–363.

Gray P (1987) Molecular characterisation of human lymphotoxin. In Lymphokines 13, Eds. D. R. Webb and D. V. Goeddel, Acad. Press, p. 199–208.

Hart I, Fiddler I (1980) Role of organ selectivity in the determination of metastatic patterns of B16 melanoma Cancer Res 40: 2281–2287

Hession C, Decker J, Sherblom A, Kumar S, Yue C, Mattaliono R, Tizard R, Kawashima E, Schmeissner U, Heletky S, Chow E, Burne C, Shaw A, Muchmore A (1987). Uromodulin (Tamm-Horsfall glycoprotein): a renal ligand for lymphokines. Science 237:1479–1484.

Kongshavn P, Ghadirian E (1988). Enhancing and suppressive effects of tumor necrosis factor/cachectin on growth of *Trypanosoma musculi*. Parasite Immunol 10:581–588.

Kriegler M, Perez C, DeFay K, Albert I, Lu S (1988) A novel form of TNF/cachextin as a cell surface cytotoxic transmembrane protein: ramifications for the complex physiology of TNF. Cell 53:45–33.

Liew F, Parkinson C, Millot S, Severn A, Carrier M (1990). Tumour necrosis factor (TNF-α) in leishmaniasi. I. TNFA mediated host protection against cutaneous leishmaniasis. Immunology 69:570–573.

Loetscher H, Pan Y, Lahm H, Gentz R, Brockhaus M, Tabuchi H, Lesslauer W (1990) Molecular cloning and expression of the human 55kd tumor necrosis factor receptor. Cell 61: 351–359.

Lollini P, deGiovanni C, Nicoletti G, Bontadini P, Tazzari L, Landuzzi K, Scotlandi K, Nanni P (1990) Enhancement of experimental metastatic ability by tumour necrosis factor alone or in combination with interferon-gamma. Clin and Exp Metastasis 8:215.

Lucas R, Heirwegh K, Neirinck A, Remels L, Van Heuverswijn H, De Baetselier P (1990). Generation and characterisation of a neutralising rat-anti-rmTNF-α monclonal antibody. Immunology 71: 218–223.

Malik S, Griffin D, Fiers W, and Balkwill F (1989) Paradoxical effects of tumor necrosis factor in experimental ovarian cancer Int J Cancer 44:918.

Manogue K, Cerami A (1988) In: Cellular and Molecular aspects of Inflammation (eds G. Poste and S. T. Crooke), Plenum Press, New York, pp 123–150

Marmenout A, Fransen L, Tavernier J, Van Der Heyden J, Tizard R, Kawashima E, Mueller R, Ruysschaert R, Van Vliet A, Fiers W (1985) Molecular cloning and expression of human tumor necrosis factor and comparison with mouse tumor necrosis factor. Eur J Biochem 152:515–522.

Mathison J, Wolfson E, Ulevitch R (1988). Participation of tumor necrosis factor in the mediation of gram negative bacterial lipopolysaccharide-induced injury in rabbits. J Clin Invest 81:1925–1937.

Old L (1985) Tumor necrosis factor (TNF). Science 230: 630–632.

Okusawa S, Gelfand J, Ikejima T, Connolly R, Dinarello C (1988). Interleukin-1 induces a shock-like state in rabbits. Synergism with tumor necrosis factor and the effect of cyclooxygenase inhibition. J Clin Invest 81:1162–1172.

Orosz P, Echtenacher B, Falk W, Rüschoff J, Weber D, Mannel D (1993) Enhancement of experimental metastasis by tumor necrosis factor. J Exp Med 177:1391–1398.

Pennica D, Nedwin G, Hayflick J, Seeburg P, Derynck R, Palladino M, Kohr W, Aggarwal B, Goedel D (1984) Human tumor necrosis factor: precursor structure, expression and homology to lymphotoxin. Nature 312:724–729.

Pennica D, Hayflick J, Bringman T, Palladino M, Goedel D (1985) Cloning and expression in *Escherichia coli* of the cDNA for murine tumor necrosis factor. Proc Natl Acad Sci USA 82:6060–6064.

Perrson M, Caothien R, Burton D (1991). Generation of diverse high affinity human monoclonal antibodies by repertoire cloning. Proc Natl Acad Sci USA 88:2432–2436.

Remels L, Neirinck A, Brys L, Vercauteren E, De Baetselier P (1989). TNF-α mediated selection of macrophage-resistant gene-regulatory tumor variants. Clin Exp Metastasis 7:493–506.

Rink (1987) Tetrahedron Lett 28:3787.

Roubos E (1990) Sense-antisense complementarity of hormone-receptor interaction sites. Trends Biotechnol 8:279–281.

Rouzer C, Cerami A (1980). Hypertriglyceridemia associated with Trypanosoma brucei infection in rabbits: role of defective triglyceride removal. Mol Biochem Parasitol, 2:31–38.

Sato et al, (1986) J Natl Cancer Inst 76: 1113

Schlutz R, Altom M (1990) Protective activity of recombinant murine tumor necrosis factor-α and interferon-gamma against experimental murine lung carcinoma metastases. J Interfern Res 10:229.

Schoenfeld H., Poeschl B., Frey J., Loetscher H., Hunziker W., Lustig A., Zulauf M. (1991) Efficient purification of recombinant human tumor necrosis factor b from *E. coli* yields biologically active protein with a trimeric structure that binds to both tumor necrosis factor receptors. J. Biol. Chem. 266, 3863–3869.

Sherblom A, Deckers J, Muchmore V (1988). The lectin-like interaction between recombinant tumor necrosis factor and uromodulin. J Biol Chem 263:5418–5424.

Shirai T, Yamaguchi H, Ito H, Todd C, Wallace R (1985) Cloning and expression in *Escherichia coli* of the gene for human tumor necrosis factor. Nature 313:803–806.

Sylvester D, Liu S, Meadows G (1990) Augmentation of antimetastatic activity of interferon and tumor necrosis factor by heparin. Immunopharmacol Immunotoxicol 12:161.

Taniguchi T, Sohmura Y (1991) Biotherapy 3:177–186.

Taverne J, Matthews N, Depledge P, Playfair J (1984) Malarial parasites and tumour cells are killed by the same component of tumour necrosis serum. Clin Exp Immunol 57: 293

Taverne J, Tavernier J, Fiers W, Playfair J (1987). Recombinant tumor necrosis factor inhibits malaria parasites in vivo but not in vitro. Clin Exp Immunol 67:1–4.

Titus R, Sherry B, Cerami A (1989). Tumor necrosis factor plays a protective role in experimental cutaneous leishmaniasis. J Exp Med 170:2097–2104.

Tracey K, Fong Y, Hesse D, Manogue K, Lee A, Kuo G, Lowry S, Cerami A (1987) Anti-cachectin/TNF monoclonal antibodies prevent septic shock during lethal bacteremia. Nature 330:662–664.

Tomazic V, Farha M, Loftus A, Elias E (1988) Anti-tumor activity of recombinant tumor necrosis factor on mouse fibrosarcoma in vivo and in vitro. J Immunol 140:4056.

Van Ostade X, Tavernier J, Prange T, Fiers W (1991) Localisation of the active site of human tumor necrosis factor by muational analysis EMBO J 10: 827–836

Van Ostade X, Vandenabeele P, Everaerdt B, Loetscher H, Gentz R, Brockhaus M, Lesslauer W, Tavernier J, Brouckaert P, Fiers W (1992) Human TNF mutants with selective activity on the p55 receptor. Nature 361:266–269.

Vilchèk J, Palombella V, Henriksen-Destefano V, Swensson C, Feinman R, Hirai M, Tsujimoto M (1986) Fibroblast growth enhancing activity and its relationship to other polypeptide growth factors J Exp Med 163: 632–643.

Wang A, Creasey A, Ladner M, Lin L, Strickler J, Van Arsdell J, Yamamoto R, Mark D (1985) Molecular cloning of the complementary DNA for human tumor necrosis factor. Science 228:149–154.

We claim:

1. A human or murine tumor necrosis factor mutein selected from the group consisting of:
   a TNF mutein wherein the amino acid region 105–110, or a part thereof, is deleted,
   a TNF mutein wherein at least one amino acid of the amino acid region 105–110 is in the D configuration,
   a TNF mutein wherein amino acid 105, 106, 107 or 110 is substituted,
   a TNF mutein wherein the combination of amino acid 105 and 110, 107 and 110, 105 and 110, or, 105 and 107 and 110, is substituted,
   which has at least one of the following activites:
   modulates the lectin-like activities of TNF,
   reduces the toxic activity of TNF,
   modulates the inflammatory cytokine-inducing capacity of TNF, and
   reduces the metastasis-promoting activity of TNF; and
   increases the serum half-live of TNF, and
   retains the tumoricidal activity of TNF, and
   which is characterized in that
   amino acid 1 to 8 of said human TNF is replaced by a sequence within the region amino acid 5 to 30 of laminin, and,
   amino acid 105 of said human TNF mutein is not proline or isoleucine, amino acid 106 of said human TNF mutein is not serine and amino acid 110 of said human TNF mutein is not lysine;
   or a salt of said muteins.

2. A TNF mutein according to claim 1, characterized in that the lectin-like activities are modulated with respect to TNF-α.

3. A TNF mutein according to claim 1, characterized in that the lectin-like activities are increased with respect to TNF-α.

4. A TNF mutein according to claim 1, characterized in that the lectin-like activities are reduced with respect to TNF-α.

5. A TNF mutein according to claim 1, characterized in that the toxic activity is reduced with respect to TNF-α.

6. A TNF mutein according to claim 1, characterized in that the inflammatory cytokine inducing capacities are modulated with respect to TNF-α.

7. A TNF mutein according to claim 1, characterized in that the inflammatory cytokine inducing capacities are increased with respect to TNF-α.

8. A TNF mutein according to claim 1, characterized in that the inflammatory cytokine inducing capacities are reduced with respect to TNF-α.

9. A TNF mutein according to claim 1, characterized in that the adhesion molecule inducing capacities are modulated with respect to TNF-α.

10. A TNF mutein according to claim 1, characterized in that the adhesion molecule inducing capacities are reduced with respect to TNF-α.

11. A TNF mutein according to claim 1 characterized in that the adhesion molecule inducing capacities are increased with respect to TNF-α.

12. A TNF mutein according to claim 1 characterized in that the metastasis promoting activity is reduced with respect to TNF-α.

13. A TNF mutein according to claim 1 characterized in that the tumoricidal activity is retained with respect to TNF-α.

14. A TNF mutein according to claim 1 characterized in that the tumoricidal activity is reduced with respect to TNF-α.

15. A TNF mutein according to claim 1 characterized in it shows an increased half life time with respect to TNF-α.

16. A TNF mutein according to claim 1 characterized in that at least part of the region extending from amino acid positions 105 to 110 of TNF-α, or the complete region corresponding to amino acid positions 105 to 110 of TNF-α has been deleted.

17. A TNF mutein according to claim 1 characterized in that at least one of the amino acids in the region extending from amino acids 105 to 110 of TNF-α, has been mutated or deleted.

18. A nucleic acid sequence encoding any of the polypeptides according to claim 1.

19. A process for the preparation of a polypeptide according to claim 1, comprising the steps of:
   transformation of an appropriate cellular host with a vector selected from the group consisting of a plasmid, a cosmid, a phage and a virus, in which a nucleic acid sequence coding for said polypeptide has been inserted, to form an insert, under the control of regulatory elements selected from the group consisting of a promoter recognized by the polymerases of the cellular host and, a ribosome binding site enabling the expression in said cellular host of said nucleic acid sequence,
   culture of said transformed cellular host under conditions enabling the expression of said insert; and
   recovering said polypeptide.

20. Cells transfected with a nucleic acid according to claim 18 coding for the TNF muteins, said nucleic acid being inserted into any suitable vector, with said cells being preferably autologus cells derived from a patient to be treated with such compositions; and with said vector-insert combination being constructed in such a way as to allow continuous expression of the TNF mutein at either a constant level, or at a level which can be modified, depending on the exact nature of the vector used to make the vector-insert combination.

21. The TNF mutein of claim 16 wherein at least the region covering amino acid positions 105 to 110 has been deleted.

22. The TNF mutein of claim 17 wherein at least one of the amino acids in the region extending from amino acids 105 to 110 has been mutated or deleted.

* * * * *

SEQUENCE LISTING ( 1 ) GENERAL INFORMATION:

( i i i ) NUMBER OF SEQUENCES: 36

( 2 ) INFORMATION FOR SEQ ID NO: 1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i i i ) ANTI-SENSE: NO ( i x ) FEATURE:
        ( A ) NAME/KEY: misc-feature
        ( B ) LOCATION: 1
        ( D ) OTHER INFORMATION: Xaa is Pro or Gln ( i x ) FEATURE:
        ( A ) NAME/KEY: misc-feature
        ( B ) LOCATION: 2
        ( D ) OTHER INFORMATION: Xaa is Lys or Arg ( i x ) FEATURE:
        ( A ) NAME/KEY: misc-feature
        ( B ) LOCATION: 3
        ( D ) OTHER INFORMATION: Xaa is Asp or Glu ( i x ) FEATURE:
        ( A ) NAME/KEY: misc-feature
        ( B ) LOCATION: 5
        ( D ) OTHER INFORMATION: Xaa is Pro, Ala, Thr, or Gly ( i x ) FEATURE:
        ( A ) NAME/KEY: misc-feature
        ( B ) LOCATION: 7
        ( D ) OTHER INFORMATION: Xaa is Gly, Ala, Thr, Pro, or Ser ( i x ) FEATURE:
        ( A ) NAME/KEY: misc-feature
        ( B ) LOCATION: 8
        ( D ) OTHER INFORMATION: Xaa is Ala, Pro, Gly, or Thr ( i x ) FEATURE:
        ( A ) NAME/KEY: misc-feature
        ( B ) LOCATION: 10
        ( D ) OTHER INFORMATION: Xaa is Leu or Ala ( i x ) FEATURE:
        ( A ) NAME/KEY: misc-feature
        ( B ) LOCATION: 1..3
        ( D ) OTHER INFORMATION: These amino acids may be present or absent ( i x ) FEATURE:
        ( A ) NAME/KEY: misc-feature
        ( B ) LOCATION: 10..14
        ( D ) OTHER INFORMATION: These amino acids may be present or absent (x i) SEQUENCE DESCRIPTION: SEQ ID NO: 1:

```
Xaa  Xaa  Xaa  Thr  Xaa  Glu  Xaa  Xaa  Gly  Xaa  Lys  Pro  Trp  Tyr
1                 5                      10
```

(2) INFORMATION FOR SEQ ID NO: 2:

(i) SEQUENCE CHARACTERISTICS:
    (A) LENGTH: 4009 base pairs
    (B) TYPE: nucleic acid
    (C) STRANDEDNESS: single
    (D) TOPOLOGY: circular (i i) MOLECULE TYPE: DNA (genomic)

(i i i) HYPOTHETICAL: NO (i i i) ANTI-SENSE: NO (v i i) IMMEDIATE SOURCE:
    (B) CLONE: pIG2

(x i) SEQUENCE DESCRIPTION: SEQ ID NO: 2:

| | | | | | |
|---|---|---|---|---|---|
| TTCCGGGGAT | CTCTCACCTA | CCAAACAATG | CCCCCCTGCA | AAAATAAAT | TCATATAAAA | 60 |
| AACATACAGA | TAACCATCTG | CGGTGATAAA | TTATCTCTGG | CGGTGTTGAC | ATAAATACCA | 120 |
| CTGGCGGTGA | TACTGAGCAC | ATCAGCAGGA | CGCACTGACC | ACCATGAAGG | TGACGCTCTT | 180 |
| AAAAATTAAG | CCCTGAAGAA | GGGCAGGGGT | ACCAGGAGGT | TTAAATCATG | GTAAGATCAA | 240 |
| GTAGTCAAAA | TTCGAGTGAC | AAGCCTGTAG | CCCACGTCGT | AGCAAACCAC | CAAGTGGAGG | 300 |
| AGCAGCTGGA | GTGGCTGAGC | CAGCGCGCCA | ACGCCCTCCT | GGCCAACGGC | ATGGATCTCA | 360 |
| AAGACAACCA | ACTAGTGGTG | CCAGCCGATG | GGTTGTACCT | TGTCTACTCC | CAGGTTCTCT | 420 |
| TCAAGGGACA | AGGCTGCCCC | GACTACGTGC | TCCTCACCCA | CACCGTCAGC | CGATTTGCTA | 480 |
| TCTCATACCA | GGAGAAAGTC | AACCTCCTCT | CTGCCGTCAA | GAGCCCCTGC | CCCAAGGACA | 540 |
| CCCCTGAGGG | GGCTGAGCTC | AAACCCTGGT | ATGAGCCCAT | ATACCTGGGA | GGAGTCTTCC | 600 |
| AGCTGGAGAA | GGGGGACCAA | CTCAGCGCTG | AGGTCAATCT | GCCCAAGTAC | TTAGACTTTG | 660 |
| CGGAGTCCGG | GCAGGTCTAC | TTTGGAGTCA | TTGCTCTGTG | AAGGGAATGG | GTGTTCATCC | 720 |
| ATTCTCTACC | CAGCCCCCAC | TCTGACCCCT | TTACTCTGAC | CCCTTTATTG | TCTACTCCTC | 780 |
| AGAGCCCCCA | GTCTGTGTCC | TTCTAACTTA | GAAAGGGGAT | TATGGCTCAG | AGTCCAACTC | 840 |
| TGTGCTCAGA | GCTTTCAACA | ACTACTCAGA | AACACAAGAT | GCTGGGACAG | TGACCTGGAC | 900 |
| TGTGGGCCTC | TCATGCACCA | CCATCAAGGA | CTCAAATGGG | CTTTCCGAAT | TCTCTAGAGT | 960 |
| CGACCTGCAG | CCCAAGCTTG | GCTGTTTTGG | CGGATGAGAG | AAGATTTTCA | GCCTGATACA | 1020 |
| GATTAAATCA | GAACGCAGAA | GCGGTCTGAT | AAAACAGAAT | TTGCCTGGCG | GCAGTAGCGC | 1080 |
| GGTGGTCCCA | CCTGACCCCA | TGCCGAACTC | AGAAGTGAAA | CGCCGTAGCG | CCGATGGTAG | 1140 |
| TGTGGGGTCT | CCCCATGCGA | GAGTAGGGAA | CTGCCAGGCA | TCAAATAAAA | CGAAAGGCTC | 1200 |
| AGTCGAAAGA | CTGGGCCTTT | CGTTTTATCT | GTTGTTTGTC | GGTGAACGCT | CTCCTGAGTA | 1260 |
| GGACAAATCC | GCCGGGAGCG | GATTTGAACG | TTGCGAAGCA | ACGGCCCGGA | GGGTGGCGGG | 1320 |
| CAGGACGCCC | GCCATAAACT | GCCAGGCATC | AAATTAAGCA | GAAGGCCATC | CTGACGGATG | 1380 |
| GCCTTTTTGC | GTTTCTACAA | ACTCTTTTGT | TTATTTTTCT | AAATACATTC | AAATATGTAT | 1440 |
| CCGCTCATGA | GACAATAACC | CTGATAAATG | CTTCAATAAT | AAAAGGATCT | AGGTGAAGAT | 1500 |
| CCTTTTTGAT | AATCTCATGA | CCAAAATCCC | TTAACGTGAG | TTTTCGTTCC | ACTGAGCGTC | 1560 |
| AGACCCCGTA | GAAAAGATCA | AAGGATCTTC | TTGAGATCCT | TTTTTTCTGC | GCGTAATCTG | 1620 |

```
CTGCTTGCAA ACAAAAAAAC CACCGCTACC AGCGGTGGTT TGTTTGCCGG ATCAAGAGCT    1680
ACCAACTCTT TTTCCGAAGG TAACTGGCTT CAGCAGAGCG CAGATACCAA ATACTGTCCT    1740
TCTAGTGTAG CCGTAGTTAG GCCACCACTT CAAGAACTCT GTAGCACCGC CTACATACCT    1800
CGCTCTGCTA ATCCTGTTAC CAGTGGCTGC TGCCAGTGGC GATAAGTCGT GTCTTACCGG    1860
GTTGGACTCA AGACGATAGT TACCGGATAA GGCGCAGCGG TCGGGCTGAA CGGGGGGTTC    1920
GTGCACACAG CCCAGCTTGG AGCGAACGAC CTACACCGAA CTGAGATACC TACAGCGTGA    1980
GCATTGAGAA AGCGCCACGC TTCCCGAAGG GAGAAAGGCG ACAGGTATC CGGTAAGCGG     2040
CAGGGTCGGA ACAGGAGAGC GCACGAGGGA GCTTCCAGGG GGAAACGCCT GGTATCTTTA    2100
TAGTCCTGTC GGGTTTCGCC ACCTCTGACT TGAGCGTCGA TTTTTGTGAT GCTCGTCAGG    2160
GGGGCGGAGC CTATGGAAAA ACGCCAGCAA CGCGGCCTTT TACGGTTCC TGGCCTTTTG     2220
CTGGCCTTTT GCTCACATGT TCTTTCCTGC GTTATCCCCT GATTCTGTGG ATAACCGTAT    2280
TACCGCCTTT GAGTGAGCTG ATACCGCTCG CCGCAGCCGA ACGACCGAGC GCAGCGAGTC    2340
AGTGAGCGAG GAAGCGGAAG AGCGCTGACT TCCGCGTTTC CAGACTTTAC GAAACACGGA    2400
AACCGAAGAC CATTCATGTT GTTGCTCAGG TCGCAGACGT TTTGCAGCAG CAGTCGCTTC    2460
ACGTTCGCTC GCGTATCGGT GATTCATTCT GCTAACCAGT AAGGCAACCC CGCCAGCCTA    2520
GCCGGGTCCT CAACGACAGG AGCACGATCA TGCGCACCCG TGGCCAGGAC CCAACGCTGC    2580
CCGAGATGCG CCGCGTGCGG CTGCTGGAGA TGGCGGACGC GATGGATATG TTCTGCCAAG    2640
GGTTGGTTTG CGCATTCACA GTTCTCCGCA AGAATTGATT GGCTCCAATT CTTGGAGTGG    2700
TGAATCCGTT AGCGAGGTGC CGCCGGCTTC CATTCAGGTC GAGGTGGCCC GGCTCCATGC    2760
ACCGCGACGC AACGCGGGGA GGCAGACAAG GTATAGGGCG CGCCTACAA TCCATGCCAA     2820
CCCGTTCCAT GTGCTCGCCG AGGCGGCATA AATCGCCGTG ACGATCAGCG GTCCAGTGAT    2880
CGAAGTTAGG CTGGTAAGAG CCGCGAGCGA TCCTTGAAGC TGTCCTGAT GGTCGTCATC     2940
TACCTGCCTG GACAGCATGG CCTGCAACGC GGGCATCCCG ATGCCGCCGG AAGCGAGAAG    3000
AATCATAATG GGGAAGGCCA TCCAGCCTCG CGTCGCGAAC GCCAGCAAGA CGTAGCCCAG    3060
CGCGTCGGCC GCCATGCCGG CGATAATGGC CTGCTTCTCG CCGAAACGTT TGGTGGCGGG    3120
ACCAGTGACG AAGGCTTGAG CGAGGGCGTG CAAGATTCCG AATACCGCAA GCGACAGGCC    3180
GATCATCGTC GCGCTCCAGC GAAAGCGGTC CTCGCCGAAA ATGACCCAGA GCGCTGCCGG    3240
CACCTGTCCT ACGAGTTGCA TGATAAAGAA GACAGTCATA AGTGCGGCGA CGATAGTCAT    3300
GCCCCGCGCC CACCGGAAGG AGCTGACTGG GTTGAAGGCT CTCAAGGGCA TCGGTCGACG    3360
CTCTCCCTTA TGCGACTCCT GCATTAGGAA GCAGCCCAGT AGTAGGTTGA GGCCGTTGAG    3420
CACCGCCGCC GCAAGGAATG GTGCATGCAA GGAGATGGCG CCCAACAGTC CCCCGGCCAC    3480
GGGGCCTGCC ACCATACCCA CGCCGAAACA AGCGCTCATG AGCCCGAAGT GGCGAGCCCG    3540
ATCTTCCCCA TCGGTGATGT CGGCGATATA GGCGCCAGCA ACCGCACCTG TGGCGCCGGT    3600
GATGCCGGCC ACGATGCGTC CGGCGTAGAG GATCCACAGG ACGGGTGTGG TCGCCATGAT    3660
CGCGTAGTCG ATAGTGGCTC CAAGTAGCGA AGCGAGCAGG ACTGGGCGGC GGCCAAAGCG    3720
GTCGGACAGT GCTCCGAGAA CGGGTGCGCA TAGAAATTGC ATCAACGCAT ATAGCGCTAG    3780
CAGCACGCCA TAGTGACTGG CGATGCTGTC GGAATGGACG ATATCCCGCA AGAGGCCCGG    3840
CAGTACCGGC ATAACCAAGC CTATGCCTAC AGCATCCAGG GTGACGGTGC CGAGGATGAC    3900
GATGAGCGCA TTGTTAGATT TCATACACGG TGCCTGACTG CGTTAGCAAT TTAACTGTGA    3960
TAAACTACCG CATTAAAGCT TATCGATGAT AAGCTGTCAA ACATGAGAA                4009
```

( 2 ) INFORMATION FOR SEQ ID NO: 3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 3:

CATGCTCAGA TCAAGTAGTC AAAATT                        26

( 2 ) INFORMATION FOR SEQ ID NO: 4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: YES ( x i ) SEQUENCE DESCRIPTION: SEQ ID NO: 4:

CGAATTTTGA CTACTTGATC TGAGCATG                      28

( 2 ) INFORMATION FOR SEQ ID NO: 5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 5:

CAAGGACGCT CCGGAGGGGG CTGAGCT                       27

( 2 ) INFORMATION FOR SEQ ID NO: 6:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: YES ( x i ) SEQUENCE DESCRIPTION: SEQ ID NO: 6:

CAGCCCCTC CGGAGCGTC                                19

( 2 ) INFORMATION FOR SEQ ID NO: 7:

(i) SEQUENCE CHARACTERISTICS:
  (A) LENGTH: 27 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 7:

CAAGGACACC GCTGAGGGCG CCGAGCT 27

(2) INFORMATION FOR SEQ ID NO: 8:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iii) ANTI-SENSE: YES (xi) SEQUENCE DESCRIPTION: SEQ ID NO: 8:

CGGCGCCCTC AGCGGTGTC 19

(2) INFORMATION FOR SEQ ID NO: 9:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 9:

CAAGGACACC CCTGCAGGCG CTGAGCT 27

(2) INFORMATION FOR SEQ ID NO: 10:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iii) ANTI-SENSE: YES (xi) SEQUENCE DESCRIPTION: SEQ ID NO: 10:

CAGCGCCTGC AGGGGTGTC 19

(2) INFORMATION FOR SEQ ID NO: 11:

(i) SEQUENCE CHARACTERISTICS:
    (A) LENGTH: 27 base pairs
    (B) TYPE: nucleic acid
    (C) STRANDEDNESS: single (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 11:

CAAGGACACC CCTGAGGGCG CCGCCCT                27

(2) INFORMATION FOR SEQ ID NO: 12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (xi) SEQUENCE DESCRIPTION: SEQ ID NO: 12:

AGGGCGGCGC CCTCAGGGGT GTC                23

(2) INFORMATION FOR SEQ ID NO: 13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 13:

CAAGGACACC CCTGCAGGCG CCGCCCT                27

(2) INFORMATION FOR SEQ ID NO: 14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (xi) SEQUENCE DESCRIPTION: SEQ ID NO: 14:

AGGGCGGCGC CTGCAGGGGT GTC                23

(2) INFORMATION FOR SEQ ID NO: 15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(i i i) HYPOTHETICAL: NO (i i i) ANTI-SENSE: NO (x i) SEQUENCE DESCRIPTION: SEQ ID NO: 15:

CAAGGACGCT CCGGAGGGCG CCGCCCT 27

(2) INFORMATION FOR SEQ ID NO: 16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i i i) ANTI-SENSE: YES (x i) SEQUENCE DESCRIPTION: SEQ ID NO: 16:

AGGGCGGCGC CCTCCGGAGC GTC 23

(2) INFORMATION FOR SEQ ID NO: 17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i i i) ANTI-SENSE: NO (x i) SEQUENCE DESCRIPTION: SEQ ID NO: 17:

CAAGGATGCC CCGGCGGGTG CAGAGCT 27

(2) INFORMATION FOR SEQ ID NO: 18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i i i) ANTI-SENSE: YES (x i) SEQUENCE DESCRIPTION: SEQ ID NO: 18:

CTGCACCCGC CGGGGCATC 19

(2) INFORMATION FOR SEQ ID NO: 19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i i i) ANTI-SENSE: NO ( x i ) SEQUENCE DESCRIPTION: SEQ ID NO: 19:

CAAGGATGCT CCGGCCGGTG CGGCCCT 27

(2) INFORMATION FOR SEQ ID NO: 20:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: YES ( x i ) SEQUENCE DESCRIPTION: SEQ ID NO: 20:

AGGGCCGCAC CGGCCGGAGC ATC 23

(2) INFORMATION FOR SEQ ID NO: 21:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 21:

CAAGGACCTC AAACCATGGT ATGAGCCCAT ATAC 34

(2) INFORMATION FOR SEQ ID NO: 22:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: YES ( x i ) SEQUENCE DESCRIPTION: SEQ ID NO: 22:

ATGGGCTCAT ACCATGGTTT GAGGTC 26

(2) INFORMATION FOR SEQ ID NO: 23:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 23:

Thr Pro Glu Gly Ala Glu
    1                 5

(2) INFORMATION FOR SEQ ID NO: 24:

( i ) SEQUENCE CHARACTERISTICS:

(A) LENGTH: 17 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Biotin-Gly-Gly is coupled to the N- terminus of the peptide"

(xi) SEQUENCE DESCRIPTION: SEQ ID NO: 24:

Cys Gly Pro Lys Asp Thr Pro Glu Gly Ala Glu Leu Lys Pro Trp Tyr
1               5                       10                      15
Cys (2) INFORMATION FOR SEQ ID NO: 25:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE: peptide (ix) FEATURE:
(A) NAME/KEY: Binding-site
(B) LOCATION: 1
(D) OTHER INFORMATION: /note= "Biotin-Gly-Gly is coupled to the N- terminus of the peptide"

(xi) SEQUENCE DESCRIPTION: SEQ ID NO: 25:

Cys Gly Gln Arg Glu Thr Pro Glu Gly Ala Glu Ala Lys Pro Trp Tyr
1               5                       10                      15
Cys (2) INFORMATION FOR SEQ ID NO: 26:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (ix) FEATURE:
(A) NAME/KEY: Binding-site
(B) LOCATION: 1
(D) OTHER INFORMATION: /note= "Biotin-Gly-Gly is coupled to the N- terminus of the peptide"

(xi) SEQUENCE DESCRIPTION: SEQ ID NO: 26:

Cys Thr Pro Glu Gly Ala Glu Cys
1               5

(2) INFORMATION FOR SEQ ID NO: 27:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(A) NAME/KEY: Binding-site
(B) LOCATION: 1

(D) OTHER INFORMATION: /note= "Biotin-Gly-Gly is coupled
to the N- terminus of the peptide"

(xi) SEQUENCE DESCRIPTION: SEQ ID NO: 27:

Glu Gly Ala Glu Leu Lys Pro Trp Tyr
1               5

(2) INFORMATION FOR SEQ ID NO: 28:

(i) SEQUENCE CHARACTERISTICS:
    (A) LENGTH: 3 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Binding-site
    (B) LOCATION: 1
    (D) OTHER INFORMATION: /note= "Biotin-Gly-Gly is coupled
        to the N- terminus of the peptide"

(xi) SEQUENCE DESCRIPTION: SEQ ID NO: 28:

Thr Pro Glu
1

(2) INFORMATION FOR SEQ ID NO: 29:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 1..8
    (D) OTHER INFORMATION: /note= "D amino acids"

(xi) SEQUENCE DESCRIPTION: SEQ ID NO: 29:

Cys Thr Pro Glu Gly Ala Glu Cys
1               5

(2) INFORMATION FOR SEQ ID NO: 30:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Binding-site
    (B) LOCATION: 1
    (D) OTHER INFORMATION: /note= "Biotin-Gly-Gly is coupled
        to the N- terminus of the peptide"

(xi) SEQUENCE DESCRIPTION: SEQ ID NO: 30:

Cys Ala Pro Glu Gly Ala Glu Cys
1               5

(2) INFORMATION FOR SEQ ID NO: 31:

(i) SEQUENCE CHARACTERISTICS:
    (A) LENGTH: 8 amino acids
    (B) TYPE: amino acid
    (C) STRANDEDNESS: single (D) TOPOLOGY: linear (i i) MOLECULE TYPE: peptide (i x) FEATURE:
    (A) NAME/KEY: Binding-site
    (B) LOCATION: 1
    (D) OTHER INFORMATION: /note= "Biotin-Gly-Gly is coupled
        to the N- terminus of the peptide"

(x i) SEQUENCE DESCRIPTION: SEQ ID NO: 31:

Cys Thr Ala Glu Gly Ala Glu Cys
1               5

(2) INFORMATION FOR SEQ ID NO: 32:

(i) SEQUENCE CHARACTERISTICS:
        (A) LENGTH: 8 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Binding-site
        (B) LOCATION: 1
        (D) OTHER INFORMATION: /note= "Biotin-Gly-Gly is coupled
            to the N- terminus of the peptide"

(x i) SEQUENCE DESCRIPTION: SEQ ID NO: 32:

Cys Thr Pro Ala Gly Ala Glu Cys
1               5

(2) INFORMATION FOR SEQ ID NO: 33:

(i) SEQUENCE CHARACTERISTICS:
        (A) LENGTH: 8 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Binding-site
        (B) LOCATION: 1
        (D) OTHER INFORMATION: /note= "Biotin-Gly-Gly is coupled
            to the N- terminus of the peptide"

(x i) SEQUENCE DESCRIPTION: SEQ ID NO: 33:

Cys Thr Pro Glu Ala Ala Glu Cys
1               5

(2) INFORMATION FOR SEQ ID NO: 34:

(i) SEQUENCE CHARACTERISTICS:
        (A) LENGTH: 8 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Binding-site
        (B) LOCATION: 1
        (D) OTHER INFORMATION: /note= "Biotin-Gly-Gly is coupled
            to the N- terminus of the peptide"

(x i) SEQUENCE DESCRIPTION: SEQ ID NO: 34:

Cys Thr Pro Glu Gly Ala Ala Cys
1               5

( 2 ) INFORMATION FOR SEQ ID NO:35:

( i ) SEQUENCE CHARACTERISTICS:
        ( A ) LENGTH: 157 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:35:

```
Val Arg Ser Ser Ser Arg Thr Pro Ser Asp Lys Pro Val Ala His Val
 1               5                  10                  15
Val Ala Asn Pro Gln Ala Glu Gly Gln Leu Gln Trp Leu Asn Arg Arg
             20                  25                  30
Ala Asn Ala Leu Leu Ala Asn Gly Val Glu Leu Arg Asp Asn Gln Leu
         35                  40                  45
Val Val Pro Ser Glu Gly Leu Tyr Leu Ile Tyr Ser Gln Val Leu Phe
     50                  55                  60
Lys Gly Gln Gly Cys Pro Ser Thr His Val Leu Leu Thr His Thr Ile
 65                  70                  75                  80
Ser Arg Ile Ala Val Ser Tyr Gln Thr Lys Val Asn Leu Leu Ser Ala
                 85                  90                  95
Ile Lys Ser Pro Cys Gln Arg Glu Thr Pro Glu Gly Ala Glu Ala Lys
             100                 105                 110
Pro Trp Tyr Glu Pro Ile Tyr Leu Gly Gly Val Phe Gln Leu Glu Lys
             115                 120                 125
Gly Asp Arg Leu Ser Ala Glu Ile Asn Arg Pro Asp Tyr Leu Asp Phe
         130                 135                 140
Ala Glu Ser Gly Gln Val Tyr Phe Gly Ile Ile Ala Leu
 145                 150                 155
```

( 2 ) INFORMATION FOR SEQ ID NO:36:

( i ) SEQUENCE CHARACTERISTICS:
        ( A ) LENGTH: 156 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:36:

```
Leu Arg Ser Ser Ser Gln Asn Ser Ser Asp Lys Pro Val Ala His Val
 1               5                  10                  15
Val Ala Asn His Gln Val Glu Glu Gln Leu Glu Trp Leu Ser Gln Arg
             20                  25                  30
Ala Asn Ala Leu Leu Ala Asn Gly Met Asp Leu Lys Asp Asn Gln Leu
         35                  40                  45
Val Val Pro Ala Asp Gly Leu Tyr Leu Val Tyr Ser Gln Val Leu Phe
     50                  55                  60
Lys Gly Gln Gly Cys Pro Asp Tyr Val Leu Leu Thr His Thr Val Ser
 65                  70                  75                  80
Arg Phe Ala Ile Ser Tyr Gln Glu Lys Val Asn Leu Leu Ser Ala Val
                 85                  90                  95
Lys Ser Pro Cys Pro Lys Asp Thr Pro Glu Gly Ala Glu Leu Lys Pro
             100                 105                 110
Trp Tyr Glu Pro Ile Tyr Leu Gly Gly Val Phe Gln Leu Glu Lys Gly
             115                 120                 125
```

| Asp | Gln | Leu | Ser | Ala | Glu | Val | Asn | Leu | Pro | Lys | Tyr | Leu | Asp | Phe | Ala |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |
| Glu | Ser | Gly | Gln | Val | Tyr | Phe | Gly | Val | Ile | Ala | Leu |     |     |     |     |
| 145 |     |     |     |     | 150 |     |     |     |     | 155 |     |     |     |     |     |